United States Patent
Sazuka et al.

(10) Patent No.: US 10,867,013 B2
(45) Date of Patent: Dec. 15, 2020

(54) INFORMATION PROCESSING APPARATUS, INFORMATION PROCESSING METHOD, AND PROGRAM

(71) Applicant: SONY CORPORATION, Tokyo (JP)

(72) Inventors: Naoya Sazuka, Tokyo (JP); Yoshihiro Wakita, Tokyo (JP); Kazuyuki Kanosue, Tokyo (JP)

(73) Assignee: SONY CORPORATION, Tokyo (JP)

( * ) Notice: Subject to any disclaimer, the term of this patent is extended or adjusted under 35 U.S.C. 154(b) by 463 days.

(21) Appl. No.: 15/552,419

(22) PCT Filed: May 9, 2016

(86) PCT No.: PCT/JP2016/002265
§ 371 (c)(1),
(2) Date: Aug. 21, 2017

(87) PCT Pub. No.: WO2016/185685
PCT Pub. Date: Nov. 24, 2016

(65) Prior Publication Data
US 2018/0039751 A1 Feb. 8, 2018

(30) Foreign Application Priority Data

May 19, 2015 (JP) ................ 2015-101829

(51) Int. Cl.
*G06F 17/00* (2019.01)
*G06F 19/00* (2018.01)
*G16H 40/63* (2018.01)
*A61B 5/11* (2006.01)
*A61B 5/00* (2006.01)
*G06F 1/16* (2006.01)

(52) U.S. Cl.
CPC ......... *G06F 19/3418* (2013.01); *G16H 40/63* (2018.01); *A61B 5/11* (2013.01); *A61B 5/6802* (2013.01); *G06F 1/163* (2013.01)

(58) Field of Classification Search
CPC .................................................. G06F 19/3418
See application file for complete search history.

(56) References Cited

U.S. PATENT DOCUMENTS

2008/0214903 A1   9/2008  Orbach

FOREIGN PATENT DOCUMENTS

EP         2654030 A1    10/2013
JP         2013-078593    5/2013
WO     WO2014/150221 A1   9/2014

*Primary Examiner* — Kesha Frisby
(74) *Attorney, Agent, or Firm* — Paratus Law Group, PLLC

(57) ABSTRACT

There is provided an information processing apparatus including circuitry configured to initiate a providing of guidance on at least one selected from a group consisting of a speed, a pitch, and a stride of a user's movement, based on a movement characteristic representing a relation among a combination of the speed, the pitch, and the stride during the user's movement, wherein the guidance is provided based on sensing information associated with the user's movement.

22 Claims, 66 Drawing Sheets

FIG. 47
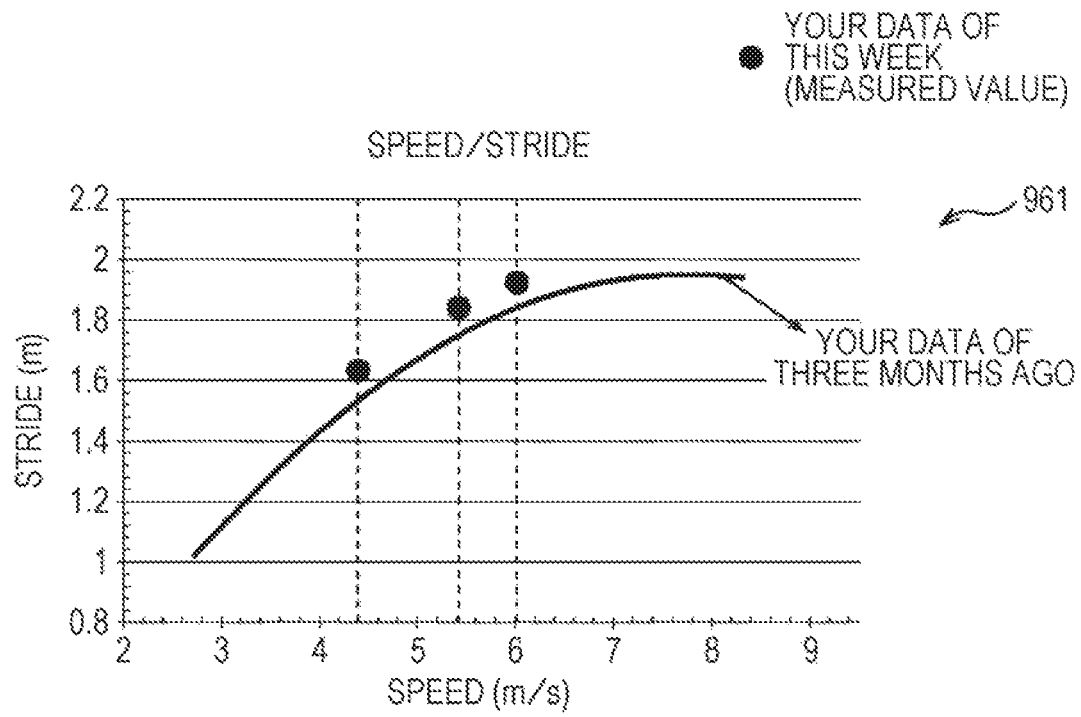
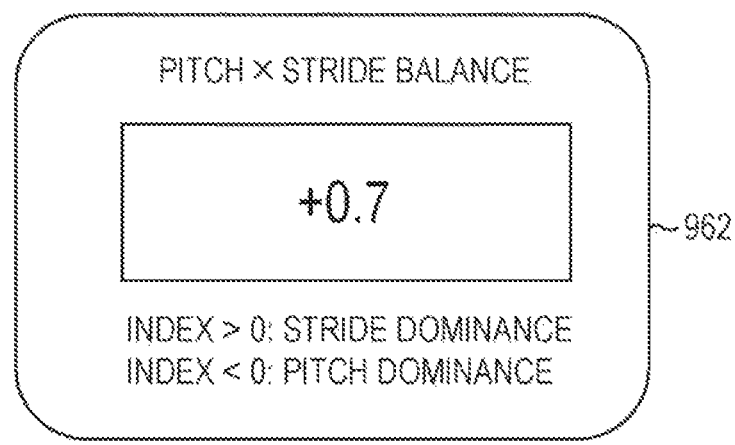

FIG. 51
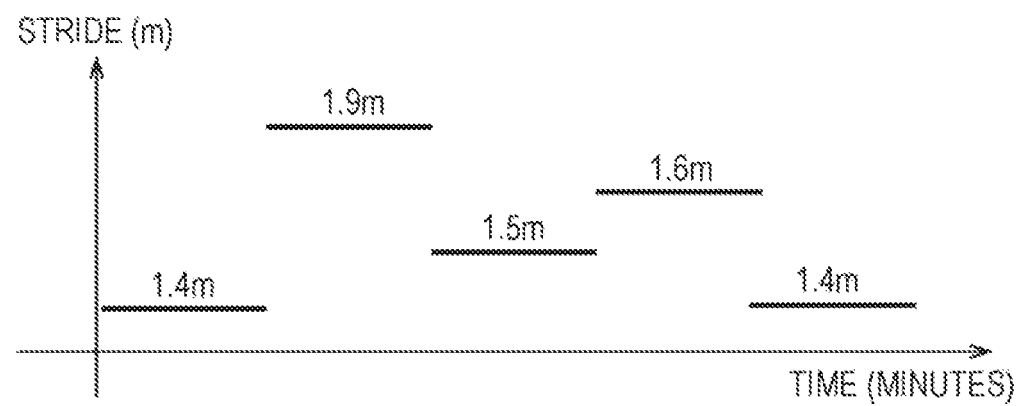
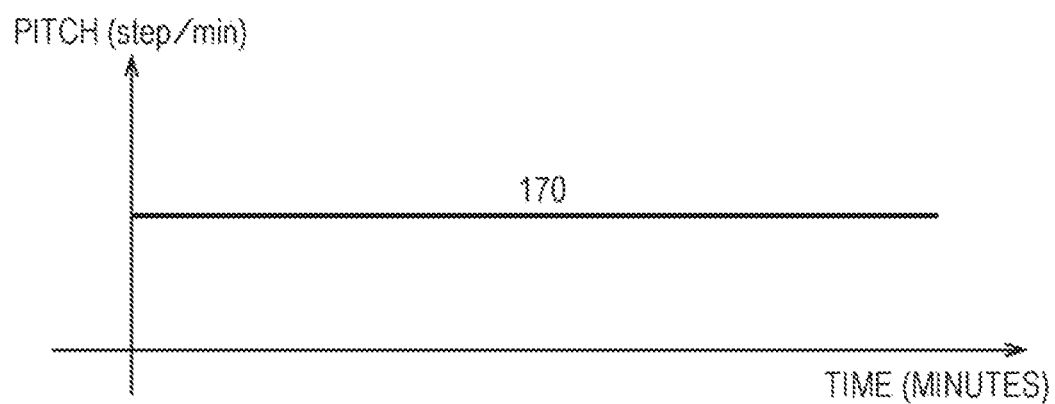

INFORMATION PROCESSING APPARATUS, INFORMATION PROCESSING METHOD, AND PROGRAM

CROSS REFERENCE TO RELATED APPLICATIONS

This application is a National Stage Patent Application of PCT International Patent Application No. PCT/JP2016/002265 filed on May 9, 2016 under 35 U.S.C. § 371, which claims the benefit of Japanese Priority Patent Application JP 2015-101829 filed on May 19, 2015, the entire contents of which are incorporated herein by reference.

TECHNICAL FIELD

The present technology relates to an information processing apparatus, an information processing method, and a program and more particularly, to an information processing apparatus, an information processing method, and a program capable of appropriately supporting the movement of a person such as running.

BACKGROUND ART

In related art, a system has been proposed which installs a wearable terminal to a user, monitors the speed, the acceleration, the pace, the step count rate, the heart rate, and the like, and performs feedback or interaction for user's performance, a training method, or the like (for example, see Patent Literature 1).

CITATION LIST

Patent Literature

[PTL 1]
JP 2013-78593 A

SUMMARY

Technical Problem

However, in a technology disclosed in PTL 1, the analysis of user's running state based on the pitch and the stride of the user has not been reviewed. Thus, according to the technology disclosed in PTL 1, it is difficult to support running from a viewpoint of the pitch and the stride. For example, according to the technology disclosed in PTL 1, it is difficult to give advice or training that is appropriate for the pitch and the stride of the user.

It is desirable to appropriately support the movement of a person such as running.

Solution to Problem

One aspect of the present disclosure is directed to an information processing apparatus including circuitry configured to initiate a providing of guidance on at least one selected from a group consisting of a speed, a pitch, and a stride of a user's movement, based on a movement characteristic representing a relation among a combination of the speed, the pitch, and the stride during the user's movement, wherein the guidance is provided based on sensing information associated with the user's movement.

Another aspect of the present disclosure is directed to the information processing apparatus, wherein the circuitry is further configured to control presentation of at least one of the movement characteristic of the user's movement and a result of an analysis of a movement state of the user based on the movement characteristic.

Another aspect of the present disclosure is directed to the information processing apparatus, wherein the circuitry is further configured to execute control such that a result of analyzing balance of the pitch and the stride of the user's movement based on the movement characteristic is presented.

Another aspect of the present disclosure is directed to the information processing apparatus, wherein the circuitry is further configured to execute control such that transitions of time series of the balance of the pitch and the stride along with the speed of the user's movement are presented.

Another aspect of the present disclosure is directed to the information processing apparatus, wherein the circuitry is further configured to control presentation of at least one of a result of comparing balances of the pitches and the strides of the user at a plurality of time points in a time series and a result of comparing balances of the pitches and the strides of a plurality of users' movements.

Another aspect of the present disclosure is directed to the information processing apparatus, wherein the circuitry is further configured to analyze a movement state of the user's movement based on the user's movement characteristic.

Another aspect of the present disclosure is directed to the information processing apparatus, wherein the guidance is provided such that one of the speed, the pitch, and the stride is fixed, and the remaining two thereof are changed.

Another aspect of the present disclosure is directed to the information processing apparatus, wherein the guidance is provided on the pitch and the stride of the user's movement such that a heart rate or a pulse rate of the user is within a threshold amount of a predetermined constant.

Another aspect of the present disclosure is directed to the information processing apparatus, wherein the circuitry is further configured to initiate generation of a plan including at least one selected from a group consisting of distribution of the pitch and the stride in a course in which the user moves and distribution of the speed in the course based on a stamina characteristic of the user, wherein the guidance is provided on the speed, the pitch, and the stride of the user's movement, based on the generated plan.

Another aspect of the present disclosure is directed to the information processing apparatus, wherein the circuitry is further configured to update the plan during the user's movement based on the movement state of the user and a condition.

Another aspect of the present disclosure is directed to the information processing apparatus, wherein the circuitry is further configured to update the plan while adjusting a remainder of a stamina amount according to the stamina characteristic of the user at a goal time based on a remaining distance of the course.

Another aspect of the present disclosure is directed to the information processing apparatus, wherein the stamina characteristic of the user includes a stamina efficiency characteristic representing a relation among at least one selected from a group consisting of the speed, the pitch, and the stride of the user's movement, a remaining stamina amount and stamina efficiency, and a stamina capacity of the user.

Another aspect of the present disclosure is directed to the information processing apparatus, wherein the guidance is provided on the stride in a case where the speed of the user is less than a predetermined speed threshold, and guidance is provided on the pitch in a case where the speed of the user is equal to or greater than the predetermined speed threshold.

Another aspect of the present disclosure is directed to the information processing apparatus, wherein the circuitry is further configured to analyze the movement characteristic of the user's movement based on measurement results of the pitch and the stride of the user's movement for at least two different speeds including a first speed and a second speed.

Another aspect of the present disclosure is directed to the information processing apparatus, wherein the first speed and the second speed are lower than a switching speed that is a speed at which the circuitry is configured to control switching between a method of controlling acceleration by increasing the stride and a method of controlling acceleration by increasing the pitch.

Another aspect of the present disclosure is directed to the information processing apparatus, wherein the circuitry is further configured to analyze the movement characteristic of the user's movement based on measurement results of the pitch and the stride of the user's movement for at least three different speeds including a first speed lower than a switching speed that is a speed at which the circuitry is configured to control switching between a method of controlling acceleration by increasing the stride and a method of controlling acceleration by increasing the pitch, a second speed higher than the switching speed, and a third speed that is between the first speed and the second speed.

Another aspect of the present disclosure is directed to the information processing apparatus, wherein the circuitry is further configured to analyze a cardiorespiratory capacity of the user based on a heart rate or a pulse rate measured while guidance is provided on the at least one selected from the group consisting of the speed, the pitch, and the stride of the user's movement.

Another aspect of the present disclosure is directed to the information processing apparatus, wherein the cardiorespiratory capacity includes an average heart rate and a highest heart rate of the user.

Another aspect of the present disclosure is directed to the information processing apparatus, wherein the circuitry is further configured to analyze a stamina characteristic of the user based on a combination of the speed measured while guidance is provided on the at least one selected from the group consisting of the speed, the pitch, and the stride of the user's movement and a measurement result of a heart rate or a pulse rate.

Another aspect of the present disclosure is directed to the information processing apparatus, wherein the movement characteristic of the user's movement represents a combination of the pitch and the stride at each speed during the user's movement, and the movement state is a running state of the user.

Another aspect of the present disclosure is directed to the information processing apparatus, wherein the pitch is determined based on a number of unit movement operations of the user per unit of time.

Another aspect of the present disclosure is directed to an information processing method, performed via at least one processor, the method including guiding at least one selected from a group consisting of a speed, a pitch, and a stride of a user's movement, based on a movement characteristic representing a relation among a combination of the speed, the pitch, and the stride during the user's movement, wherein the guidance is provided based on sensing information associated with the user's movement. Another aspect of the present disclosure is directed to a non-transitory computer-readable medium having embodied thereon a program, which when executed by a computer causes the computer to execute a method, the method including guiding at least one selected from a group consisting of a speed, a pitch, and a stride of a user's movement, based on a movement characteristic representing a relation among a combination of the speed, the pitch, and the stride during the user's movement, wherein the guidance is provided based on sensing information associated with the user's movement.

Another aspect of the present disclosure is directed to a non-transitory computer-readable medium having embodied thereon a program, which when executed by a computer causes the computer to execute a method, the method including guiding at least one selected from a group consisting of a speed, a pitch, and a stride of a user's movement, based on a movement characteristic representing a relation among a combination of the speed, the pitch, and the stride during the user's movement, wherein the guidance is provided based on sensing information associated with the user's movement.

According to an embodiment of the present technology, at least one of a speed, a pitch, and a stride of a user's movement is guided based on a movement characteristic representing a relation among a combination of the speed, the pitch, and the stride at the time of user's movement based on sensing information associated with the user's movement.

Advantageous Effects of Invention

According to one or more embodiments of the present technology, the movement of a person such as running can be appropriately supported.

The effects described here are not necessarily limited thereto, but an effect not disclosed in the present disclosure may be present.

BRIEF DESCRIPTION OF DRAWINGS

FIG. 47 is a diagram that illustrates a third example of the screen presenting a comparison result of data.

FIG. 51 is a diagram that illustrates an example of the running parameter control training support process.

DESCRIPTION OF EMBODIMENTS

Figure 1:
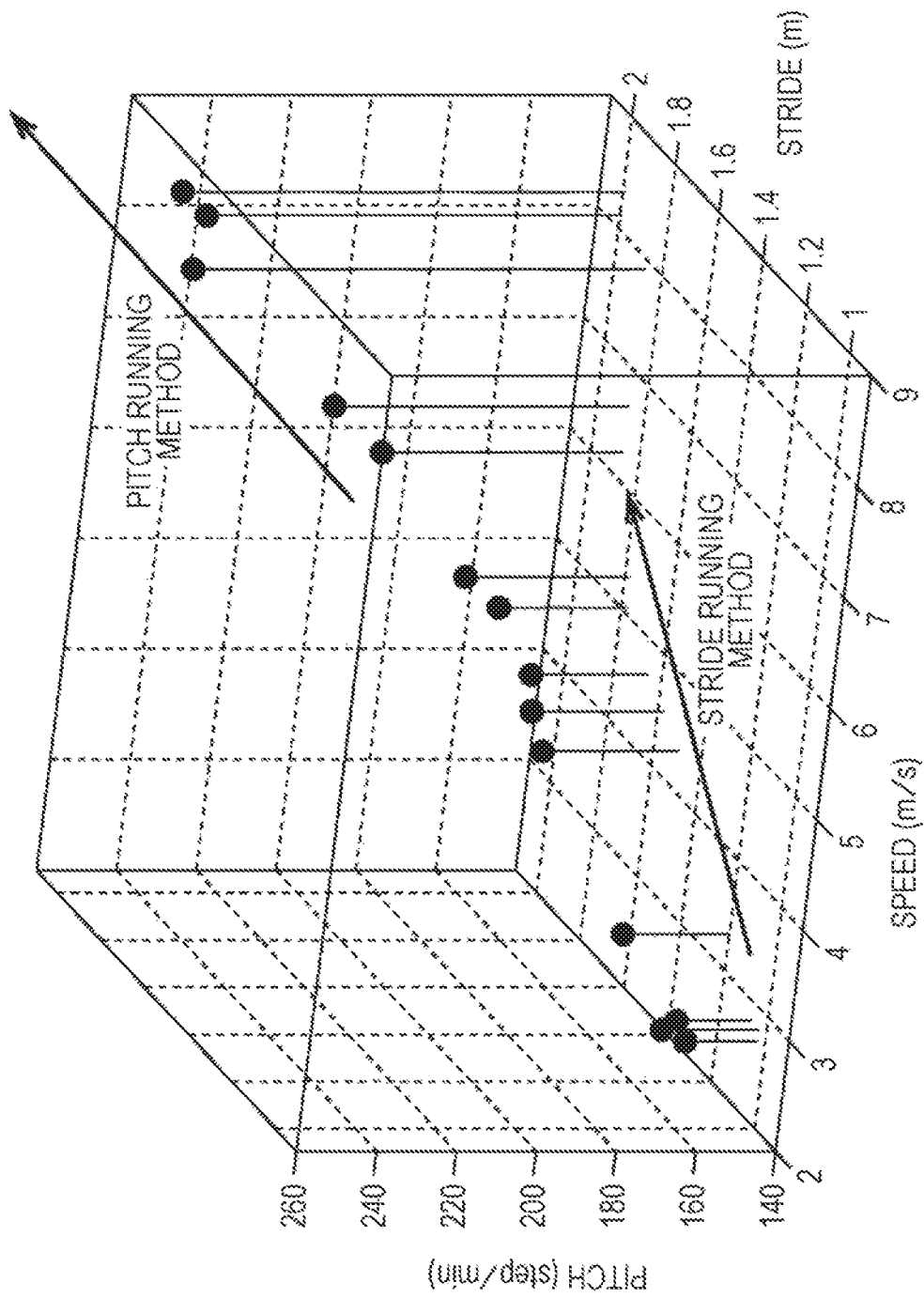
FIG. 1 is a graph that illustrates an example of a speed-pitch-stride characteristic.

Hereinafter, embodiments of the present technology will be described. The description will be presented in the following order.
1. Definition of Term
2. Person's Running Characteristic
3. Embodiment
4. Modified Example.

1. Definition of Term

First, main terms used in this specification will be defined. Hereinafter, unless otherwise mentioned, each term will be used based on the following definition.

A speed is a speed at which a person runs and is represented in units of m/s (meter per second), m/min (meter per minute), or the like. The speed will be also referred to as a pace.

A pitch is the number of rotations of legs of a person and is represented in units of step/min (step per minute) or the like. While a term called cadence is frequently used in technical papers, in this specification, a pitch having a high degree of recognition in Japan will be mainly used.

A stride is a person's stride and is represented in units of m (meters), cm (centimeters), or the like. While a term called a step length is frequently used in technical papers, in this specification, a stride having a high degree of recognition in Japan will be mainly used.

Here, a relation of "speed=stride×pitch" is formed.

A stamina amount is a parameter that is defined based on the amount of in-body resources or in-body formed materials having the following properties. For example, there is an in-body resource having a property of consumption dominance at the time of running since it takes a long time for the recovery after the resource is consumed at the time of running. In addition, there is an in-body formed material having a property of accumulation dominance at the time of running since it inhibits running by being accumulated and has a property of taking a long time for decomposition and discharge. The influence of the in-body resource and the in-body formed material is observed as a phenomenon in which the running state, generally, initially maintained moderately is degraded in accordance with an increase in the running distance. The stamina amount, for example, is defined by the amounts of the in-body resource and the in-body formed material. Here, the accumulation amount of the in-body formed material may be regarded as a consumption amount of the in-body resource by inverting the sign of a numerical value representing the accumulation amount.

It is not necessary for the stamina amount to respond to the density, the accumulation amount, or the like of an actual physiological substance, and, for example, the stamina amount is represented by an internal variable having a property of a conserved quantity appearing when machine learning of a relation between a running pattern and a runnable distance is executed. The running pattern, for example, is a pattern represented by a speed, a pitch, and a stride. The runnable distance is a distance that can be continuously run without walking or a break being interposed between running.

A stamina depletion point is a time point when running is rapidly degraded at a certain time point in a case where running is continuously performed with the stamina amount being decreased.

A stamina capacity is an accumulated value of a stamina amount consumed until the condition arrives at the stamina depletion point after starting running in a good state in which fatigue does not remain.

Each of the stamina amount and the stamina capacity is represented by one or a plurality of numerical values corresponding to one or a plurality of in-body resources. In a case where the depletion of a specific in-body resource occurs first all the time, the stamina amount and the stamina capacity can be defined by the amount of the specific in-body resource without considering the other in-body resources. However, actually, an in-body resource that is depleted first changes depending on the situation, for example, muscle fatigue becomes dominant, or the stagnation of the supply of energy becomes dominant. Thus, commonly, each of the stamina amount and the stamina capacity is represented by a multi-dimensional vector that is based on the amounts of a plurality of in-body resources.

A remaining stamina amount is a stamina amount that can be consumed from a certain time point during running to the stamina depletion point.

A consumed stamina amount is a difference between the stamina amounts at a certain time point during running and another time point.

Stamina efficiency is a reciprocal of a consumed stamina amount per unit distance. Thus, as the stamina efficiency has a higher value, the running has a smaller consumed stamina amount and higher efficiency. On the other hand, as the stamina efficiency has a lower value, the running has a larger consumed stamina amount and lower efficiency.

A condition index is an index that represents a person's condition as a continuous numerical value and is used for determining a person's remaining stamina amount and stamina efficiency at a certain time point during running. The person's condition represents a person's physical and psychological state such as a physical condition, a mood, and the like.

A condition class is a discrete index representing a person's condition and, similarly to the condition index, is used for determining person's remaining stamina amount and stamina efficiency at a certain time point during running. For example, the condition class has discrete values such as "good", "bad", and "insufficient sleep".

A standard speed is a speed that is appropriate for a user to run a long distance, in other words, a speed at which a user can run comfortably when the user runs a long distance.

A standard heart rate is a heart rate when a user runs at the standard speed.

A sustainable heart rate is an upper limit value of the heart rate at which a user can continuously run a predetermined distance or a heart rate close to the upper limit value.

A cardiorespiratory limit speed is a speed at which a user can maintain the sustainable heart rate.

2. Person's Running Characteristic

Next, person's running characteristics to be applied to the present technology will be described with reference to FIGS. 1 to 6.

Figure 2:
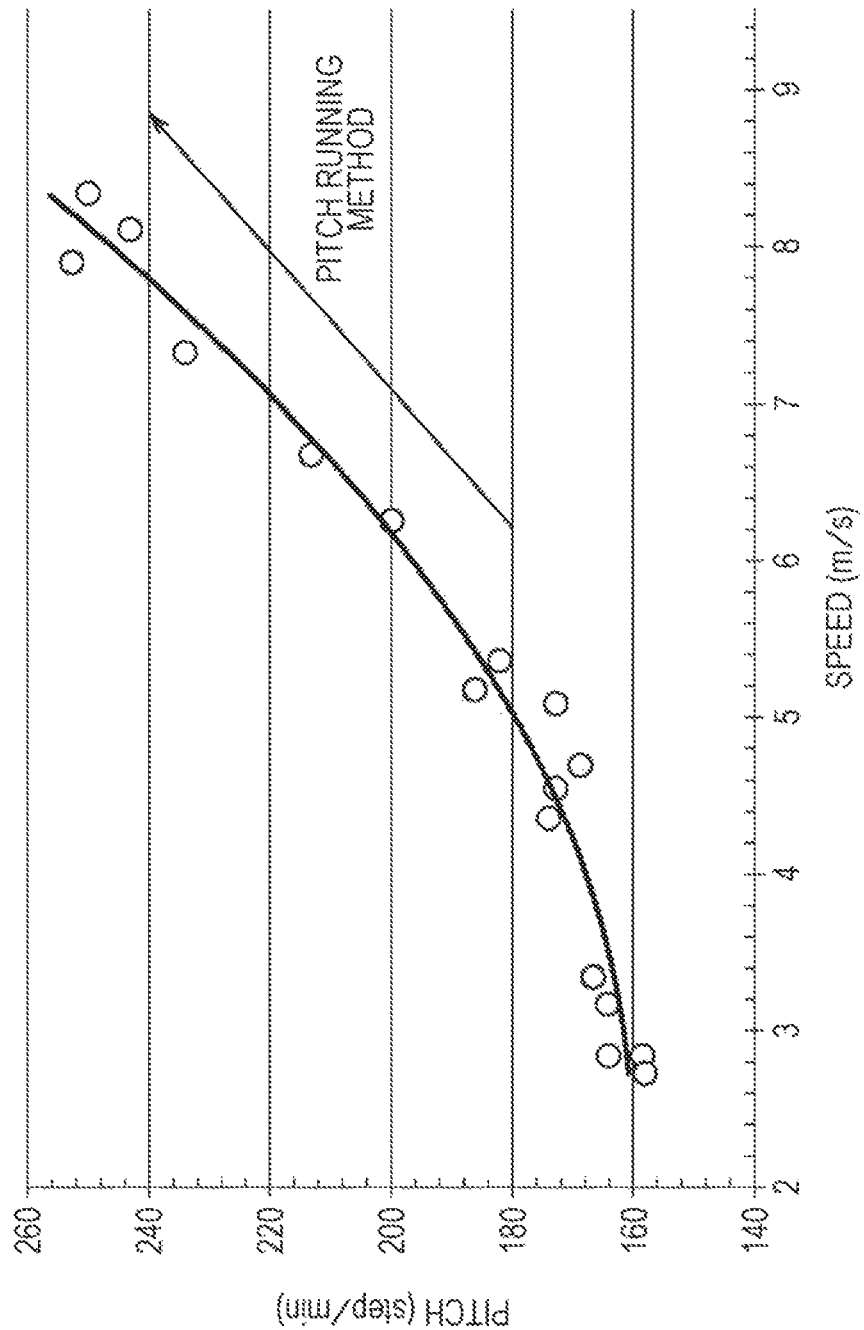
FIG. 2 is a graph that illustrates an example of a speed-pitch characteristic.
Figure 3:
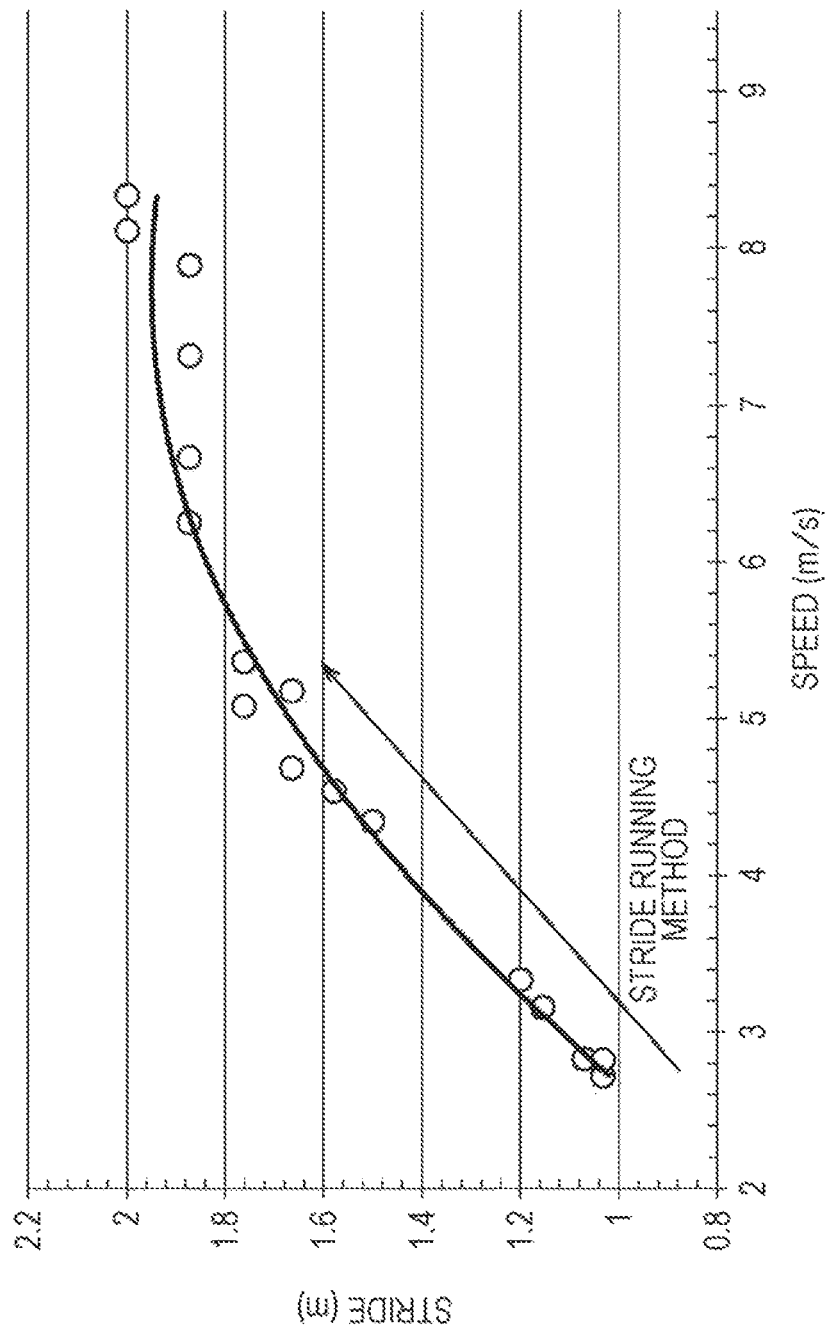
FIG. 3 is a graph that illustrates an example of a speed-stride characteristic.
Figure 4:
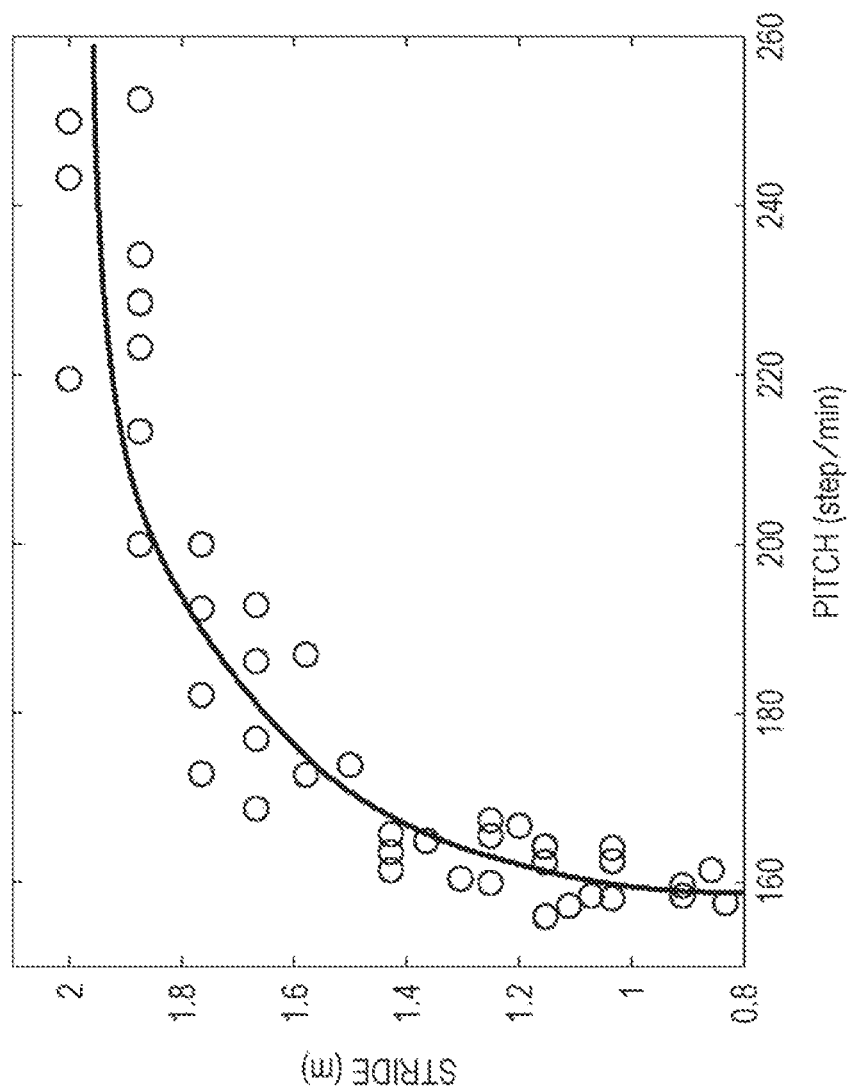
FIG. 4 is a graph that illustrates an example of a pitch-stride characteristic.

FIGS. 1 to 4 illustrate typical examples of person's running characteristics acquired through experiments. FIG. 1 is a three-dimensional graph that illustrates a relation among the speed, the pitch, and the stride (hereinafter, referred to as speed-pitch-stride characteristic) at the time of person's running. An axis of the horizontal direction (direction x) represents the speed, an axis of the depth direction (direction y) represents the stride, and an axis of the height direction (direction z) represents the pitch. FIG. 2 is a two-dimensional graph that illustrates a relation (hereinafter, referred to as a speed-pitch characteristic) between the speed and the pitch at the time of person's running. The horizontal axis represents the speed, and the vertical axis represents the pitch. FIG. 3 is a two-dimensional graph that illustrates a relation (hereinafter, referred to as a speed-stride characteristic) between the speed and the stride at the time of person's running. The horizontal axis represents the speed, and the vertical axis represents the stride. FIG. 4 is a two-dimensional graph that illustrates a relation (hereinafter, referred to as a pitch-stride characteristic) between the pitch and the stride at the time of person's running. The horizontal axis represents the pitch, and the vertical axis represents the stride.

As illustrated in FIGS. 1 to 4, it has been acquired that there are the following relations among the speed, the pitch, and the stride at the time of person's running through experiments.

As illustrated in FIG. 2, the pitch approximately monotonously increases with respect to the speed. In other words, basically, as the speed increases, the pitch increases as well. On the other hand, as the speed decreases, the pitch decreases as well.

As illustrated in FIG. 3, the stride approximately monotonously increases with respect to the speed. In other words, basically, as the speed increases, the stride increases as well. On the other hand, as the speed decreases, the stride decreases as well. However, for some persons, there are cases where a phenomenon in which the stride is slightly shortened at full-speed running is observed.

As illustrated in FIG. 4, the stride approximately monotonously increases with respect to the pitch. In other words, basically, as the pitch increases, the stride increases as well. On the other hand, as the pitch decreases, the stride decreases as well. However, for some persons, there are cases where a phenomenon in which the stride is slightly shortened in an area in which the pitch is the highest is observed.

As illustrated in FIG. 2, a change rate (hereinafter, referred to as a pitch change rate) of the pitch with respect to the speed greatly changes near a predetermined speed (hereinafter, referred to as a pitch switching speed) as a boundary. In other words, the pitch change rate is low in a range less than the pitch switching speed, and the pitch change rate is high in a range of the pitch switching speed or more. Accordingly, until the speed arrives at the pitch switching speed, growth of the pitch with respect to the speed is small, and, when the speed is the pitch switching speed or more, growth of the pitch with respect to the speed is large.

On the other hand, as illustrated in FIG. 3, a change rate (hereinafter, referred to as a stride change rate) of the stride with respect to the speed greatly changes near a predetermined speed (hereinafter, referred to as a stride switching speed) as a boundary. In other words, the stride change rate is high in a range less than the stride switching speed, and the stride change rate is low in a range of the stride switching speed or more. Accordingly, until the speed arrives at the stride switching speed, growth of the stride with respect to the speed is large, and, when the speed is the stride switching speed or more, growth of the stride with respect to the speed is small.

The pitch switching speed and the stride switching speed may have mutually-different values according to the definitions but have approximately same values for many persons when actually measured. Accordingly, it is understood that a person accelerates by mainly increasing the stride until arriving at a predetermined speed and, after arriving at the predetermined speed, accelerates by mainly raising the pitch. In other words, a person executes a stride running method accelerating by mainly increasing the stride until arriving at a predetermined speed and switches the running method to a pitch running method accelerating by mainly raising the pitch after arriving at the predetermined speed. In other words, a person executes the stride running method at the time of running slow and executes the pitch running method at the time of running fast.

In addition, each individual has a unique running characteristic. In other words, when a person runs, the person exhibits a running characteristic, which is unique to the person, having a high degree of reproduction in a short term. Meanwhile, there is an individual difference in the running characteristic.

More specifically, the running characteristic exhibits the following characteristics without depending on an individual difference. The pitch and the stride approximately monotonously increase with respect to the speed. The pitch change rate greatly changes near the pitch switching speed as a boundary. The pitch change rate is higher in a case where the speed is the pitch switching speed or higher than in a case where the speed is lower than the pitch switching speed.

The stride change rate greatly changes near the stride switching speed as a boundary. The stride change rate is higher in a case where the speed is lower than the stride switching speed than in a case where the speed is the stride switching speed or higher. In many persons, a difference between the pitch switching speed and the stride switching speed is small.

Meanwhile, there is an individual difference in the running characteristic due to differences of the following items.
Pitch switching speed
Stride switching speed
Pitch change rate
Stride change rate
Minimum value and maximum value of pitch
Minimum value and Maximum value of stride
Maximum value of speed In addition, the running characteristic of each individual changes according to elements such as training, a change in the physical constitution or the muscular strength, and aging. On the other hand, the running characteristic of each individual is estimated not to be influenced much by outdoor temperature, the humidity, or the altitude.

In this way, the running characteristic represents a combination of the pitch and the stride at each speed at the time of each individual's running. By acquiring each individual's running characteristic, based on one of the speed, the pitch, and the stride, the other two can be estimated almost accurately. For example, in a case where the speed during running is known, based on the graph illustrated in FIG. 1, the stride and the pitch for the speed can be estimated almost accurately.

On the other hand, in related art, since the presence of this running characteristic has not been recognized, in a case where two of the speed, the pitch, and the stride are not known, it is difficult to acquire the other one.

In addition, by comparing the running characteristic of each individual with the actually-measured values of the speed, the pitch, and the stride, the current running state of each individual can be estimated.

Figure 5:
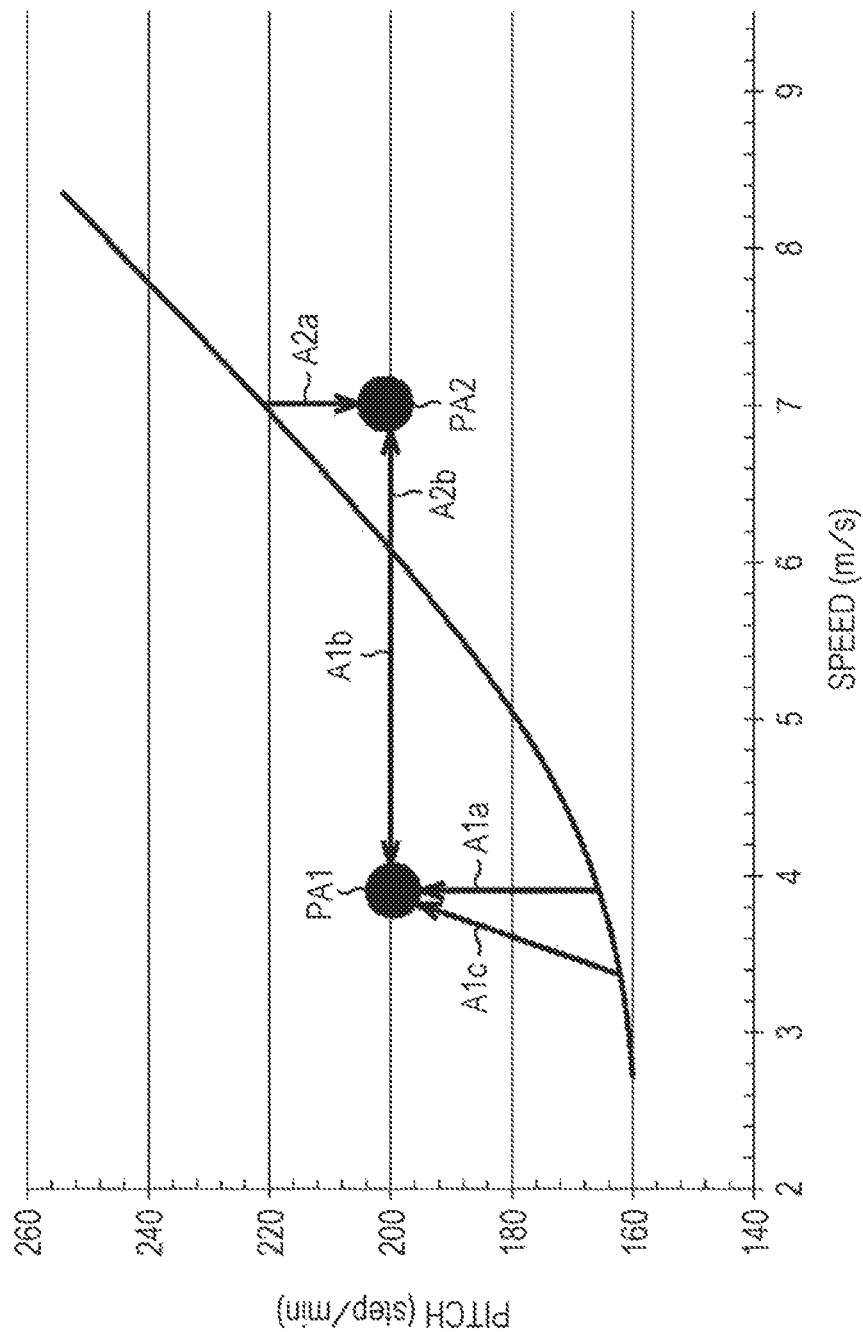
FIG. 5 is a diagram that illustrates an example of estimating the running state based on the running characteristic.
Figure 6:
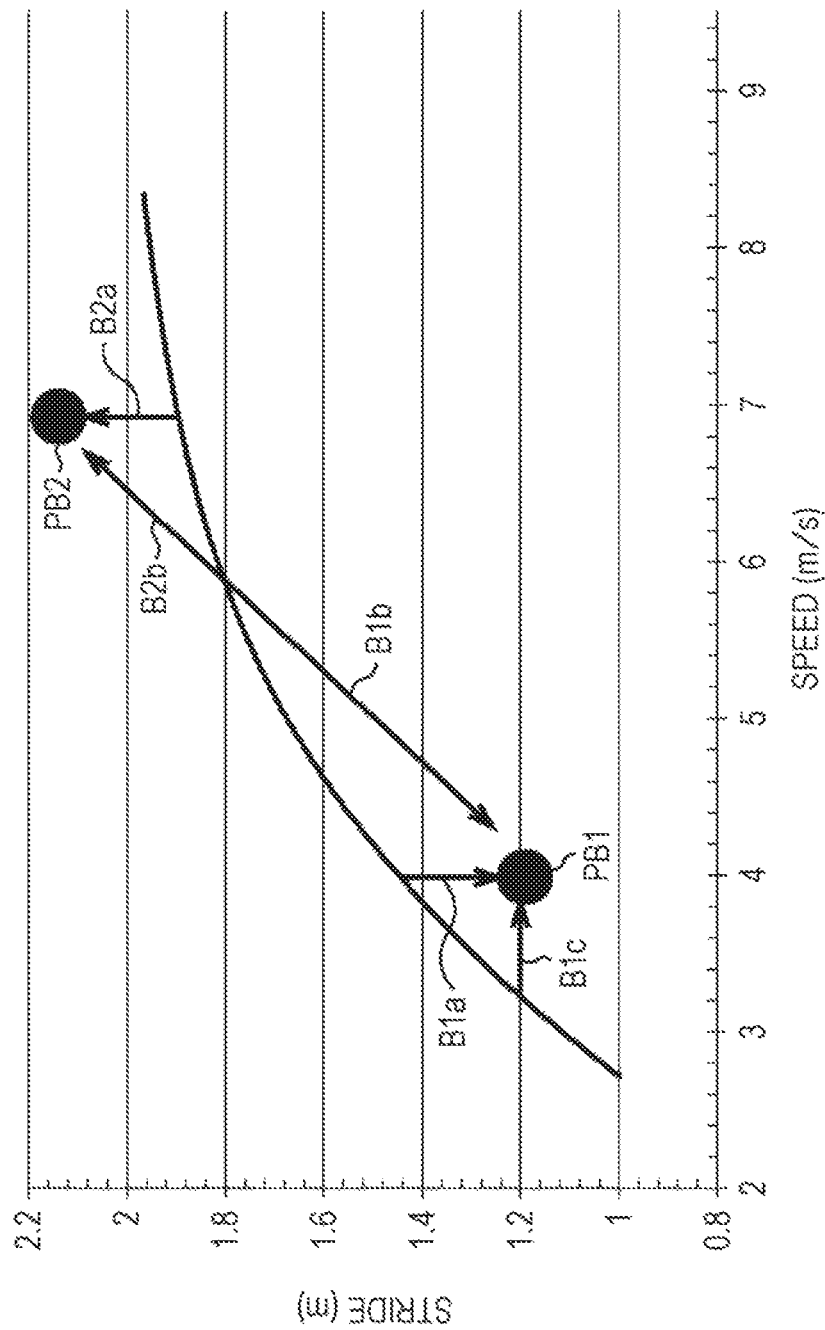
FIG. 6 is a diagram that illustrates an example of estimating the running state based on the running characteristic.

For example, FIGS. 5 and 6 illustrate an example of the running characteristic of a certain person. FIG. 5 illustrates the speed-pitch characteristic, and FIG. 6 illustrates the speed-stride characteristic.

For example, in a case where the actually-measured values of the speed, the pitch, and the stride are values represented at a point PA1 illustrated in FIG. 5 and a point PB1 illustrated in FIG. 6, the current running state can be perceived according to any of the following viewpoints.

For example, as denoted by an arrow A1a illustrated in FIG. 5 and an arrow B1a illustrated in FIG. 6, the current running state can be regarded such that, for the same speed, the pitch is higher than that of the running characteristic, and the stride is shorter than that of the running characteristic. Alternatively, as denoted by an arrow A1$b$ illustrated in FIG. 5 and an arrow B1$b$ illustrated in FIG. 6, the current running state can be regarded such that, for the same pitch, the stride is shorter than that of the running characteristic, and the speed is lower than that of the running characteristic. Alternatively, as denoted by an arrow A1$c$ illustrated in FIG. 5 and an arrow B1$c$ illustrated in FIG. 6, the current running state can be regarded such that, for the same stride, the pitch is higher than that of the running characteristic, and the speed is higher than that of the running characteristic. The various viewpoints as above can be summarized such that a point positioned on a further upper side than the speed/pitch characteristic curve, like the point PA1 illustrated in FIG. 5, represents that the pitch runs faster than that of the own running characteristic.

In addition, for example, in a case where the actually-measured values of the speed, the pitch, and the stride are values represented by a point PA2 illustrated in FIG. 5 and a point PB2 illustrated in FIG. 6, the current running state can be perceived according to the following viewpoints.

For example, as denoted by an arrow A2$a$ illustrated in FIG. 5 and an arrow B2$a$ illustrated in FIG. 6, the current running state can be regarded such that, for the same speed, the pitch is lower than that of the running characteristic, and the stride is longer than that of the running characteristic. Alternatively, as denoted by an arrow A2$b$ illustrated in FIG. 5 and an arrow B2$b$ illustrated in FIG. 6, the current running state can be regarded such that, for the same pitch, the stride is longer than that of the general running characteristic, and the speed is higher than that of the general running characteristic. The various viewpoints as above can be summarized such that a point positioned on a further lower side than the speed/pitch characteristic curve, like the point PA2 illustrated in FIG. 5, represents that the stride runs faster than that of the own running characteristic.

According to an embodiment of the present technology, by using the running characteristic described as above, analysis of the running state, the cardiorespiratory capacity, and the stamina characteristic, support of training, generation of a running plan, and the like are executed.

3. Embodiment of Present Technology

Next, an embodiment of the present technology will be described.
[Configuration Example of Information Processing System 101]

Figure 7:
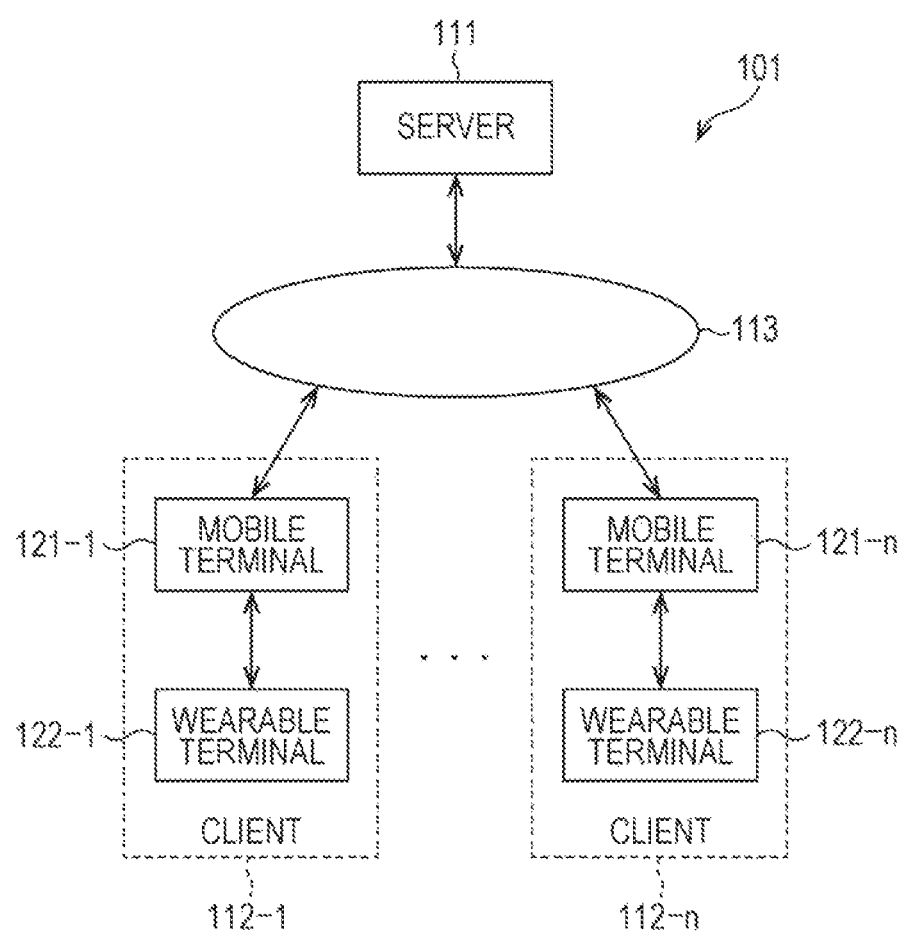
FIG. 7 is a block diagram that illustrates an information processing system according to an embodiment of the present technology.

FIG. 7 illustrates an example of the configuration of an information processing system 101 according to an embodiment of the present technology.

The information processing system 101 is a system that provides a running support service for a user. The running support service, for example, is a service performing analysis of a running characteristic, a running state, a cardiorespiratory capacity, and a stamina characteristic, support of training, generation of a running plan, and the like.

The information processing system 101 is configured to include a server 111, clients 112-1 to 112-$n$, and a network 113. Each client 112-$i$ (i=1 to n) is configured to include: a mobile terminal 121-$i$ (i=1 to n) and a wearable terminal 122-$i$ (i=1 to n).

The server 111 and the mobile terminals 121-1 to 121-$n$ are interconnected through a network 113. More accurately, while the server 111 and the mobile terminals 121-1 to 121-$n$ are respectively connected to the network 113 through a base station and the like (for example, a base station of a mobile telephone, an access point of a wireless LAN, or the like) not illustrated in the drawing, for the simplification of description, the base station and the like will not be described.

Hereinafter, in a case where it is not necessary to individually discriminate the clients 112-1 to 112-$n$, the mobile terminals 121-1 to 121-$n$, and the wearable terminals 122-1 to 122-$n$, they will be simply referred to as a client 112, a mobile terminal 121, and a wearable terminal 122.

The server 111, for example, is configured by a computer or the like. The server 111 is kept by a service provider and provides a running support service for each client 112. For example, the server 111 performs provision of an application program used for using a running support service, analysis of the running characteristic, the running state, the cardiorespiratory capacity, and the stamina characteristic of each user, provision of a training menu and a running plan, and the like.

Each client 112 is held by each user using the running support service, and each user uses the running support service through the client 112.

The mobile terminal 121, for example, is configured by a device that can be carried by a user during running such as a smartphone, a mobile telephone, a mobile information terminal, or the like.

The wearable terminal 122 is configured by a device that can be worn by a user during running. As the wearable terminal 122, for example, any one of wearable devices of various types such as a glass type, a wrist watch type, a bracelet type, a necklace type, a neck band type, an earphone type, a headset type, a head mounting type, a bandana type, and a hairband type may be employed.

The mobile terminal 121 and the wearable terminal 122 perform near field communication according to a predetermined system.
[Configuration Example of Server 111]

Next, an example of the configuration of the server 111 will be described with reference to FIGS. 8 and 9.

Figure 8:
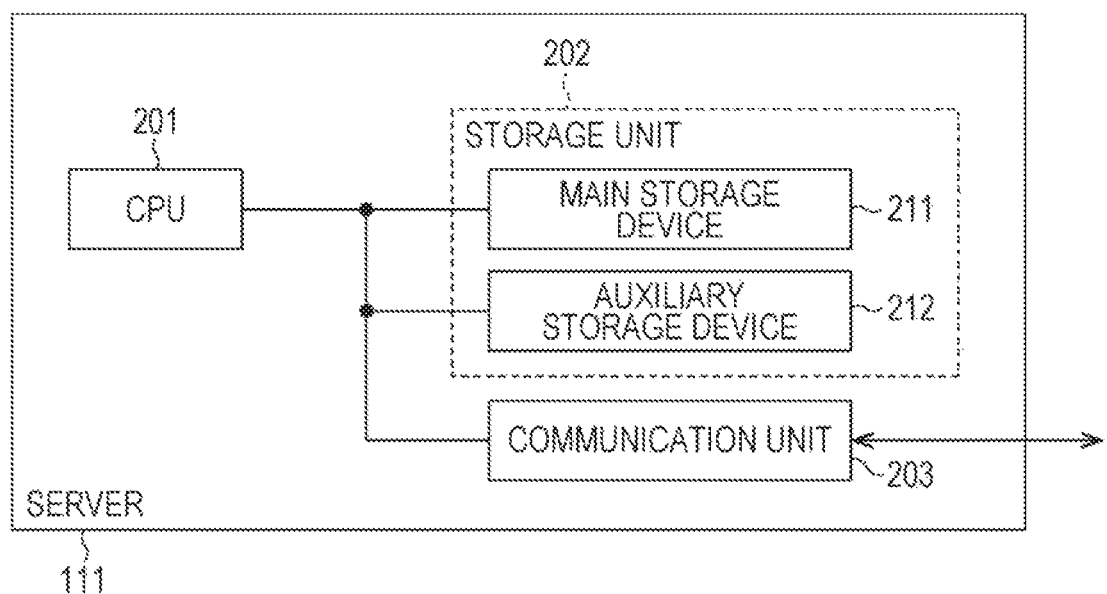
FIG. 8 is a block diagram that illustrates an example of the configuration of a server.

FIG. 8 illustrates an example of the configuration of the server 111.

The server 111 is configured by: a Central Processing Unit (CPU) 201; a storage unit 202; and a communication unit 203. The storage unit 202 is configured to include a main storage device 211 and an auxiliary storage device 212.

The main storage device 211, for example, is configured by a Read Only Memory (ROM), a Random Access Memory (RAM) or the like.

The auxiliary storage device 212, for example, is configured by a hard disk drive, a flash memory, or the like. In addition, the auxiliary storage device 212, for example, is configured by a removable medium such as a magnetic disk, an optical disc, a magneto-optical disk, or a semiconductor memory, a drive that drives the removable medium, and the like.

The communication unit 203, for example, is configured by a network interface and the like. The communication unit 203 communicates according to a predetermined system with a base station not illustrated in the drawing and communicates with each mobile terminal 121 through the communication station and the network 113. As the communication system of the communication unit 203, an arbitrary system may be employed regardless of a wired system or a wireless system. However, it is desirable to employ a communication system of which the operation is stable so as to provide a stable service to the client 112.

Figure 9:
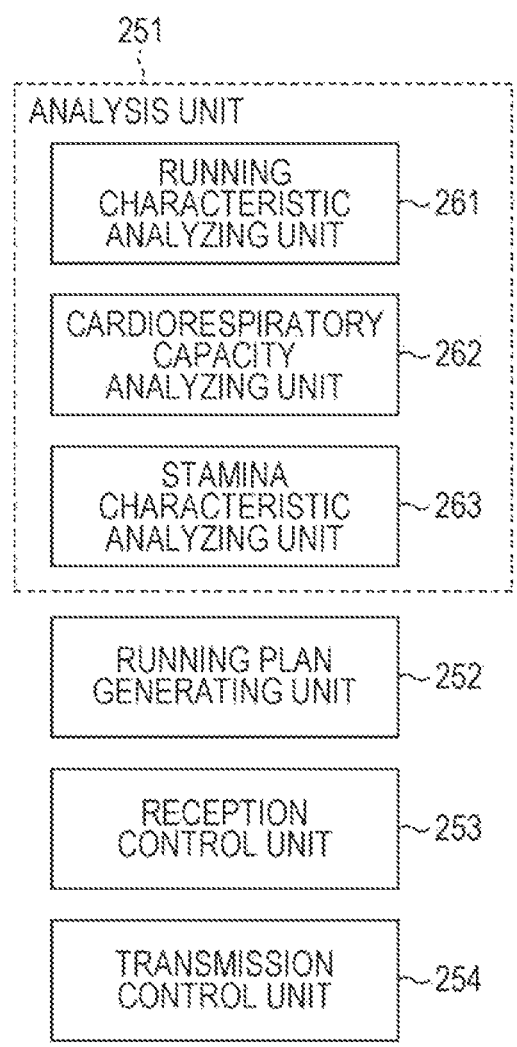
FIG. 9 is a block diagram that illustrates an example of the configuration of functions realized by a CPU of the server.

FIG. 9 illustrates an example of the configuration of functions realized by a CPU 201 of the server 111 executing a predetermined program. As the CPU 201 executes a predetermined program, functions including an analysis unit 251, a running plan generating unit 252, a reception control unit 253, and a transmission control unit 254 are realized. The analysis unit 251 is configured to include: a running characteristic analyzing unit 261; a cardiorespiratory capacity analyzing unit 262; and a stamina characteristic analyzing unit 263.

The running characteristic analyzing unit 261, based on measurement results such as the speed, the pitch, the stride, the heart rate, and the like of each user acquired from each client 112, analyzes the running characteristic of each user. The running characteristic analyzing unit 261 stores a result of the analysis of the running characteristic of each user in the storage unit 202. In addition, the running characteristic analyzing unit 261 generates feedback information toward each user based on the result of the analysis of the running characteristic. Then, the running characteristic analyzing unit 261 transmits the generated feedback information to each client 112 through the transmission control unit 254, the communication unit 203, and the network 113.

The cardiorespiratory capacity analyzing unit 262 analyzes the cardiorespiratory capacity of each user based on the running characteristic of each user and the results of measurements of the speed, the pitch, the stride, the heart rate, and the like of each user acquired from each client 112. The cardiorespiratory capacity analyzing unit 262 stores a result of the analysis of the cardiorespiratory capacity of each user in the storage unit 202. In addition, the cardiorespiratory capacity analyzing unit 262 generates feedback information toward each user based on the result of the analysis of the cardiorespiratory capacity. Then, the cardiorespiratory capacity analyzing unit 262 transmits the generated feedback information to each client 112 through the transmission control unit 254, the communication unit 203, and the network 113.

The stamina characteristic analyzing unit 263 analyzes the stamina characteristic of each user based on the running characteristic and the cardiorespiratory capacity of each user and the results of measurements of the speed, the pitch, the stride, the heart rate, and the like of each user acquired from each client 112. The stamina characteristic analyzing unit 263 stores a result of the analysis of the stamina characteristic of each user in the storage unit 202. In addition, the stamina characteristic analyzing unit 263 generates feedback information toward each user based on the result of the analysis of the stamina characteristic. Then, the stamina characteristic analyzing unit 263 transmits the generated feedback information to each client 112 through the transmission control unit 254, the communication unit 203, and the network 113.

The running plan generating unit 252 generates and updates a running plan of a course run by each user based on the running characteristic, the cardiorespiratory capacity, and the stamina characteristic of each user and results of measurements of the speed, the pitch, the stride, the heart rate, and the like acquired from each client 112. Then, the running plan generating unit 252 transmits the running plan that has been generated or updated to each client 112 through the transmission control unit 254, the communication unit 203, and the network 113.

The reception control unit 253 controls reception of data and information transmitted from each mobile terminal 121 through the network 113 that is executed by the communication unit 203. In addition, the reception control unit 253, as is necessary, supplies the received data or information to each unit of the server 111 or stores the received data or information in the storage unit 202.

The transmission control unit 254 controls the transmission of data or information to each mobile terminal 121 that is executed by the communication unit 203.

While each unit of the server 111 communicates with each client 112 through the reception control unit 253 or the transmission control unit 254, the communication unit 203, and the network 113, hereinafter, for the simplification of description, basically, description of "through the reception control unit 253 or the transmission control unit 254, the communication unit 203, and the network 113" will not be presented.

{Configuration Example of Mobile Terminal 121}

Next, an example of the configuration of the mobile terminal 121 will be described with reference to FIGS. 10 and 11.

Figure 10:
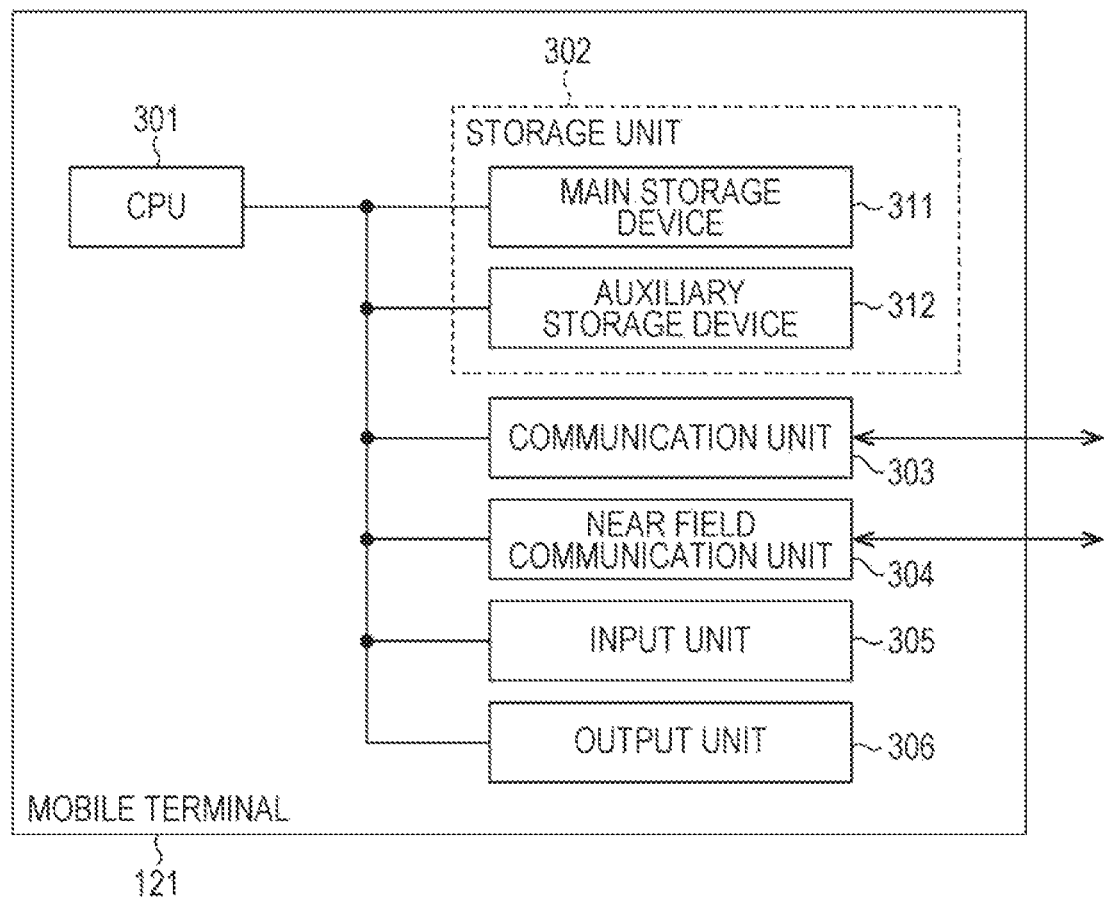
FIG. 10 is a block diagram that illustrates an example of the configuration of a mobile terminal.

FIG. 10 illustrates the example of the mobile terminal 121.

The mobile terminal 121 is configured to include: a CPU 301; a storage unit 302; a communication unit 303; a near field communication unit 304; an input unit 305; and an output unit 306. The storage unit 302 is configured to include: a main storage device 311; and an auxiliary storage device 312.

The main storage device 311, for example, is configured by a ROM, a RAM, and the like.

The auxiliary storage device 312, for example, is configured by a hard disk drive, a flash memory, or the like. In addition, the auxiliary storage device 312, for example, is configured by a removable medium such as a magnetic disk, an optical disc, a magneto-optical disk, or a semiconductor memory, a drive that drives the removable medium, and the like.

The communication unit 303 communicates according to a predetermined system in a wireless manner with a base station not illustrated in the drawing and communicates with the server 111 through the communication station and the network 113. As the communication system of the communication unit 303, an arbitrary system may be employed. In addition, the communication unit 303 may be configured to also perform wired communication.

The near field communication unit 304 performs near field communication according to a predetermined system with the wearable terminal 122. As the communication system of the near field communication unit 304, an arbitrary system may be employed, and, for example, Bluetooth (registered trademark), infrared communication, or the like is employed.

The input unit 305 is used for inputting an instruction, data, a voice command, or the like to the mobile terminal 121. For example, the input unit 305 is configured by various operation devices (for example, a touch panel, a button, a switch, a key, a keyboard, and the like), a microphone, an image sensor, and the like.

The output unit 306, for example, is configured by a display, a speaker, a video output terminal, an audio output terminal, and the like and outputs various kinds of information using an image, an audio, or the like.

Figure 11:
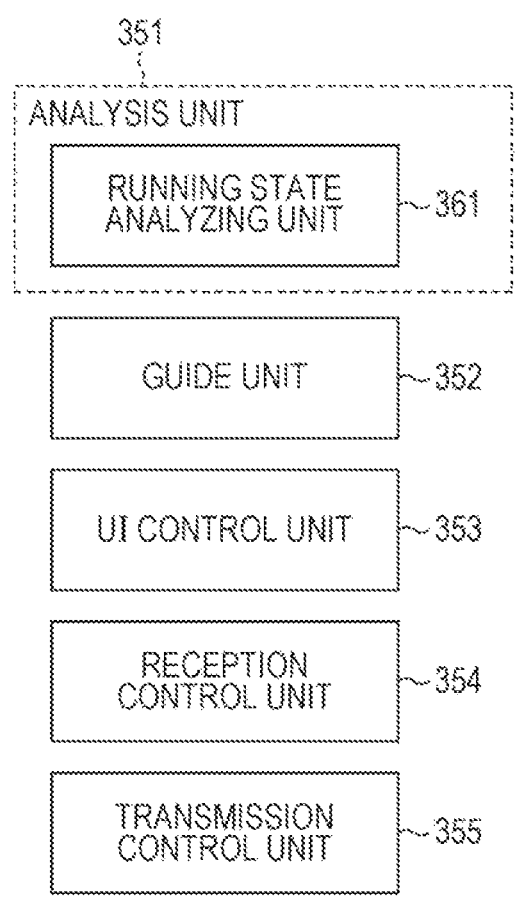
FIG. 11 is a block diagram that illustrates an example of the configuration of functions realized by a CPU of the mobile terminal.

FIG. 11 illustrates an example of the configuration of functions realized by a CPU 301 of the mobile terminal 121 executing a predetermined program.

As the CPU 301 executes a predetermined program, an analysis unit 351, a guide unit 352, a user interface (UI) control unit 353, a reception control unit 354, and a transmission control unit 355 are configured to be included. The analysis unit 351 is configured to include a running state analyzing unit 361.

The running state analyzing unit 361 analyzes the running state of a user based on the running characteristic, the cardiorespiratory capacity, and the stamina characteristic of the user and various kinds of measurement data acquired from the wearable terminal 122. The running state analyzing unit 361 stores the measurement data acquired from the wearable terminal 122, a result of the analysis of the running state, and the like in the storage unit 302 or transmits the data and the result to the server 111 through the transmission control unit 355, the communication unit 303, and the network 113.

The guide unit 352 communicates with the wearable terminal 122 through the reception control unit 354 or the transmission control unit 355 and the near field communication unit 403 and guides the speed, the pitch, and the stride of a user through the wearable terminal 122 by using sensing information and the like of the user acquired by the wearable terminal 122.

The UI control unit 353 controls input, output, presentation, and the like of data and information that are executed by the input unit 305 and the output unit 306. In addition, the UI control unit 353, as is necessary, supplies input data and information to each unit of the mobile terminal 121 or stores the input data and information in the storage unit 302.

The reception control unit 354 controls reception of data or information transmitted from the server 111 through the network 113 that is executed by the communication unit 303. In addition, the reception control unit 354 controls reception of data or information transmitted from the wearable terminal 122 that is executed by the near field communication unit 304. Furthermore, the reception control unit 354, as is necessary, supplies received data or information to each unit of the mobile terminal 121 or stores the received data or information in the storage unit 302.

The transmission control unit 355 controls transmission of data or information to the server 111 that is executed by the communication unit 303. In addition, the transmission control unit 355 controls transmission of data or information to the wearable terminal 122 that is executed by the near field communication unit 304.

While each unit of the mobile terminal 121 communicates with the server 111 through the reception control unit 354 or the transmission control unit 355, the communication unit 303, and the network 113, hereinafter, for the simplification of description, basically, description of "through the reception control unit 354 or the transmission control unit 355, the communication unit 303, and the network 113" will not be presented. In addition, while each unit of the mobile terminal 121 communicates with the wearable terminal 122 through the reception control unit 354 or the transmission control unit 355 and the near field communication unit 304, hereinafter, for the simplification of description, basically, description of "through the reception control unit 354 or the transmission control unit 355 and the near field communication unit 304" will not be presented. Furthermore, while the output unit 306 of the mobile terminal 121 outputs various kinds of information under the control of the UI control unit 353, hereinafter, for the simplification of description, basically, description of "under the control of the UI control unit 353" will not be presented.

{Configuration Example of Wearable Terminal 122}

Next, an example of the configuration of the wearable terminal 122 will be described with reference to FIGS. 12 to 15.

Figure 12:
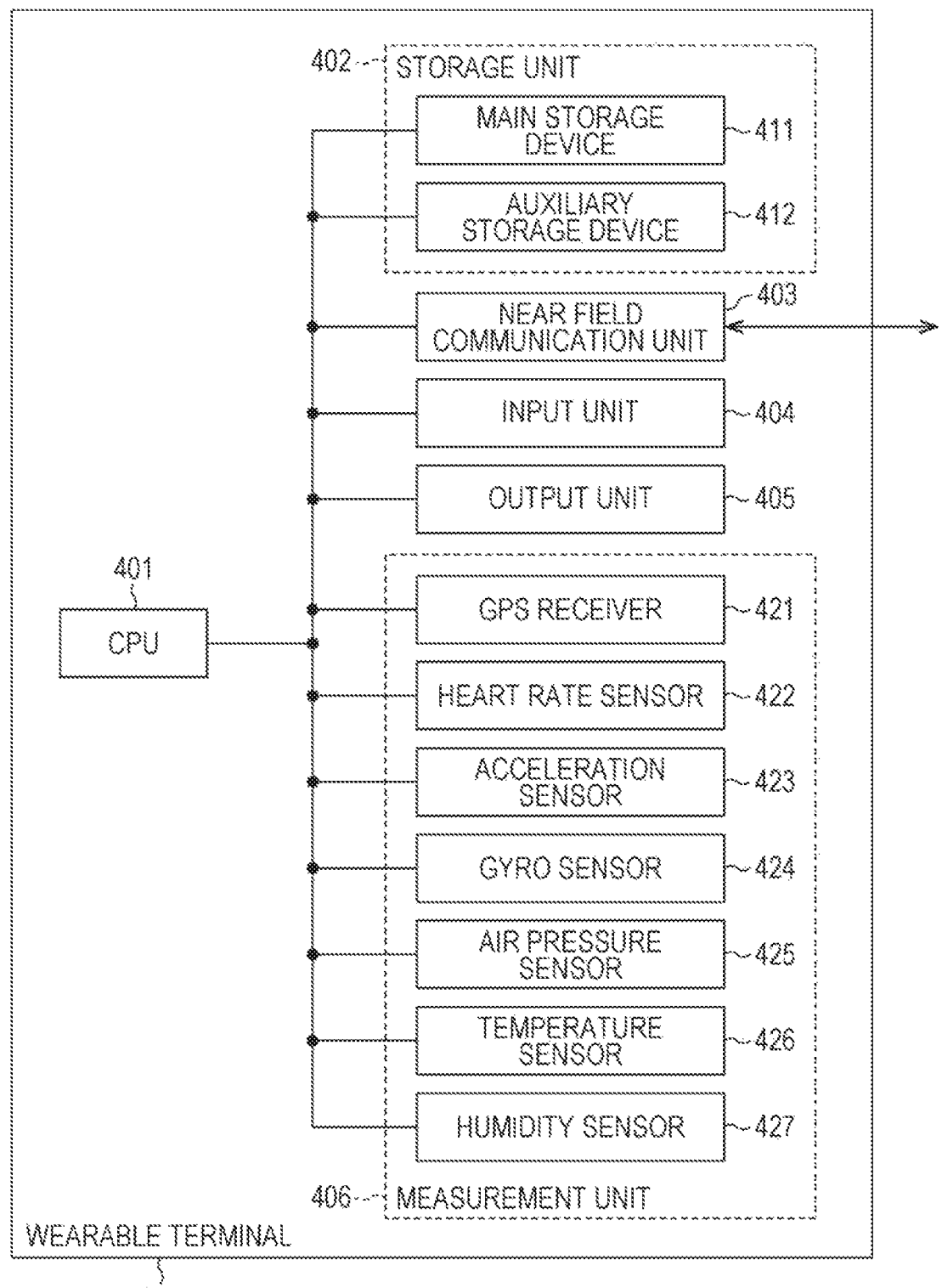
FIG. 12 is a block diagram that illustrates an example of the configuration of a wearable terminal.

FIG. 12 illustrates an example of the configuration of the wearable terminal 122.

The wearable terminal 122 is configured to include: a CPU 401; a storage unit 402; a near field communication unit 403; an input unit 404; an output unit 405; and a measurement unit 406. The storage unit 402 is configured to include a main storage device 411 and an auxiliary storage device 412. The measurement unit 406 is configured to include: a Global Positioning System (GPS) receiver 421; a heart rate sensor 422; an acceleration sensor 423; a gyro sensor 424; an air pressure sensor 425; a temperature sensor 426; and a humidity sensor 427. The sensing information and the like of a user are acquired by this measurement unit 406.

The main storage device 411, for example, is configured by a ROM, a RAM or the like.

The auxiliary storage device 412, for example, is configured by a hard disk drive, a flash memory, or the like. In addition, the auxiliary storage device 412, for example, is configured by a removable medium such as a magnetic disk, an optical disc, a magneto-optical disk, or a semiconductor memory, a drive that drives the removable medium, and the like.

The near field communication unit 403 communicates with the near field communication unit 304 in accordance with a system similar to that of the near field communication unit 304 of the mobile terminal 121.

The input unit 404 is used for inputting an instruction, data, a voice command, or the like to wearable terminal 122. For example, the input unit 404 is configured by various operation devices (for example, a touch panel, a button, a switch, a key, a keyboard, and the like), a microphone, an image sensor, and the like.

The output unit 405, for example, is configured by a display, a speaker, an earphone, a light emitting device, a vibration module, and the like. Alternatively, for example, the output unit 405 is configured by a video output terminal, an audio output terminal, and the like. The output unit 405 outputs various kinds of information, for example, using an image, an audio, light, a vibration, or the like.

Figure 13:
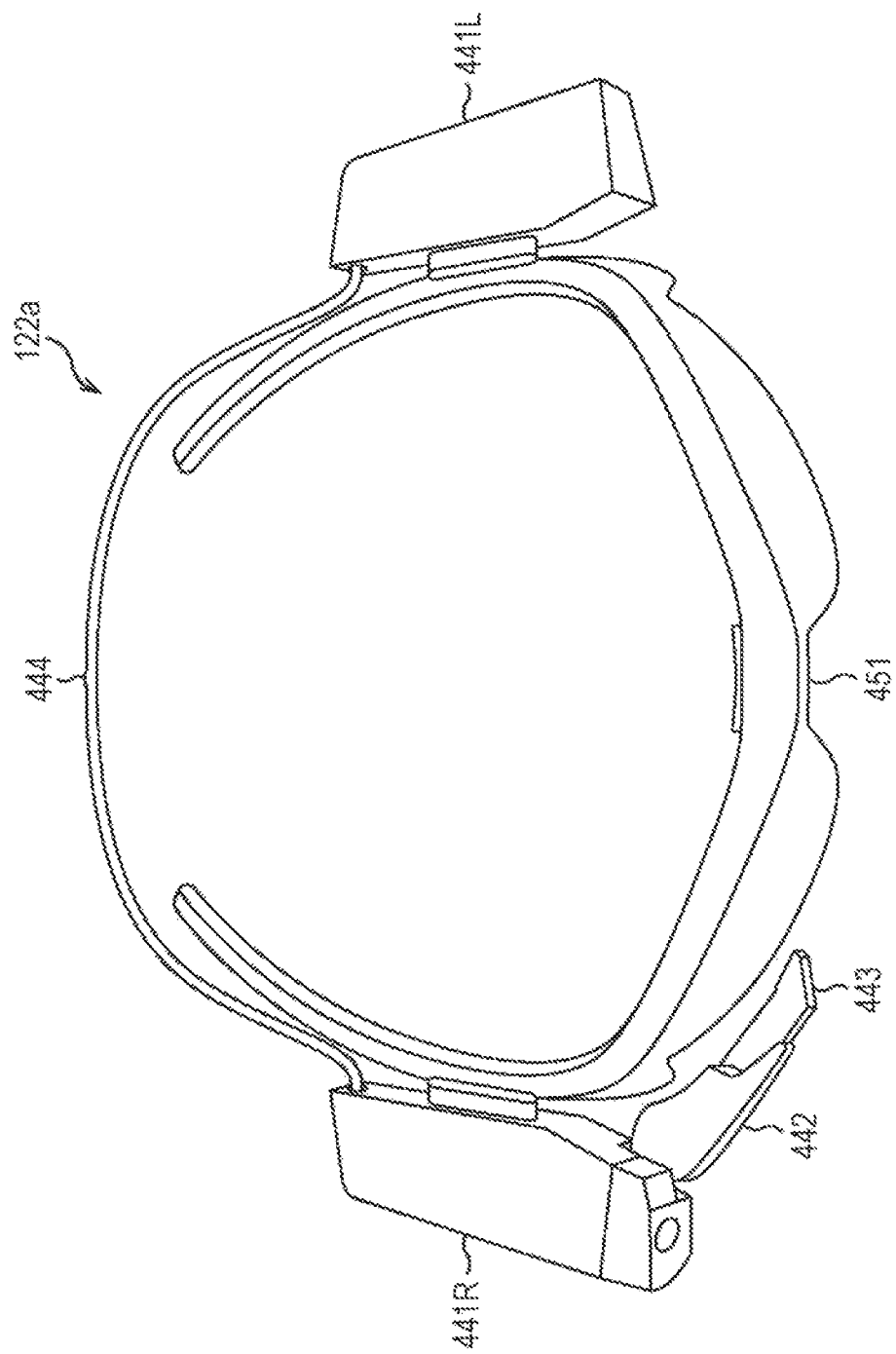
FIG. 13 is an external configuration diagram that illustrates a first example of the wearable terminal.

FIG. 13 illustrates an example of the configuration of the external view of a wearable terminal 122a that is a first example of the wearable terminal 122.

The wearable terminal 122a is used with being mounted to eyewear 451 such as glasses, sunglasses, or goggles. The wearable terminal 122a is configured to include: left and right main body units 441L and 441R; a display 442; an optical unit 443; and a neck band 444. The main body unit 441L and the main body unit 441R are connected to each other through the neck band 444.

In the main body units 441L and 441R, for example, at least some of the CPU 401, the main storage device 411, the auxiliary storage device 412, the near field communication unit 403, the input unit 404, the output unit 405, and the measurement unit 406 illustrated in FIG. 12 are stored.

The display 442 and the optical unit 443 are included in the output unit 405 illustrated in FIG. 12. The display 442, for example, is configured by a display such as an organic Electro Luminescence (EL) display. The optical unit 443, for example, is configured by a lens or the like. A user can view an image displayed on the display 442 by using the right eye through the optical unit 443 while viewing the surrounding in a state in which the eyewear 451 is mounted.

Figure 14:
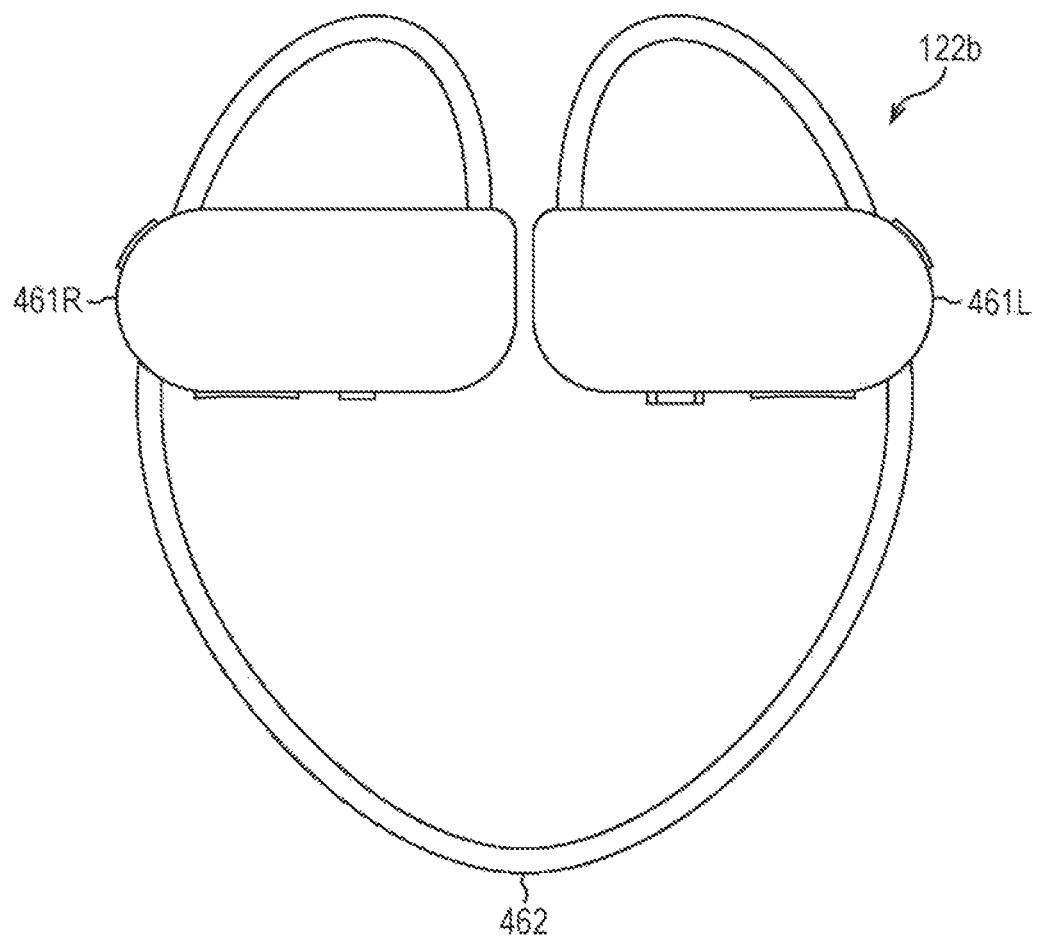
FIG. 14 is an external configuration diagram that illustrates a second example of the wearable terminal.

FIG. 14 illustrates an example of the configuration of the external view of a wearable terminal 122b that is a second example of the wearable terminal 122.

The wearable terminal 122b is a wearable terminal of a neck band type and is configured to include: left and right main body units 461L and 461R; and a neck band 462. The main body unit 461L and the main body unit 461R are connected to each other through the neck band 462.

In the main body units 461L and 461R, for example, at least some of the CPU 401, the main storage device 411, the auxiliary storage device 412, the near field communication unit 403, the input unit 404, the output unit 405, and the measurement unit 406 illustrated in FIG. 12 are stored.

A user, for example, mounts an earphone (not illustrated in the drawing) disposed in the main body units 461L and 461R on both ears and can hear voice information through the mounted earphone.

Figure 15:
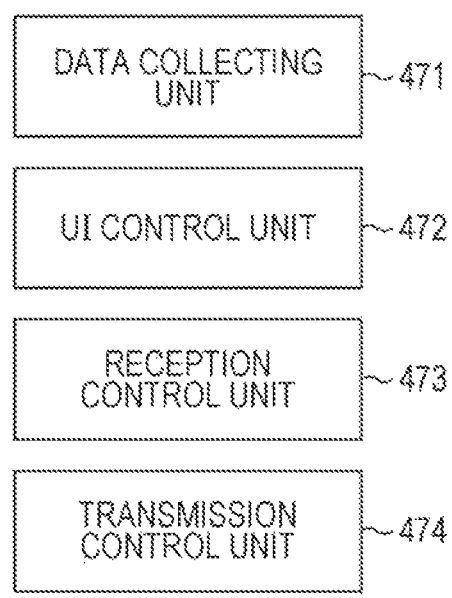
FIG. 15 is a block diagram that illustrates an example of the configuration of functions realized by a CPU of the wearable terminal.

FIG. 15 illustrates an example of the configuration of functions realized by the CPU 401 of the wearable terminal 122 executing a predetermined program.

As the CPU 401 executes a predetermined program, a data collecting unit 471; a UI control unit 472, a reception control unit 473, and a transmission control unit 474 are configured to be included.

The data collecting unit 471 collects measurement data output from each device of the measurement unit 406 and transmits the collected measurement data to the mobile terminal 121 through the transmission control unit 474 and the near field communication unit 403.

The UI control unit 472 controls input, output, presentation, and the like of data and information that are executed by the input unit 404 and the output unit 405. In addition, the UI control unit 472, as is necessary, supplies input data and information to each unit of the wearable terminal 122 or stores the input data and information in the storage unit 402.

The reception control unit 473 controls reception of data and information transmitted from the mobile terminal 121 that is executed by the near field communication unit 403. The reception control unit 473, as is necessary, supplies received data or information to each unit of the wearable terminal 122 or stores the received data or information in the storage unit 402.

The transmission control unit 355 controls transmission of data and information from the near field communication unit 403 to the mobile terminal 121.

While each unit of the wearable terminal 122 communicates with the mobile terminal 121 through the reception control unit 473 or the transmission control unit 474, and the near field communication unit 403, hereinafter, for the simplification of description, basically, description of "through the reception control unit 473 or the transmission control unit 474 and the near field communication unit 403" will not be presented. In addition, while the output unit 405 of the wearable terminal 122 outputs various kinds of information under the control of the UI control unit 472, hereinafter, for the simplification of description, basically, description of "under the control of the UI control unit 472" will not be presented.

{Process of Information Processing System 101}

Next, the process of the information processing system 101 will be described.

(Running Characteristic Analyzing Process)

First, a running characteristic analyzing process executed by the information processing system 101 will be described with reference to a flowchart illustrated in FIG. 16. For example, this process is started when a user (hereinafter, referred to as a target user in this process) who is a target for analyzing the running characteristic inputs an instruction for executing the running characteristic analyzing process to the mobile terminal 121 or the wearable terminal 122.

In step S1, the client 112 takes measurement at low-speed running. For example, the guide unit 352 of the mobile terminal 121 notifies the wearable terminal 122 of the start of the running characteristic analyzing process. The output unit 405 of the wearable terminal 122, for example, outputs a voice message of "Your running pattern is to be analyzed. Running is measured at three steps".

Next, the guide unit 352 of the mobile terminal 121 instructs the wearable terminal 122 to take measure at the time of low-speed running. The output unit 405 of the wearable terminal 122, for example, outputs a voice message of "First, please take slow jogging", thereby urging the target user to perform low-speed running. Accordingly, the target user performs a stride running method at a speed lower than the stride switching speed. The data collecting unit 471 of the wearable terminal 122 collects measurement data output from each device of the measurement unit 406 and transmits the collected measurement data to the mobile terminal 121.

The running state analyzing unit 361 of the mobile terminal 121 measures the speed, the pitch and the stride of the target user at the time of low-speed running based on the received measurement data. As methods of measuring the speed, the pitch, and the stride, while arbitrary methods may be employed, hereinafter, an example of the measurement methods will be described.

For example, the running state analyzing unit 361 measures a necessary time between two points separated from each other based on the measurement data acquired by the GPS receiver 421 and divides a distance between the two points by the necessary time, thereby measuring the speed of the target user. Alternatively, the running state analyzing unit 361 integrates the measurement data acquired by the acceleration sensor 423, thereby measuring the speed of the target user. Alternatively, the running state analyzing unit 361 calibrates a speed measured by using another method based on a change pattern of the measurement data acquired by the acceleration sensor 423, thereby measuring the speed of the target user.

In addition, for example, the running state analyzing unit 361 analyzes a change pattern of the measurement data acquired by the acceleration sensor 423, thereby estimating the pitch of the target user. Then, the running state analyzing unit 361 divides the speed measured using the method described above by the pitch estimated as above, thereby calculating the stride of the target user.

Alternatively, for example, the running state analyzing unit 361 sets an estimated stride acquired by dividing an actually-measured value of the speed by the estimated pitch as teacher data and performs machine learning by using a characteristic amount of the waveform acquired by the acceleration sensor 423 as input data. Then, the running state analyzing unit 361 estimates a stride based on the characteristic amount of the waveform acquired by the acceleration sensor 423 by using a result of the machine learning. In this way, since the stride is estimated based on not a physical quantity but a habit of the running method, the estimation accuracy of the stride does not decrease even when the accuracy of the acceleration sensor 423 is low. In addition, since the estimation is based on a habit of the running method, for example, as a parameter used for estimating a remaining stamina amount to be described later, the estimated stride is superior to an actual stride. Furthermore, for example, by making a correction of a learning result based on the remaining stamina amount, a condition index, and the like, the estimation accuracy of the stride can be further improved.

Thereafter, the guide unit 352 notifies the wearable terminal 122 of the completion of the measurement at the low-speed running. The output unit 405 of the wearable terminal 122 outputs a voice message of "The analysis of jogging has been completed".

In step S2, the client 112 takes measurement at the time of standard-speed running. For example, the output unit 405 of the wearable terminal 122 outputs a voice message of "Please run at a pace for running in the best condition for the time being!", thereby urging the target user to perform standard-speed running. The speed of the target user at the standard-speed running is closer to the stride switching speed and the pitch switching speed than that at the time of jogging. Then, by executing a process similar to that at the time of low-speed running, the measurement data is collected, and the speed, the pitch, and the stride of the target user at the time of standard-speed running are measured. Thereafter, the guide unit 352 of the mobile terminal 121 notifies the wearable terminal 122 of the completion of the measurement at the time of standard-speed running. The output unit 405 of the wearable terminal 122, for example, outputs a voice message of "The analysis of pleasant running has been completed".

In step S3, the client 112 takes measurement at the time of high-speed running. For example, the output unit 405 of the wearable terminal 122 outputs a voice message of "At last, please run about 100 m at full-speed with considering it as a last spurt", thereby urging the target user to perform high-speed running. Accordingly, the target user performs a pitch running method at a speed higher than the pitch switching speed. Then, by executing a process similar to those at the time of low-speed running and at the time of standard-speed running, the measurement data is collected, and the speed, the pitch, and the stride of the target user at the time of high-speed running are measured.

In step S4, the client 112 transmits results of the measurements and the like. For example, the running state analyzing unit 361 of the mobile terminal 121 transmits the measurement results of the speeds, the pitches, the strides, and the heart rates of the target user at the time of low-speed running, at the time of standard-speed running, and at the time of high-speed running, environment information at the time of measurements, and user information to the wearable terminal 122. In the environment information at the time of measurements, for example, measurement date and time, outdoor temperature, and the like are included. In the user information, for example, ID information used for identifying a target user and information of age, sex, a physical constitution (height, weight, and the like), and the like are included. The user information, for example, is input to the target user in advance.

In step S5, the reception control unit 253 of the server 111 receives the measurement results and the like transmitted from the client 112 and stores the received measurement results and the like in the storage unit 202.

In step S6, the running characteristic analyzing unit 261 of the server 111 analyzes the running characteristic.

For example, the running characteristic analyzing unit 261 analyzes the speed-pitch-stride characteristics of a plurality of users in advance and classifies the patterns (the positions, the shapes, and the like) of speed-pitch-stride characteristic curves into a plurality of clusters. Then, the running characteristic analyzing unit 261 estimates a cluster to which the speed-pitch-stride characteristic curve of the target user belongs based on the measurement results of the speed, the pitch, and the stride of the target user at the time of low-speed running, at the time of standard-speed running, and at the time of high-speed running. For example, the running characteristic analyzing unit 261 estimates a cluster for which a distance between the speed-pitch-stride characteristic curve of the cluster and measured values of the speed, the pitch, and the stride at the time of low-speed running, at the time of standard-speed running, and at the time of high-speed running is minimal as a cluster to which the speed-pitch-stride characteristic curve of the target user belongs.

Then, the running characteristic analyzing unit 261 performs fitting of the speed-pitch-stride characteristic curve of the cluster to which the target user is estimated to belong to the measurement values of the speed, the pitch, and the stride of the target user at the time of low-speed running, at the time of standard-speed running, and at the time of high-speed running. Accordingly, the speed-pitch-stride characteristic curve of the target user is generated.

By using a similar method, two or more of the speed-pitch characteristic curve, the speed-stride characteristic curve, and the pitch-stride characteristic curve may be configured to be generated.

Hereinafter, the speed-pitch-stride characteristic curve, the speed-pitch characteristic curve, the speed-stride characteristic curve, and the pitch-stride characteristic curve will be collectively referred to as running characteristic curves.

Then, the running characteristic analyzing unit 261 repeats the fitting process using the collected measurement data as the measurement data of the speed, the pitch, and the stride of the target user increases and updates the running characteristic curve of the target user, thereby increasing the accuracy.

The running characteristic analyzing unit 261, for example, may be configured to generate a running characteristic curve of the target user based on only the measurement data of the speed, the pitch, and the stride of the target user without using the clustering technique. Alternatively, the running characteristic analyzing unit 261 may appropriately execute switching between a case where the clustering technique is used and a case where only the measurement data of the target user is used. Alternatively, the running characteristic analyzing unit 261 may be configured to generate a final running characteristic curve by composing running characteristic curves generated using both the techniques using predetermined weighting factors.

In addition, the running characteristic analyzing unit 261 may be configured to analyze the running characteristic in consideration of the influence of running environments. For example, the running characteristic analyzing unit 261 generates a running characteristic curve by adding the condition of a road surface, which is one type of environment information, to a parameter. Alternatively, the running characteristic analyzing unit 261, for example, may be configured to divide the condition of a road surface into a plurality of ranges and generate running characteristic curves that are different for the ranges. Accordingly, the accuracy of the running characteristic curve is improved. In the condition of the road surface, for example, an inclination angle, a material (for example, asphalt, stone pavement, soil, or the like) of the road surface, a wet/dry state, and the like are included. The condition of the road surface may be acquired or estimated based on map information, weather data, a user input, or the like.

In addition, the running characteristic analyzing unit 261 may be configured to classify the condition of a target user into a plurality of classes based on a condition index or a condition class of the target user and generate a running characteristic curve for each of the classes.

Furthermore, the running characteristic analyzing unit 261 detects the pitch switching speed and the stride switching speed of the target user.

Figure 17:
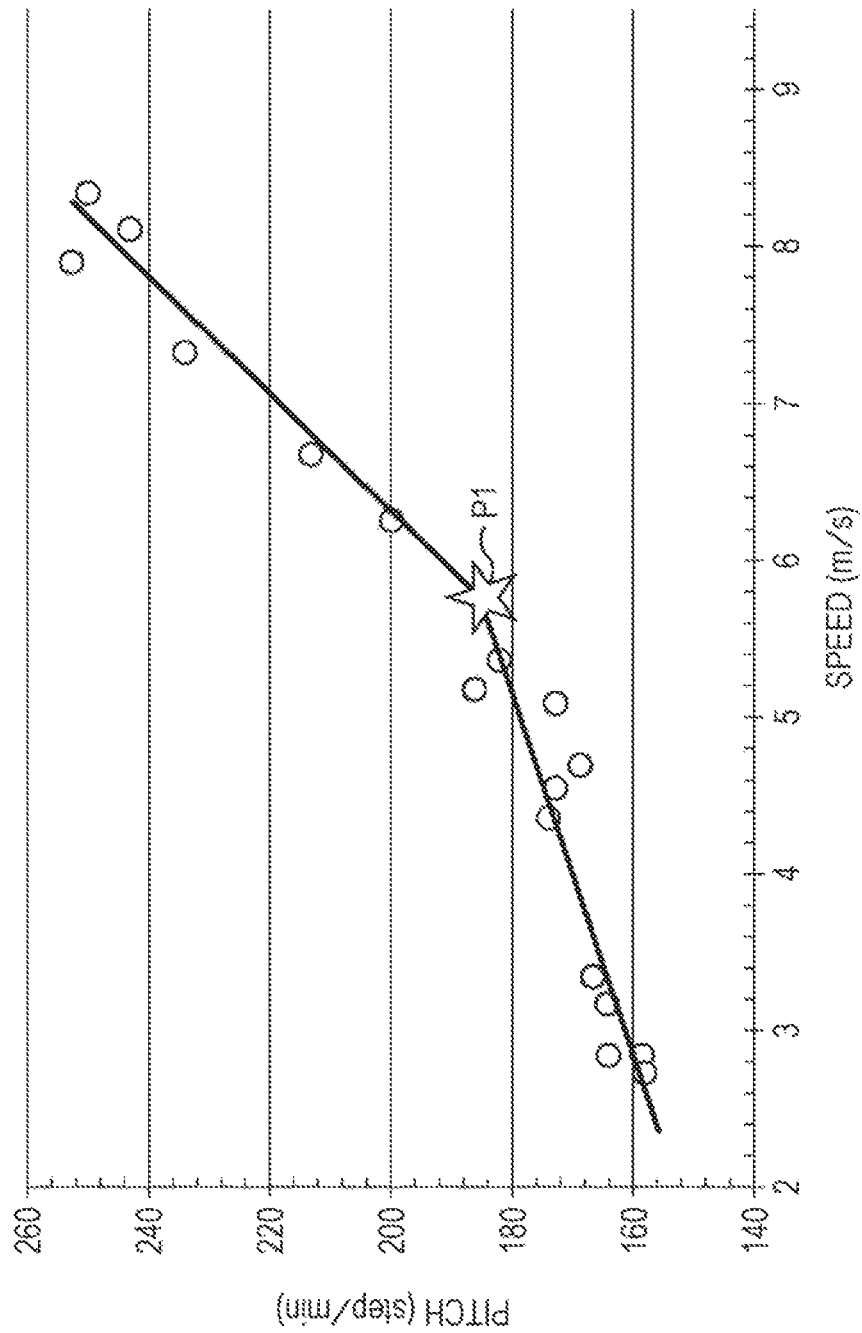
FIG. 17 is a diagram that illustrates a method of detecting a pitch switching speed.

FIG. 17 illustrates an example of the distribution of measurement data of the speed and the pitch of a target user. The horizontal axis is the speed, and the vertical axis is the pitch. For example, the running characteristic analyzing unit 261, while moving a junction P1 in the direction of the horizontal axis (speed), individually performs fitting of a straight line or a curved line in an area in which the speed is lower than that at the junction P1 and a straight line or a curved line in an area in which the speed is higher than that at the junction P1. Then, the running characteristic analyzing unit 261 sets the speed at the junction P1 at which an error from a measured value is minimal as the pitch switching speed of the target user.

Figure 18:
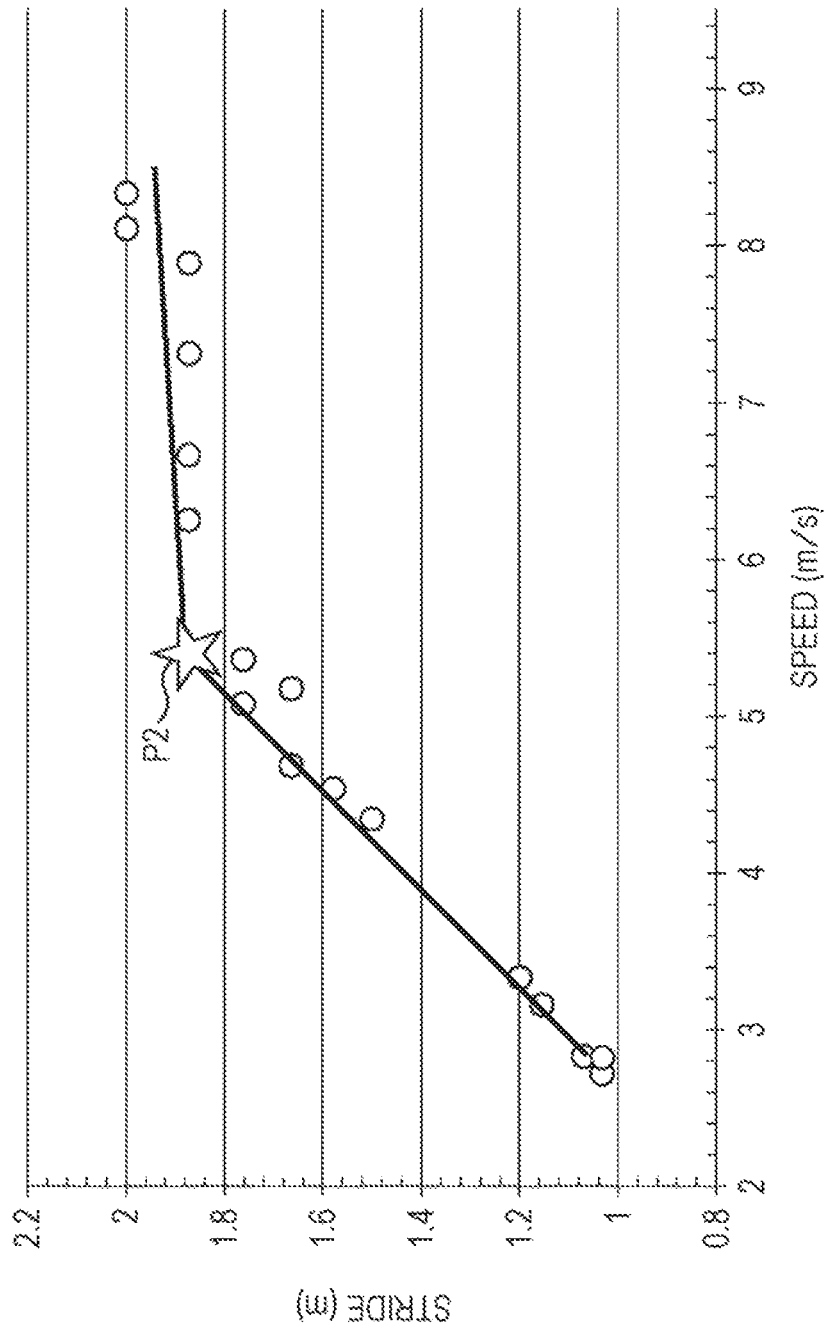
FIG. 18 is a diagram that illustrates a method of detecting a stride switching speed.

FIG. 18 illustrates an example of the distribution of measurement data of the speed and the stride of a target user. The horizontal axis is the speed, and the vertical axis is the stride. For example, the running characteristic analyzing unit 261, while moving a junction P2 in the direction of the horizontal axis (speed), individually performs fitting of a straight line or a curved line in an area in which the speed is lower than that at the junction P2 and a straight line or a curved line in an area in which the speed is higher than that at the junction P2. Then, the running characteristic analyzing unit 261 sets the speed at the junction P2 at which an error from a measured value is minimal as the stride switching speed of the target user.

In addition, the running characteristic analyzing unit 261 sets a stride-pitch switching speed of the target user based on the pitch switching speed and the stride switching speed. Here, the stride-pitch switching speed is an estimated speed at which the target user performs switching between a stride running method and a pitch running method. In a case where the running of the target user is guided, at the stride-pitch switching speed, switching between guided methods is performed.

For example, in a case where the pitch switching speed and the stride switching speed coincide with each other, the running characteristic analyzing unit 261 sets the coinciding speed as the stride-pitch switching speed. On the other hand, in a case where the pitch switching speed and the stride switching speed do not coincide with each other, for example, the running characteristic analyzing unit 261 sets any one of the speeds as the stride-pitch switching speed or sets an intermediate speed between the pitch switching speed and the stride switching speed as the stride-pitch switching speed. Alternatively, an area interposed therebetween is set as a switching area.

The running characteristic analyzing unit 261 stores a result of the analysis of the running characteristic of the target user in the storage unit 202.

In step S7, the running characteristic analyzing unit 261 generates feedback information. For example, the running characteristic analyzing unit 261 generates feedback information including the result of the analysis of the running characteristic of the target user and a message toward the target user. The message toward the target user, for example, includes description of the result of the analysis of the running characteristic, an advice for the target user that is based on the running characteristic, and the like.

In step S8, the running characteristic analyzing unit 261 of the server 111 transmits the feedback information to the mobile terminal 121 of the target user and, the process executed by the server 111 ends.

In step S9, the UI control unit 353 of the mobile terminal 121 receives the feedback information transmitted from the server 111.

Figure 19:
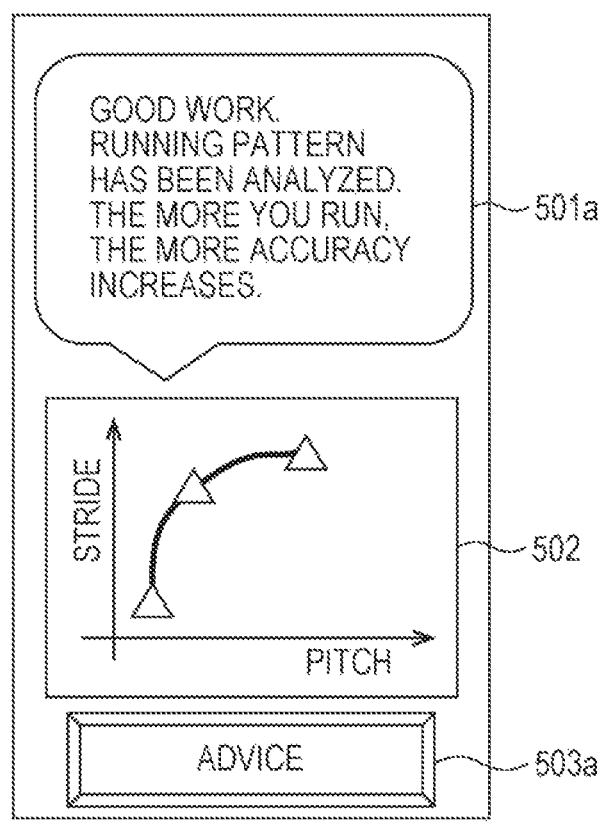
FIG. 19 is a diagram that illustrates a first example of a screen presenting an analysis result of a running characteristic.

In step S10, the client 112 presents the feedback information, and the process executed by the client 112 ends. For example, the output unit 306 of the mobile terminal 121 displays a screen illustrated in FIG. 19, thereby presenting the feedback information to the target user. On the screen illustrated in FIG. 19, a balloon 501a, a graph 502, and a button 503a are displayed.

Inside the balloon 501a, a message for a target user is displayed. In this example, a message conveying that the accuracy of the analysis of the running characteristic is improved as running is repeated is included.

The graph 502 is the pitch-stride characteristic curve of the target user acquired by the running characteristic analyzing process. The output unit 306 may be configured to display a running characteristic curve of another type.

Figure 20:
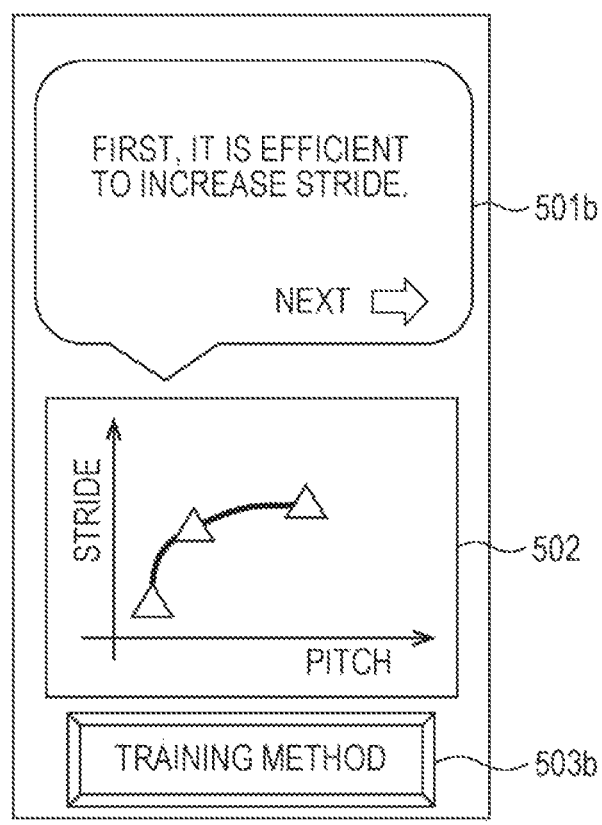
FIG. 20 is a diagram that illustrates a second example of a screen presenting an analysis result of a running characteristic.
Figure 21:
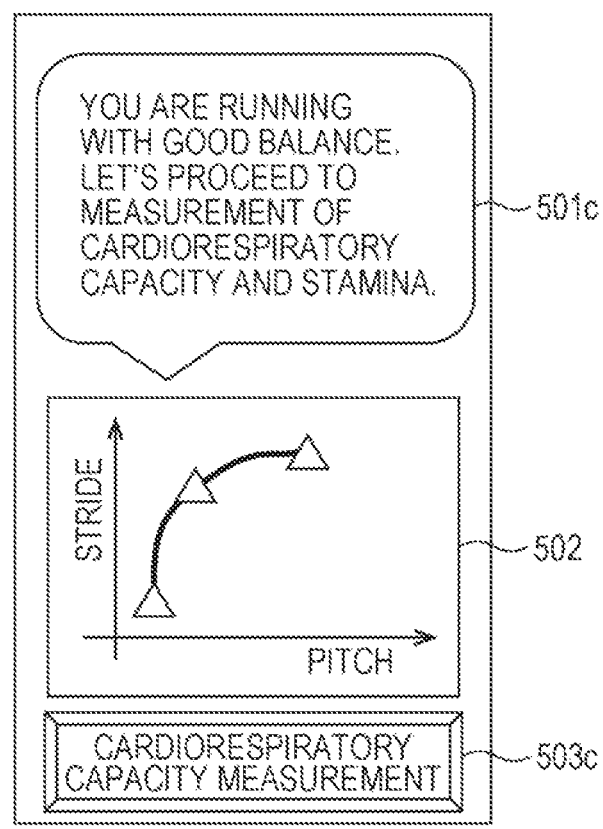
FIG. 21 is a diagram that illustrates a third example of a screen presenting an analysis result of a running characteristic.

When the button 503a is pressed, an advice for the target user is displayed. FIGS. 20 and 21 illustrate examples of screens that are displayed when the button 503a is pressed.

On the screens illustrated in FIGS. 20 and 21, balloons 501b and 501c are respectively displayed instead of the balloon 501a, and buttons 503b and 503c are respectively displayed instead of the button 503a. The graph 502 is continuously displayed as it is. The screen illustrated in FIG. 21 is for the user who is the same as that of the screen illustrated in FIG. 19, and the screen illustrated in FIG. 20 is for a user different from that of the screen illustrated in FIG. 19.

In each of the balloons 501b and 501c, for example, the current state of the target user, an advice for the target user, or the like is displayed. For example, in the balloon 501b, an advice for the target user is displayed. The content of the advice is changed based on the running characteristic of the target user. For example, in this example, a message recommending to increase the stride first is displayed. Alternatively, for example, a message urging the target user to find out a pace at which the user can run a predetermined distance (for example, 1 km) may be displayed. In the balloon 501c, an evaluation of the running of the target user is displayed. In addition, a message urging the target user to take the next measurement of the cardiorespiratory capacity and the stamina characteristic is displayed.

When the button 503b is pressed, for example, a training method for realizing the advice presented inside the balloon 511 is displayed.

Figure 22:
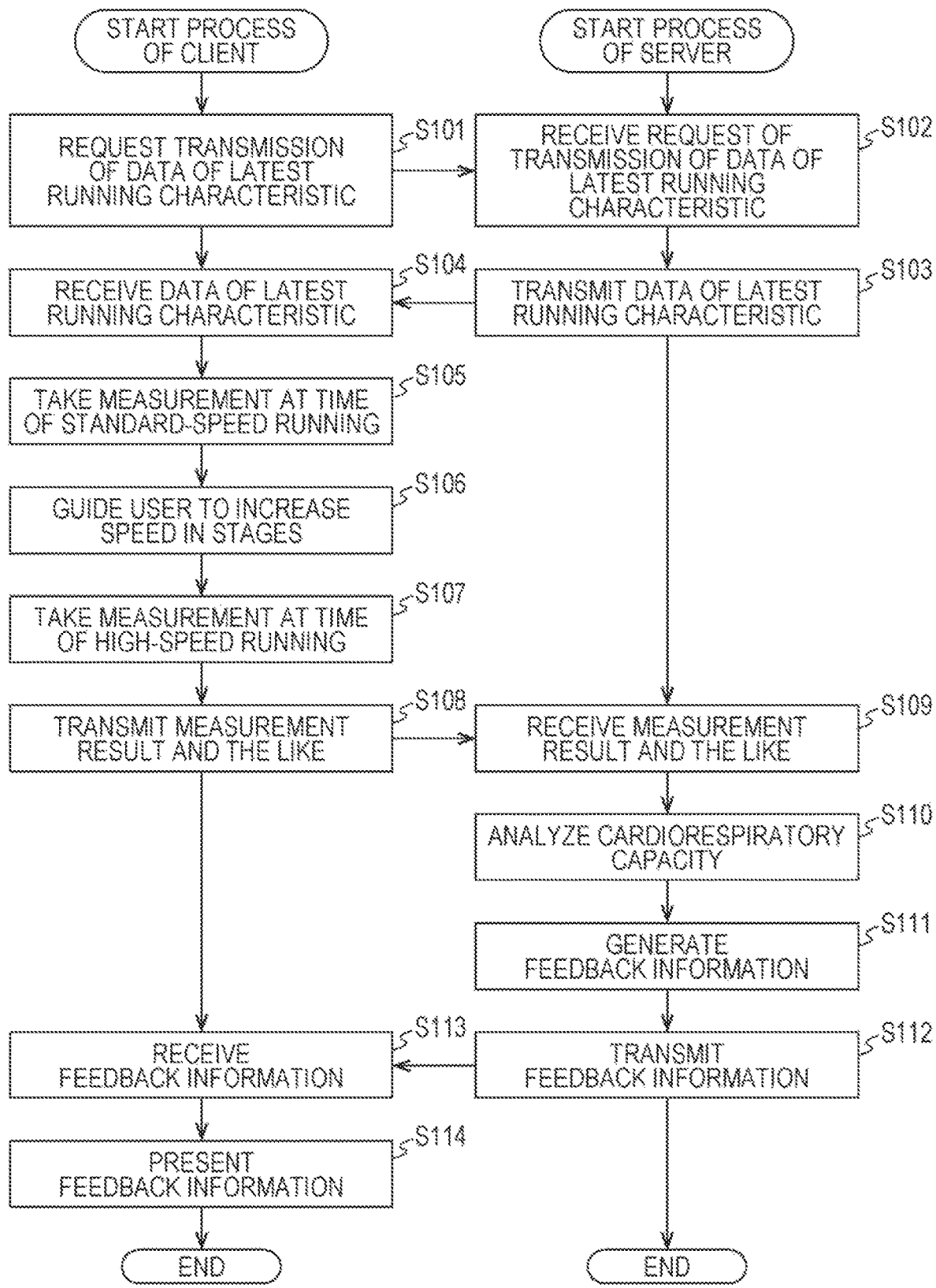
FIG. 22 is a flowchart that illustrates a cardiorespiratory capacity analyzing process executed by an information processing system.

When the button 503c is pressed, for example, the measurement of a cardiorespiratory capacity to be described later with reference to FIG. 22 can be taken.

In this way described above, the running characteristic of the target user can be analyzed. In addition, by performing an analysis by using the knowledge relating to the running characteristic of a person described above with reference to FIGS. 1 to 4, the running characteristic of a target user can be accurately analyzed using a small amount of measurement data. In addition, by clustering the running characteristics of a plurality of users and performing an analysis based on the running characteristic of a cluster to which a target user belongs, the running characteristic of the target user can be accurately analyzed only by measuring the speeds, the pitches, and the strides at the time of low-speed running, at the time of standard-speed running, and at the time of high-speed running.

Accordingly, immediately after the start of use of a running support service, the target user can acquire his running characteristic and can receive an appropriate advice according to the running characteristic. In this way, the target user can be prevented from being tired of the service, and the target user's motivation can be raised.

In addition, since the running characteristic is updated according to the accumulation of measurement data, even when the running characteristic is changed according to training or the like, the target user can constantly receive an advice appropriate for his running characteristic and perform appropriate training.

(Cardiorespiratory Capacity Analyzing Process)

Next, a cardiorespiratory capacity analyzing process executed by the information processing system 101 will be described with reference to a flowchart illustrated in FIG. 22. For example, this process is started when a user (hereinafter, referred to as a target user in this process) who is a target for the analysis of the cardiorespiratory capacity inputs an instruction for executing the cardiorespiratory capacity analyzing process to the mobile terminal 121 or the wearable terminal 122.

In step S101, the guide unit 352 of the mobile terminal 121 requests the server 111 to transmit data of the latest running characteristic of the target user.

In step S102, the running characteristic analyzing unit 261 of the server 111 receives the request for the transmission of data of the latest running characteristic of the target user.

In step S103, the running characteristic analyzing unit 261 of the server 111 reads the data of the latest running characteristic of the target user from the storage unit 202 and transmits the read data to the mobile terminal 121 of the target user.

In step S104, the guide unit 352 of the mobile terminal 121 receives the data of the latest running characteristic of the target user that is transmitted from the server 111.

In step S105, the client 112 performs measurement at the time of standard-speed running. For example, the guide unit 352 of the mobile terminal 121 notifies the wearable terminal 122 of the start of the cardiorespiratory capacity analyzing process. The output unit 405 of the wearable terminal 122, for example, outputs a voice message of "Your cardiorespiratory capacity is analyzed".

Next, the guide unit 352 of the mobile terminal 121 instructs the wearable terminal 122 to perform measurement of the target user at the time of standard-speed running. The output unit 405 of the wearable terminal 122, for example, outputs a voice message of "First, please run at a pace for the best condition", thereby urging the target user to run at a standard speed. Then, similarly to the process of step S2 illustrated in FIG. 16 described above, measurement at the time of standard-speed running is performed.

In step S106, the guide unit 352 of the mobile terminal 121 guides the target user to raise the speed through the wearable terminal 122. For example, the output unit 405 of the wearable terminal 122, first, outputs a voice message of "Please run according to an instruction of a heard sound. If you feel that it is too hard, please knock on the device".

Then, the guide unit 352 guides the target user to raise the speed in stages by using a voice through the output unit 405 of the wearable terminal 122. In addition, while guiding the target user, the client 112 continues to measure the speed, the pitch, the stride, the heart rate, and the like.

In step S107, the client 112 performs measurement at the time of high-speed running. For example, in a case where the target user feels it painful to further raise the speed, the target user inputs an instruction for stopping the guidance to the mobile terminal 121 or the wearable terminal 122. At this time point, the heart rate of the target user is raised to a state that is considerably close to the limit. Then, similarly to the process of step S3 illustrated in FIG. 16 described above, measurement at the time of high-speed running is performed.

In steps S106 and S107, the upper limit value of the heart rate may be set so as not to excessively raise the heart rate of the target user, for example, in correspondence with the age and the like of the target user. Then, in a case where the heart rate of the target user arrives at the upper limit value, the client 112 may be configured to guide the target user to stop the process or lower the speed.

Figure 16:
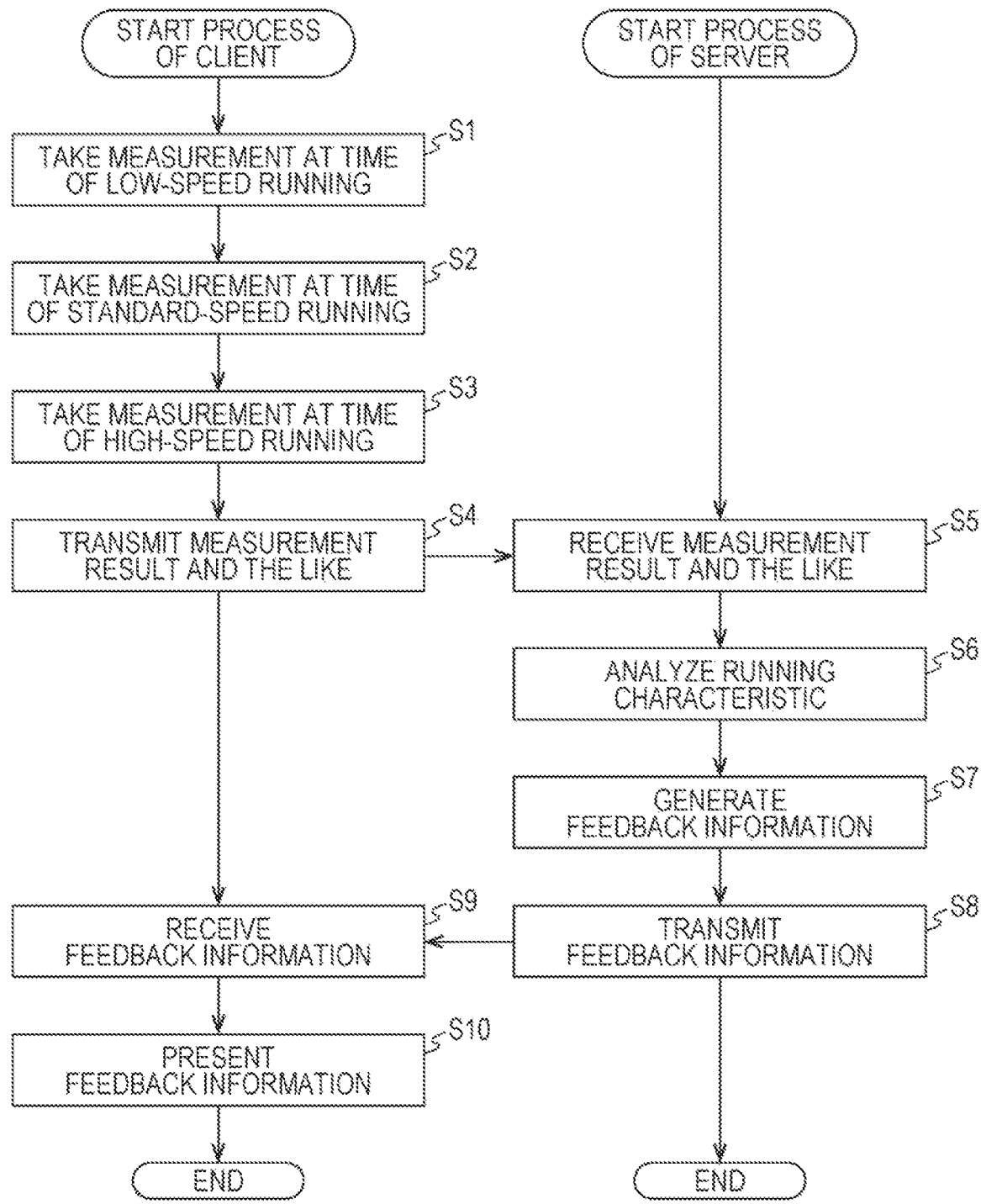
FIG. 16 is a flowchart that illustrates a running characteristic analyzing process executed by an information processing system.

In step S108, similarly to the process of step S4 illustrated in FIG. 16, the client 112 transmits measurement results and the like.

In step S109, similarly to the process of step S5 illustrated in FIG. 16, the server 111 receives the measurement results and the like transmitted from the client 112.

In step S110, the cardiorespiratory capacity analyzing unit 262 of the server 111 analyzes the cardiorespiratory capacity. For example, the cardiorespiratory capacity analyzing unit 262 calculates an average value of speeds during a predetermined period immediately before the execution of the process of step S106 among speeds at the time of standard-speed running measured in the process of step S105 as a standard speed. In addition, the cardiorespiratory capacity analyzing unit 262 calculates an average value of the heart rates during the same period as a standard heart rate.

In addition, the cardiorespiratory capacity analyzing unit 262 divides a high-speed running period in the process of step S107 into a plurality of sub-periods each having a predetermined time width and calculates an average value of the heart rates of each of the sub-periods. Then, the cardiorespiratory capacity analyzing unit 262 sets a maximum value of the average values of the heart rates during the sub-periods as a highest heart rate. This highest heart rate has a value that is very close to the upper limit value of the heart rate of the target user.

Furthermore, the cardiorespiratory capacity analyzing unit 262 sets a value acquired by multiplying the highest heart rate by a predetermined coefficient (for example, 0.8) as a sustainable heart rate of the target user.

The cardiorespiratory capacity analyzing unit 262 may be configured to analyze the cardiorespiratory capacity in consideration of the influence of the running environment. For example, the cardiorespiratory capacity analyzing unit 262 divides the air pressure, which is one kind of the environment information, into a plurality of ranges and individually acquires a standard speed, a standard heart rate, a highest heart rate, and a sustainable heart rate for each of the ranges. Accordingly, the accuracy of the analysis of the cardiorespiratory capacity is improved.

The cardiorespiratory capacity analyzing unit 262 stores a result of the analysis of the cardiorespiratory capacity of the target user in the storage unit 202.

In step S111, the cardiorespiratory capacity analyzing unit 262 generates feedback information. For example, the cardiorespiratory capacity analyzing unit 262 generates feedback information including the result of the analysis of the cardiorespiratory capacity of the target user and a message toward the target user. The message toward the target user, for example, includes description of the result of the analysis of the cardiorespiratory capacity, an advice for the target user that is based on the cardiorespiratory capacity, and the like.

In step S112, the cardiorespiratory capacity analyzing unit 262 of the server 111 transmits the feedback information to the mobile terminal 121 of the target user and, the process executed by the server 111 ends.

In step S113, the UI control unit 353 of the mobile terminal 121 receives the feedback information transmitted from the server 111.

Figure 23:
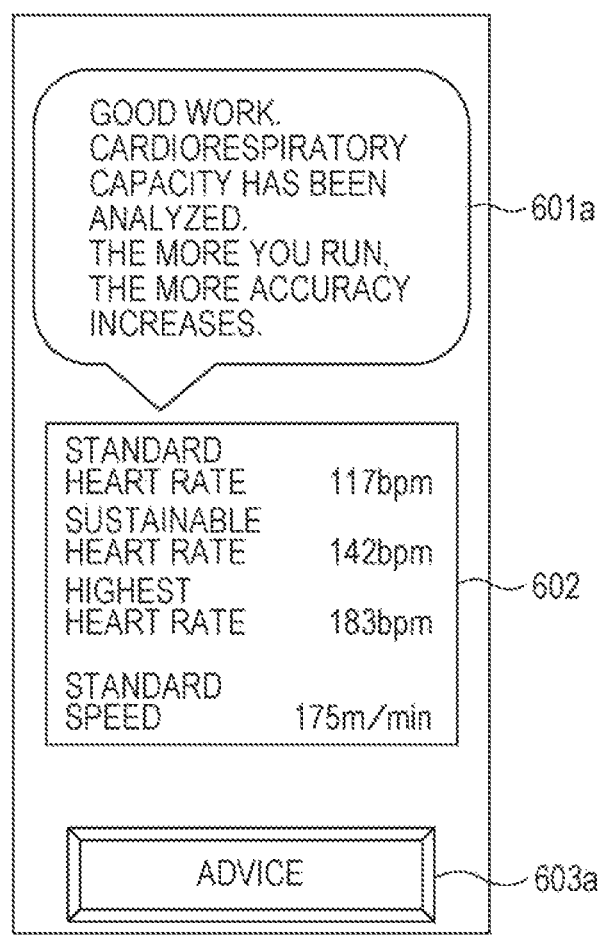
FIG. 23 is a diagram that illustrates a first example of a screen presenting an analysis result of a cardiorespiratory capacity.

In step S114, the client 112 presents the feedback information, and the process executed by the client 112 ends. For example, the output unit 306 of the mobile terminal 121 displays a screen illustrated in FIG. 23, thereby presenting the feedback information to the target user. On the screen illustrated in FIG. 23, a balloon 601a, a window 602, and a button 603a are displayed.

Inside the balloon 601a, a message for a target user is displayed. In this example, a message conveying that the accuracy of the analysis of the cardiorespiratory capacity is improved as running is repeated is included.

Inside the window 602, as a result of the analysis of the cardiorespiratory capacity of the target user, a standard heart rate, a sustainable heart rate, a highest heart rate, and a standard speed are displayed.

Figure 24:
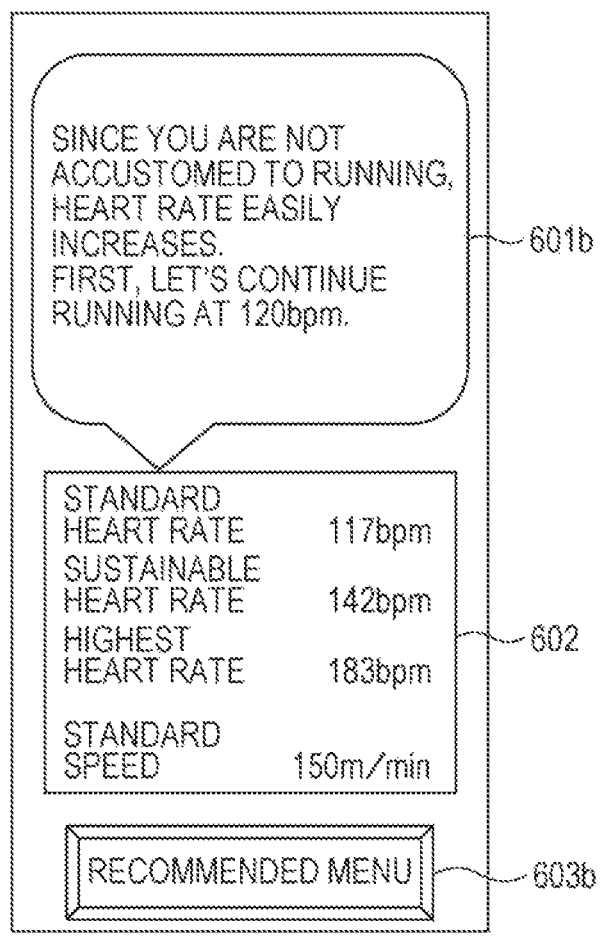
FIG. 24 is a diagram that illustrates a second example of the screen presenting an analysis result of a cardiorespiratory capacity.
Figure 25:
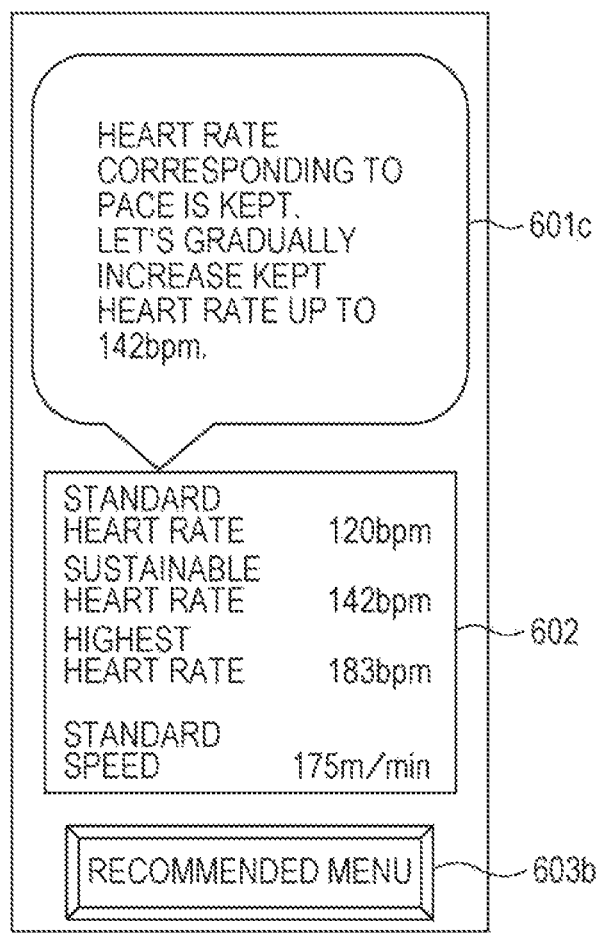
FIG. 25 is a diagram that illustrates a third example of the screen presenting an analysis result of a cardiorespiratory capacity.
Figure 26:
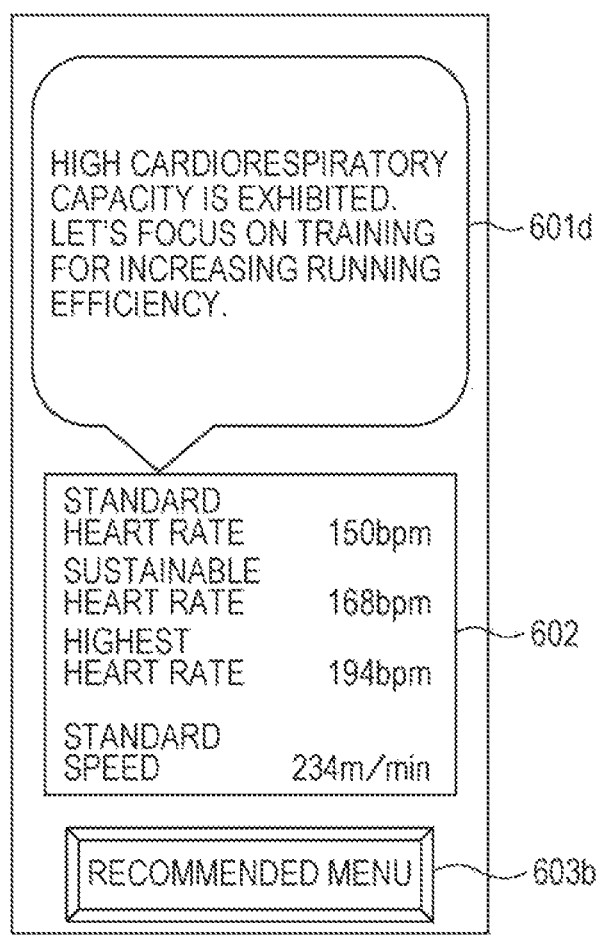
FIG. 26 is a diagram that illustrates a fourth example of the screen presenting an analysis result of a cardiorespiratory capacity.

When the button 603a is pressed, an advice for the target user and the like are displayed. FIGS. 24 to 26 illustrate examples of screens that are displayed when the button 603a is pressed.

On the screens illustrated in FIGS. 24 to 26, balloons 601b to 601d are respectively displayed instead of the balloon 601a, and a button 603b is displayed instead of the button 603a. The window 602 is continuously displayed as it is. The screen illustrated in FIG. 24 is for the same user as that of the screen illustrated in FIG. 23, and the screens illustrated in FIGS. 25 and 26 are for users different from the user of the screen illustrated in FIG. 23.

On each of the balloons 601b to 601d, for example, a current state of the target user, an advice for the target user, and the like are displayed. For example, in the balloon 601b, a message indicating that, since the target user is not accustomed to running, the heart rate may be easily raised, a target value of the heart rate, and urging the target user to continue to run at the heart rate is displayed. In the balloon 601c, a message indicating that the heart rate of the target user is set to a value corresponding to the pace and urging the target user to gradually raise the keeping heart rate is displayed. In the balloon 601d, a message indicating that the cardiorespiratory capacity of the target user is superior and urging the target user to perform training for increasing the running efficiency is displayed.

When the button 603b is pressed, a recommended menu of training for the target user is displayed. For example, a target value of the pace, the heart rate, or the like is set in correspondence with the cardiorespiratory capacity of the target user, and a training method for achieving the target value is displayed on the recommended menu. For example, distribution between training for maintaining the heart rate to be approximately constant for a long time and training for raising the upper limit value of the heart rate by applying a load, the intensity of the training, and the like are displayed on the recommended menu.

In this way described above, the cardiorespiratory capacity of the target user can be analyzed. In addition, since the measurement is performed while delicately controlling the load of the target user based on the running characteristic, the cardiorespiratory capacity of the target user can be accurately analyzed by measurement performed once.

Accordingly, immediately after the start of use of a running support service, the target user can acquire his cardiorespiratory capacity and can receive an appropriate advice according to the cardiorespiratory capacity. In this way, the target user can be prevented from being tired of the service, and the target user's motivation can be raised.

In addition, by repeatedly executing this cardiorespiratory capacity analyzing process and updating the result of the analysis of the cardiorespiratory capacity, the accuracy of the result of the analysis is further improved. For example, even when the cardiorespiratory capacity is changed according to training or the like, the target user can receive an advice appropriate for his cardiorespiratory capacity and perform appropriate training.

The cardiorespiratory capacity analyzing unit 262, for example, may perform the analysis of the cardiorespiratory capacity by using not only the measurement data of the target user but also measurement data of other users similar to the target user. For example, the cardiorespiratory capacity analyzing unit 262 classifies users into a plurality of clusters based on a predetermined parameter. Here, as the predetermined parameter, for example, in the process of step S107 described above, the heart rate at the time of user's inputting the instruction for stopping the guide, a speed at a time point when the heart rate rapidly increases, a heart rate increased at the time of the last spurt, and information of the age, sex, height, weight, and the like of the target user may be used. The cardiorespiratory capacity analyzing unit 262 analyzes the cardiorespiratory capacity of the target user by using the measurement data of users belonging to the same cluster as that of the target user in addition to the measurement data of the target user.

In addition, other than the parameters described above, for example, users may be classified into clusters based on the running characteristic.

(Stamina Characteristic Analyzing Process)

Figure 27:
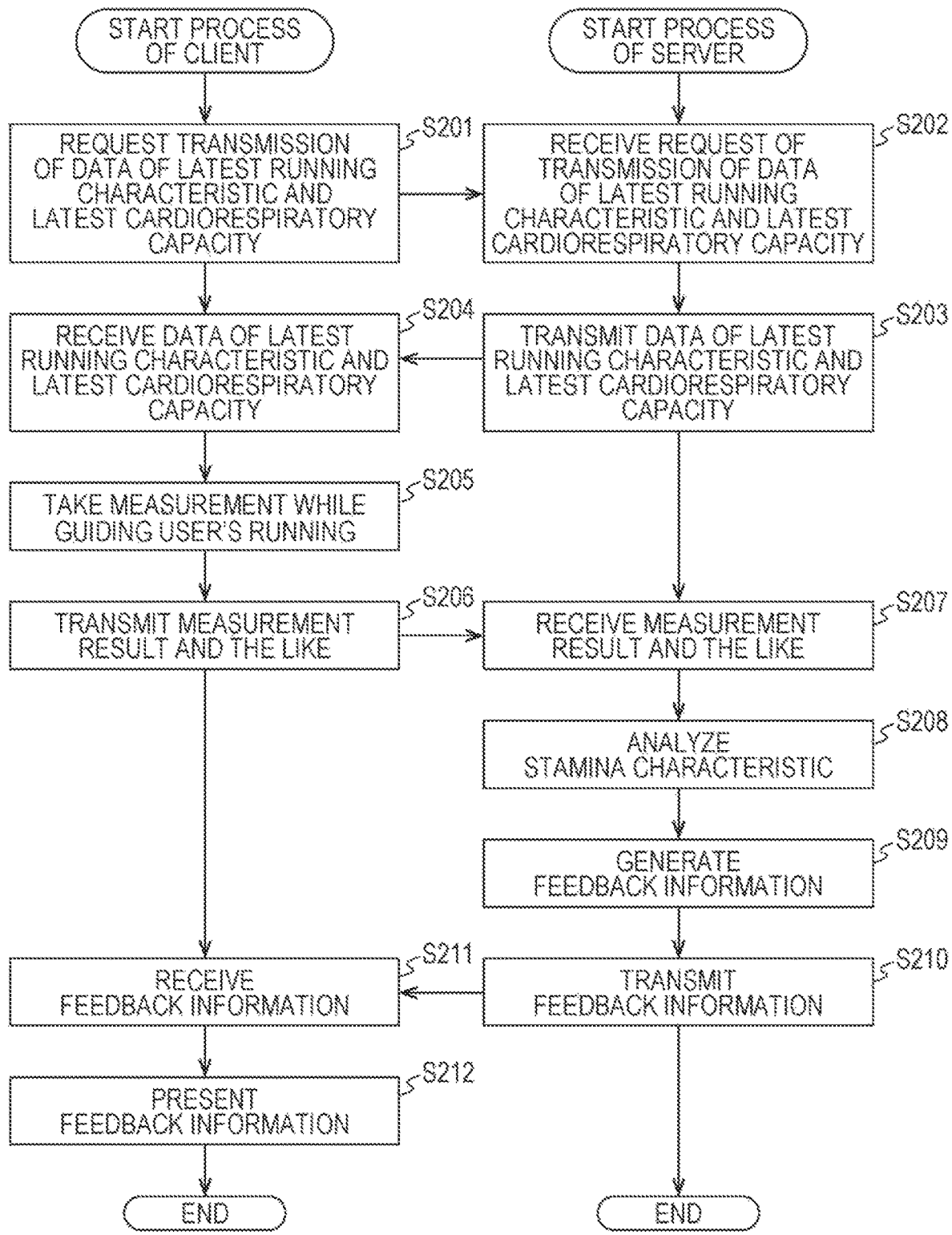
FIG. 27 is a flowchart that illustrates a stamina characteristic analyzing process executed by an information processing system.

Next, a stamina characteristic analyzing process executed by the information processing system 101 will be described with reference to a flowchart illustrated in FIG. 27. For example, this process is started when a user (hereinafter, referred to as a target user in this process) who is a target for the analysis of the stamina characteristic inputs an instruction for executing the stamina characteristic analyzing process to the mobile terminal 121 or the wearable terminal 122.

In step S201, the guide unit 352 of the mobile terminal 121 requests the server 111 to transmit data of the latest running characteristic and the latest cardiorespiratory capacity of the target user.

In step S202, the running characteristic analyzing unit 261 and the cardiorespiratory capacity analyzing unit 262 of the server 111 receive the request for the transmission of data of the latest running characteristic and the latest cardiorespiratory capacity of the target user.

In step S203, the running characteristic analyzing unit 261 and the cardiorespiratory capacity analyzing unit 262 of the server 111 read the data of the latest running characteristic and the latest cardiorespiratory capacity of the target user from the storage unit 202 and transmit the read data to the mobile terminal 121 of the target user.

In step S204, the guide unit 352 of the mobile terminal 121 receives the data of the latest running characteristic and the latest cardiorespiratory capacity of the target user that are transmitted from the server 111.

In step S205, the client 112 performs measurement while guiding user's running. For example, the guide unit 352 of the mobile terminal 121 notifies the wearable terminal 122 of the start of the stamina characteristic analyzing process. The output unit 405 of the wearable terminal 122, for example, outputs a voice message of "Your stamina is analyzed". In addition, the output unit 405, for example, outputs a voice message of "A change in pace is measured while you runs with the heart rate maintained.

The data collecting unit 471 of the wearable terminal 122 starts collecting measurement data acquired by each device of the measurement unit 406 and transmitting the collected measurement data to the mobile terminal 121. The running state analyzing unit 361 of the mobile terminal 121 starts calculating a speed, a pitch, and a stride based on the received measurement data. In addition, the running state analyzing unit 361 starts storing the measurement data of the speed, the pitch, the stride, the heart rate, and the like of the target user in the storage unit 302.

Then, the guide unit 352 of the mobile terminal 121 starts the process of guiding the speed and the like of the target user through the wearable terminal 122 while monitoring the heart rate of the target user. For example, the output unit 405 of the wearable terminal 122 outputs a voice message of "Please run according to an instruction of a heard sound" and starts guiding the target user.

Here, the guide unit 352 guides the speed of the target user such that the heart rate finally transits to a value that is slightly lower than the sustainable heart rate while gradually raising the speed. In addition, the guide unit 352 guides the pitch and the stride of the target user to approximately follow the running characteristic.

The speed of the target user at this time is higher than the standard speed and a speed at which the stamina efficiency is the highest. Accordingly, the remaining stamina amount of the target user can be decreased in a short time, and a measurement time for data that is necessary for the analysis of the stamina characteristic can be shortened.

Next, the output unit 405 of the wearable terminal 122, for example, outputs a voice message of "If you feel that it is too hard, please knock on the device". Then, for example, in a case where the target user feels it painful to further raise the speed, the target user inputs an instruction for stopping the guidance to the mobile terminal 121 or the wearable terminal 122.

For this, the guide unit 352 of the mobile terminal 121 instructs the wearable terminal 122 to stop the guidance and the measurement. The data collecting unit 471 of the wearable terminal 122 stops the collection of the measurement data acquired by each device of the measurement unit 406 and the transmission of the collected measurement data to the mobile terminal 121. The output unit 405 of the wearable terminal 122 stops guiding the target user.

In step S206, the client 112, similarly to the process of step S4 illustrated in FIG. 16, transmits the measurement results and the like.

In step S207, the server 111, similarly to the process of step S5 illustrated in FIG. 16, receives the measurement results and the like transmitted from the client 112.

In step S208, the stamina characteristic analyzing unit 263 of the server 111 analyzes the stamina characteristic.

For example, in a case where the target user is guided to maintain a value that is slightly lower than the sustainable heart rate, in a graph representing the transitions of the heart rate and the speed with respect to the running time or the running distance, a phenomenon in which the speed is gradually decreased while the heart rate is maintained to be approximately constant appears. Alternatively, in a case where the target user is guided to run while maintaining a speed that is the cardiorespiratory limit speed or less, in a graph representing the transitions of the heart rate and the speed with respect to the running time or the running distance, a phenomenon in which the heart rate is rapidly raised while the speed is maintained to be approximately constant appears.

The stamina characteristic analyzing unit 263, for example, estimates the stamina capacity of the target user based on a decreasing curve of a portion at which the speed decreases, an increasing curve in which the heart rate rapidly increases, or the like.

In addition, the stamina characteristic analyzing unit 263 estimates the stamina efficiency characteristic of the target user based on the transitions of the heart rate and the speed (or the pitch and the stride) with respect to the running time or the running distance of the target user and the running characteristic and the cardiorespiratory capacity of the target user. Here, the stamina efficiency characteristic represents a relation among the remaining stamina amount, the speed (or the pitch and the stride), and the stamina efficiency.

The stamina efficiency changes according to the remaining stamina amount and the speed (or the pitch and the stride). In other words, even for the same remaining stamina amount, the stamina efficiency changes according to the running speed (or the pitch and the stride). In addition, even in case of running at the same speed (or the pitch and the stride), the stamina efficiency changes according to the remaining stamina amount.

For example, the stamina characteristic analyzing unit 263 estimates a consumed stamina amount per unit distance of a case where the speed (or the pitch and the stride) is changed for a plurality of mutually-different remaining stamina amounts based on the transitions of the heart rate and the speed (or the pitch and the stride) with respect to the running time or the running distance of the target user and the running characteristic and the cardiorespiratory capacity of the target user, thereby estimating the stamina efficiency characteristic.

The accuracy of the estimation of the stamina capacity and the stamina efficiency characteristic is improved by repeating the stamina characteristic analyzing process. Particularly, by repeating the stamina characteristic analyzing process with the speed maintained by the target user changed, the accuracy of the estimation of the stamina efficiency is improved.

In addition, the stamina capacity and the stamina efficiency characteristic are changed according to the condition of the target user. Thus, the stamina characteristic analyzing unit 263 learns a relation among the condition index or the condition class, the stamina capacity, and the stamina efficiency characteristic while repeating the stamina characteristic analyzing process. The condition index or the condition class may be acquired based on data relating to the condition of the target user among measurement data acquired by each device of the measurement unit 406 or may be explicitly input as a numerical value or the like by the target user.

The stamina characteristic analyzing unit 263, for example, may form the result of the analysis of the stamina capacity and the stamina efficiency characteristic as a database or a function. In a case where the result of the analysis is formed as a database, the stamina characteristic analyzing unit 263, for example, generates a database that is different for each condition class.

Alternatively, in a case where the result of the analysis is formed as a function, the stamina characteristic analyzing unit 263, for example, generates a function for calculating a stamina capacity by using the condition index (or condition class) as a variable. In addition, for example, the stamina characteristic analyzing unit 263 generates a function for calculating a stamina efficiency characteristic by using the remaining stamina amount, the speed (or the pitch and the stride), and the condition index (or the condition class) as variables.

In addition, the stamina characteristic analyzing unit 263 calculates a runnable distance of the target user and an estimated time that is necessary for running the runnable distance based on the running characteristic, the cardiorespiratory capacity, the stamina capacity, and the stamina efficiency characteristic of the target user.

In step S209, the stamina characteristic analyzing unit 263 generates feedback information. For example, the stamina characteristic analyzing unit 263 generates feedback information including the result of the analysis of the stamina characteristic of the target user and a message toward the target user. The message toward the target user, for example, includes description of the result of the analysis of the stamina characteristic, an advice for the target user that is based on the stamina characteristic, and the like.

In step S210, the stamina characteristic analyzing unit 263 of the server 111 transmits the feedback information to the mobile terminal 121 of the target user and, the process executed by the server 111 ends.

In step S211, the UI control unit 353 of the mobile terminal 121 receives the feedback information transmitted from the server 111.

Figure 28:
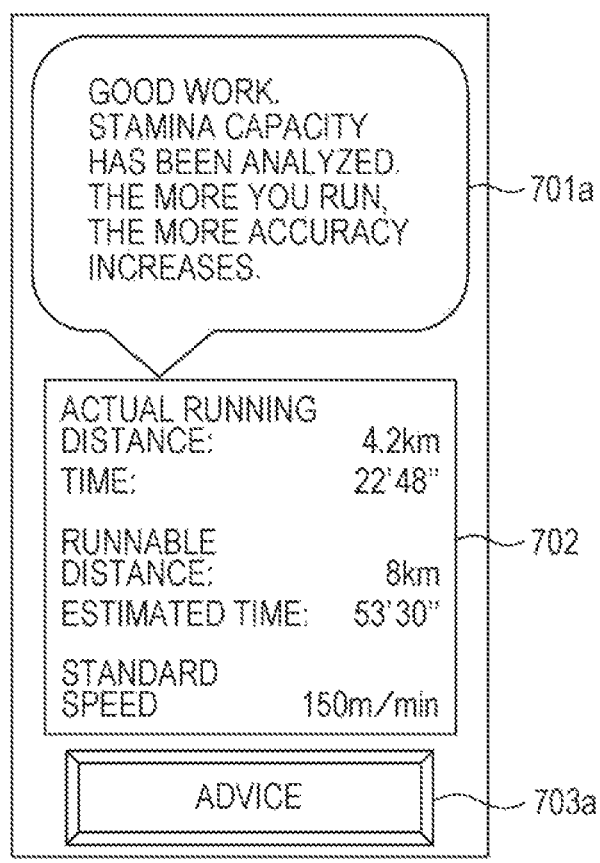
FIG. 28 is a diagram that illustrates a first example of a screen presenting an analysis result of a stamina characteristic.

In step S212, the client 112 presents the feedback information, and the process executed by the client 112 ends. For example, the output unit 306 of the mobile terminal 121 displays a screen illustrated in FIG. 28, thereby presenting the feedback information to the target user. On the screen illustrated in FIG. 28, a balloon 701a, a window 702, and a button 703a are displayed.

Inside the balloon 701a, a message for a target user is displayed. In this example, a message conveying that the accuracy of the analysis of the stamina characteristic is improved as running is repeated is included.

Inside the window 702, as a result of the analysis of the stamina characteristic of the target user, an actual running distance, a time, a runnable distance, an estimated time, and a standard speed are displayed. Here, the actual running distance is a distance that is actually run by the target user for analyzing the stamina characteristic, and the time is a time that is necessary for running the distance.

Figure 29:
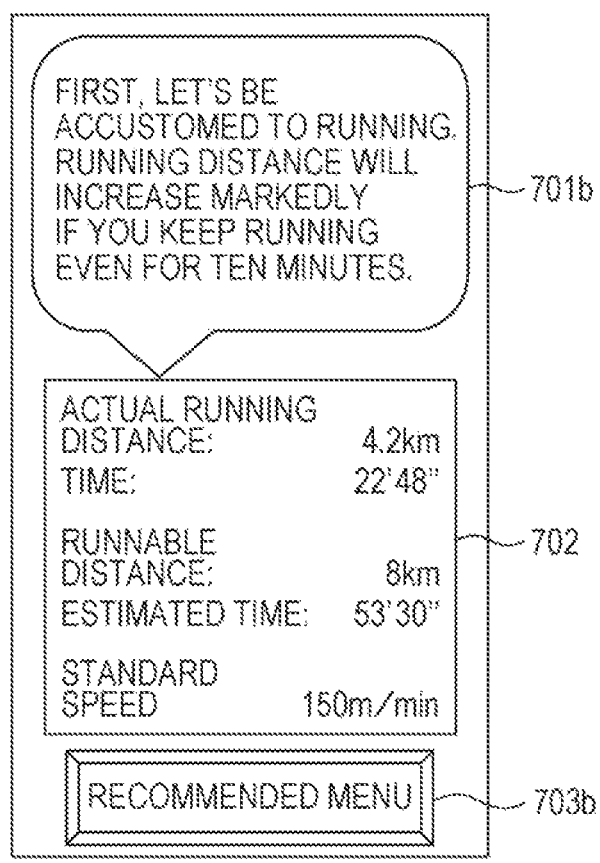
FIG. 29 is a diagram that illustrates a second example of the screen presenting an analysis result of a stamina characteristic.
Figure 30:
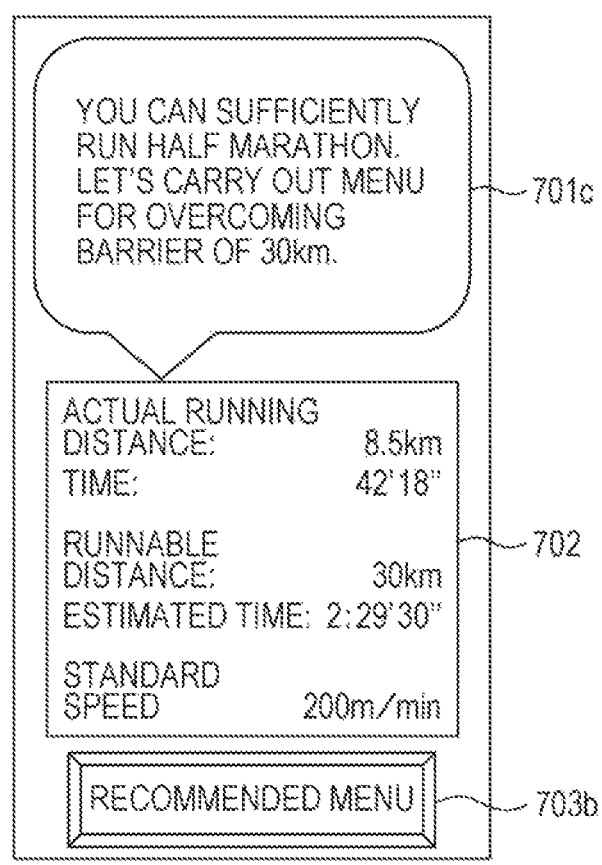
FIG. 30 is a diagram that illustrates a third example of the screen presenting an analysis result of a stamina characteristic.

When the button 703a is pressed, an advice for the target user and the like are displayed. FIGS. 29 and 30 illustrate examples of screens that are displayed when the button 703a is pressed.

On the screens illustrated in FIGS. 29 and 30, balloons 701b and 701c are respectively displayed instead of the balloon 701a, and a button 703b is displayed instead of the button 703a. The window 702 is continuously displayed as it is. The screen illustrated in FIG. 29 is for the same user as that of the screen illustrated in FIG. 28, and the screen illustrated in FIG. 30 is for a user different from the user of the screen illustrated in FIG. 28.

On each of the balloons 701b and 701c, for example, a current state of the target user, an advice for the target user, and the like are displayed. For example, in the balloon 701b, a message indicating that, first, it is necessary for the target user to be accustomed to running and an advice for being accustomed to running are displayed. In the balloon 701c, a message indicating that the target user has an ability to run the whole half marathon course and an advice for the future are displayed.

When the button 703b is pressed, a recommended menu of training for the target user is displayed. For example, a training distance or a target distance is set in correspondence with the stamina characteristic of the target user, and a training method for running the whole target distance is displayed on the recommended menu. In addition, for example, a menu for increasing the distance at a suppressed pace, a menu for gradually raising the running pace, a menu for not decreasing the pace in a section in which the target user suffers from insufficiency of oxygen, and the like are displayed.

In this way described above, the stamina characteristic of the target user can be analyzed. In addition, since the measurement is performed while delicately controlling the load of the target user based on the running characteristic and the cardiorespiratory characteristic, the stamina characteristic of the target user can be accurately analyzed by measurement performed once.

Accordingly, immediately after the start of use of a running support service, the target user can acquire his stamina characteristic and can receive an appropriate advice according to the stamina characteristic. In this way, the target user can be prevented from being tired of the service, and the target user's motivation can be raised.

In addition, by repeating this stamina characteristic analyzing process and updating the result of the analysis, even when the stamina characteristic is changed according to training or the like, the target user can receive an advice appropriate for his stamina characteristic and perform appropriate training.

The stamina characteristic analyzing unit 263, for example, may be configured to classify users of the running support service into a plurality of clusters based on at least one of the running characteristic and the cardiorespiratory capacity and analyzes the stamina characteristic by using not only the measurement data of the target user but also the measurement data of other users of a cluster to which the target user belongs. In addition, for example, by using information of the age, sex, height, weight, and the like, the users may be classified into a plurality of clusters.

(Running State Analyzing Process)

Next, a running state analyzing process executed by the client 112 will be described with reference to a flowchart illustrated in FIG. 31. For example, this process is started when a user (hereinafter, referred to as a target user in this process) who is a target for analyzing the running state inputs an instruction for executing the running state analyzing process to the mobile terminal 121 or the wearable terminal 122.

In step S301, the mobile terminal 121 acquires a latest running characteristic. More specifically, the running state analyzing unit 361 of the mobile terminal 121 requests the server 111 to transmit the latest running characteristic of the target user. Then, the running state analyzing unit 361 receives the latest running characteristic of the target user that is transmitted from the server 111 in response to the request.

The latest running characteristic of the target user may be stored in the storage unit 302 of the mobile terminal 121 in advance.

In step S302, the client 112 starts measurement and guidance. More specifically, the running state analyzing unit 361 of the mobile terminal 121 instructs the wearable terminal 122 to start measurement. The data collecting unit 471 of the wearable terminal 122 starts collecting measurement data acquired by each device of the measurement unit 406 and transmitting the collected measurement data to the mobile terminal 121.

The running state analyzing unit 361 starts calculating a speed, a pitch, and a stride based on the received measurement data. In addition, the running state analyzing unit 361 starts storing the measurement data of the speed, the pitch, the stride, the heart rate, and the like of the target user in the storage unit 302.

In addition, the running state analyzing unit 361 starts transmitting the measurement results of the speed, the pitch, the stride, the heart rate, and pitch-stride balance to be described later of the target user, environment information at the time of the measurement, user information, and the like to the server 111. The measurement results and the like transmitted at this time are stored in the server 111 and, for example, are used for analyzing the running characteristic, the cardiorespiratory capacity, and the stamina characteristic of the target user.

The running state analyzing unit 361 may be configured to transmit the measurement results and the like to the server 111 altogether later.

The guide unit 352 of the mobile terminal 121 starts guiding the speed, the pitch, and the stride through the wearable terminal 122. For example, in a case where a training menu is set, the guide unit 352 performs guiding according to the training menu.

For example, in a case where the speed of the target user is lower than the stride-pitch switching speed, the guide unit 352 performs guiding such that the speed of the target user is a predetermined speed by guiding the stride. On the other hand, in a case where the speed of the target user is the stride-pitch switching speed or higher, the guide unit 352 performs guiding such that the speed of the target user is a predetermined speed by guiding the pitch.

Here, an example of a method of guiding the pitch and the stride using a voice will be described.

For example, the output unit 405 guides the pitch and the stride of the target user by using a specific voice message.

For example, by changing the tone, the melody, the tempo, the volume, the length, the echo, the height, and the like of a guide sound, the output unit 405 guides the pitch and the stride of the target user.

For example, in a case where the pitch is guided, the output unit 405 sets the guide sound to a pitch sound like that of a metronome. Then, the output unit 405 increases the tempo of the guide sound at the time of raising the pitch and decreases the tempo of the guide sound at the time of lowering the pitch. Alternatively, for example, the output unit 405 sets the guide sound as a rising sound at the time of raising the pitch and sets the guide sound as a falling sound at the time of lowering the pitch. In addition, in a case where the pitch is within a target range, for example, the output unit 405 performs guiding so as to maintain the current pitch by stopping the output of the guide sound or outputting a voice other than the guide sound of the pitch.

Alternatively, for example, the output unit 405 guides the pitch of the target user by using a phase difference between the guide sound and landing timing. For example, the output unit 405 outputs the guide sound at timing that is one tempo later than the landing timing in case of lowering the pitch and outputs the guide sound at timing that is one tempo earlier than the landing timing in case of raising the pitch. In addition, in a case where the pitch is within a target range, the output unit 405 performs guiding so as to maintain the current pitch by outputting the guide sound almost simultaneously with the landing timing. According to this method, differently from a case where the tempo of the guide sound is controlled, a deviation of guided timing is not accumulated, and accordingly, the pitch can be appropriately guided without disturbing the running of the target user.

On the other hand, in a case where the stride is guided, the output unit 405, for example, increases the volume of the guide sound or lengthens or raises the guide sound at the time of increasing the stride and decreases the volume of the guide sound or shortens or lowers the guide sound at the time of decreasing the stride. In addition, in a case where the stride is within a target range, for example, the output unit 405 performs guiding so as to maintain the current stride by stopping the output of the guide sound or outputting a voice other than the guide sound of the stride.

Alternatively, for example, the output unit 405 guides the stride of the target user based on the position of the sound image of the guide sound. For example, the output unit 405 guides the stride by setting the sound image of the guide sound to a position of a target stride. Alternatively, for example, the output unit 405 sets the position of the sound image of the guide sound to the front side of the target user in case of increasing the stride and sets the position of the sound image of the guide sound to the rear side of the target user in case of decreasing the stride. In addition, in a case where the stride is within a target range, the output unit 405, for example, performs guiding so as to maintain the current stride by setting the position of the sound image of the guide sound to be near the body of the target user.

The output unit 405 may guide the pitch and the stride by using a method other than the method using the guide sound. For example, the output unit 405 may be configured to guide the pitch and the stride by emitting guide light onto the road surface through projection mapping or the like. For example, the output unit 405 may be configured to guide the pitch by changing the speed of turning the guide light on/off. In addition, for example, the output unit 405 may be configured to guide the stride by emitting guide light at the position of a target stride.

The output unit 405 may be configured to simultaneously guide both the pitch and the stride by combining the methods of guiding the pitch and the stride. For example, the output unit 405 may simultaneously guide the pitch and the stride by combining the guide sound of the pitch and the guide sound of the stride. In addition, for example, the output unit 405 may simultaneously guide the pitch and the stride by guiding one thereof using the guide sound and guiding the other using the guide light.

In addition, the output unit 405 may guide the speed instead of individually guiding the pitch and the stride. For example, the output unit 405 may guide only the speed in a case where running according to the running characteristic is guided and guide the pitch and the stride in a case where running with a pitch and a stride different from those of the running characteristic is guided.

Particularly, in a case where a training menu and the like are not set, it is not necessary for the guide unit 352 to perform guiding.

In step S303, the running state analyzing unit 361 of the mobile terminal 121 compares the current running state with the running characteristic. More specifically, the running state analyzing unit 361 calculates a stride (hereinafter, referred to as a standard stride Sm) corresponding to an actually-measured value of the current speed of the target user in the running characteristic of the target user. Then, the running state analyzing unit 361, first, calculates a defect parameter b0 representing balance of the current pitch and the current stride with respect to the running characteristic by using the following Equation (1).

$$b0 = \log_{10}(Sr/Sm) \qquad (1)$$

Here, Sr is an actually-measured value of the current stride of the target user.

Next, the running state analyzing unit 361 makes a sensible correction of the defect parameter by using the following Equation (2), thereby calculating pitch-stride balance br.

$$br = f(b0) = p \times b0^3 + q \times b0 \quad (2)$$

Here, p and q are predetermined constants.

The pitch-stride balance br is an index that represents the degree of separation of the balance of the current pitch and the current stride from the running characteristic. In case of stride actually-measured value Sr=standard stride Sm, in other words, in a case where the current pitch and the current stride follow the running characteristic, the pitch-stride balance br is zero. Hereinafter, a state in which the pitch and the stride follow the running characteristic will be referred to also as a neutral state. In case of stride actually-measured value Sr>standard stride Sm, in other words, in a case where the stride is longer than that of the neutral state, and the pitch is smaller than that of the neutral state, the pitch-stride balance br has a positive value. On the other hand, in case of stride actually-measured value Sr<standard stride Sm, in other words, in a case where the stride is shorter than that of the neutral state, and the pitch is larger than that of the neutral state, the pitch-stride balance br has a negative value.

According to the correction represented in Equation (2), the pitch-stride balance br has a higher change rate as the balance of the current pitch and the current stride is separated farther from the running characteristic. Accordingly, the pitch-stride balance br represents a change that is close to the sense of the target user.

Hereinafter, a state in which the stride is longer than that of the neutral state, and the pitch is smaller than that of the neutral state will be referred also as a state inclining toward the stride, a stride approach state, or a state in which the stride is dominant. On the other hand, hereinafter, a state in which the pitch is larger than that of the neutral state, and the stride is shorter than that of the neutral state will be referred also as a state inclining toward the pitch, a pitch approach state, or a state in which the pitch is dominant.

The Equations (1) and (2) described above represent an example of the method of calculating the pitch-stride balance br, and, particularly, the pitch-stride balance br does not have a unit, and thus, any other method may be used.

In addition, the running state analyzing unit 361 stores the calculated pitch-stride balance br in the storage unit 302.

In step S304, the client 112 presents a comparison result and the like. For example, the output unit 306 of the mobile terminal 121 displays a screen illustrated in FIG. 32 or FIG. 33.

Figure 32:
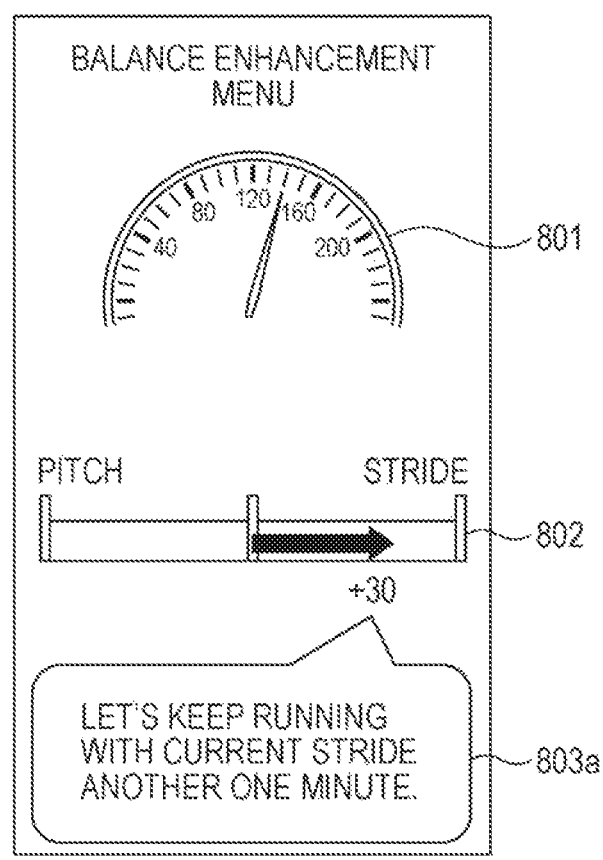
FIG. 32 is a diagram that illustrates a first example of a screen presenting an analysis result of a running state.

FIG. 32 is an example of a screen displayed in a case where user performs training for enhancing the balance of the pitch and the stride. The training for enhancing the balance of the pitch and the stride, for example, is training for running in a state in which the balance of the pitch and the stride is intentionally shifted from the neutral state. On the screen illustrated in FIG. 32, a speed meter 801, a balance meter 802, and a balloon 803a are displayed.

The speed meter 801 displays an actually-measured value of the current speed of the target user.

The balance meter 802 displays an arrow and a numerical value representing the value of the pitch-stride balance br. In a case where the pitch-stride balance br has a positive value, a rightward arrow having a length according to the absolute value thereof is displayed. On the other hand, in a case where the pitch-stride balance br has a negative value, a leftward arrow having a length according to the absolute value thereof is displayed. In a case where the pitch-stride balance br is zero, no arrow is displayed.

As described above, since FIG. 32 is the screen displayed during the training for enhancing the balance of the pitch and the stride, the absolute value of the pitch-stride balance br may be intentionally corrected to a large value so as to be displayed in a highlighted manner.

In the balloon 803a, a message toward the target user is displayed. In this example, a message instructing the target user to continue to run with the current stride maintained is displayed.

Figure 33:
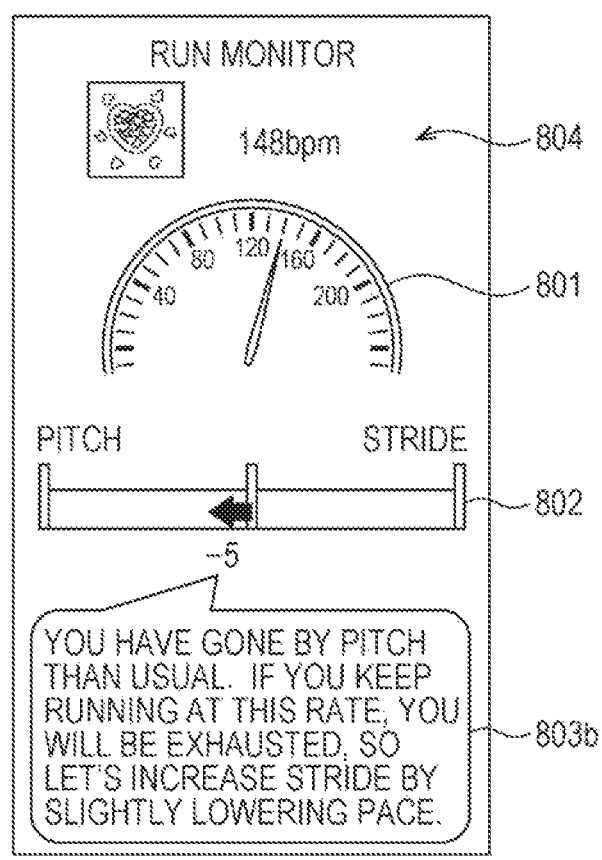
FIG. 33 is a diagram that illustrates a second example of the screen presenting an analysis result of a running state.

FIG. 33 is an example of a screen that is displayed, for example, in a case where a target user runs a real race. On the screen illustrated in FIG. 33, similarly to the screen illustrated in FIG. 32, the speed meter 801 and the balance meter 802 are displayed, and a balloon 803b is displayed instead of the balloon 803a. In addition, an actually-measured value 804 of the current heart rate of the target user is displayed.

In the balloon 803b, a message for the target user is displayed. In this example, since a state inclining toward the pitch is formed, a message urging the target user to decrease the pitch and to increase the stride is displayed.

Referring back to FIG. 31, in step S305, the running state analyzing unit 361 of the mobile terminal 121 determines whether or not the measurement and the guidance are to be ended. In a case where the measurement and the guidance are determined not to be ended, the process is returned to step S303. Thereafter, in step S305, until the measurement and the guidance are determined to be ended, the process of steps S303 to S305 is repeatedly executed. Accordingly, the running state presented to the target user is updated in real time, and a message corresponding to the running state is presented to the target user.

On the other hand, in step S305, for example, in a case where the target user inputs an instruction for stopping the measurement and the guidance to the mobile terminal 121 or the wearable terminal 122, the running state analyzing unit 361 determines to end the measurement and the guidance, and the process proceeds to step S306.

In step S306, the client 112 stops the measurement and the guidance. For example, the running state analyzing unit 361 of the mobile terminal 121 instructs the wearable terminal 122 to stop the measurement. The data collecting unit 471 of the wearable terminal 122 stops the collection of measurement data using each device of the measurement unit 406 and the transmission of the collected measurement data to the mobile terminal 121. The running state analyzing unit 361 of the mobile terminal 121 stops the transmission of the measurement results and the like to the server 111. The guide unit 352 of the mobile terminal 121 stops the guidance.

In step S307, the running state analyzing unit 361 of the mobile terminal 121 analyzes the whole measurement period. For example, the running state analyzing unit 361 analyzes the transitions of the time series of the speed, the pitch, and the stride during the measurement period, the pitch-stride balance br, and a statistical value of the balance of the pitch and the stride of the target user, and the like.

In step S308, the client 112 presents a result of the analysis and the like, and the running state analyzing process ends. For example, the output unit 306 of the mobile terminal 121 displays a screen used for presenting the result of the analysis and the like. Here, examples of the screen displayed on the output unit 306 will be described with reference to FIGS. 34 to 43.

Figure 34:
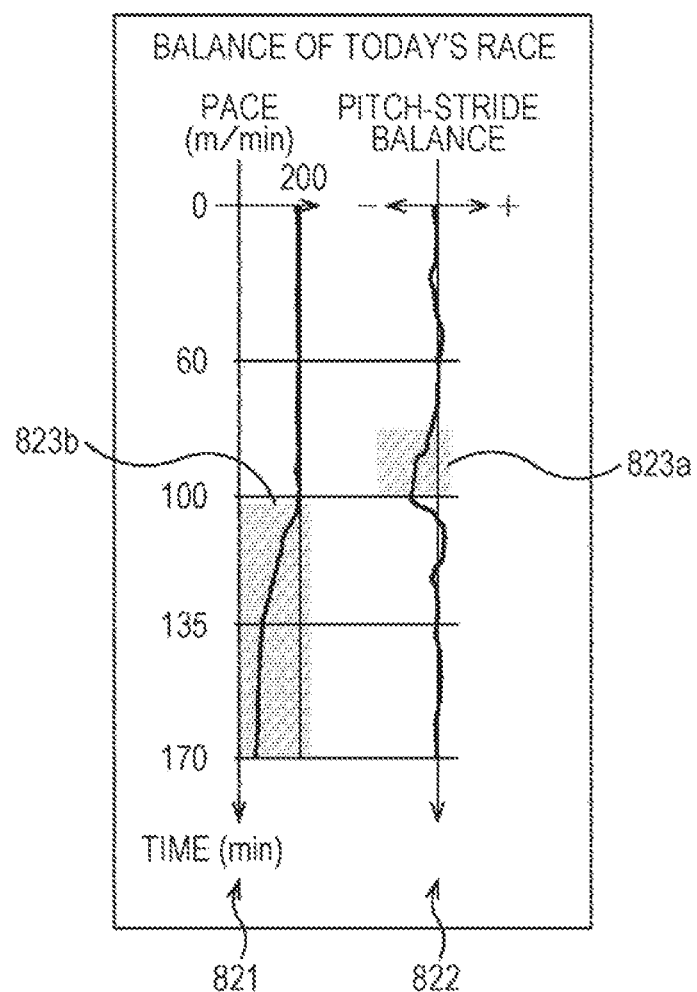
FIG. 34 is a diagram that illustrates a third example of the screen presenting an analysis result of a running state.

A screen illustrated in FIG. 34 illustrates the transitions of the time series of the pace of the target user and the pitch-stride balance br during the measurement period.

A graph 821 disposed on the left side illustrates the transition of the time series of the pace of the target user during the running period. The vertical axis is the time axis, and the horizontal axis is the pace (unit is m/min).

A graph 822 disposed on the right side illustrates the transition of the time series of the pitch-stride balance br of the target user during the running period. The vertical axis is the time axis, and the horizontal axis represents the pitch-stride balance br. The rightward direction of the horizontal axis is a positive direction, and the leftward direction is a negative direction. Thus, in the case of the state inclining toward the stride, the graph inclines to a further right side than the time axis, and, in the case of the state inclining toward the pitch, the graph inclines to a further left side than the time axis.

By using this screen, the target user can easily perceive the transitions of the time series of the pace and the balance of the pitch and the stride during the running period. In addition, the target user can analyze a problem of his running and the like.

Figure 35:
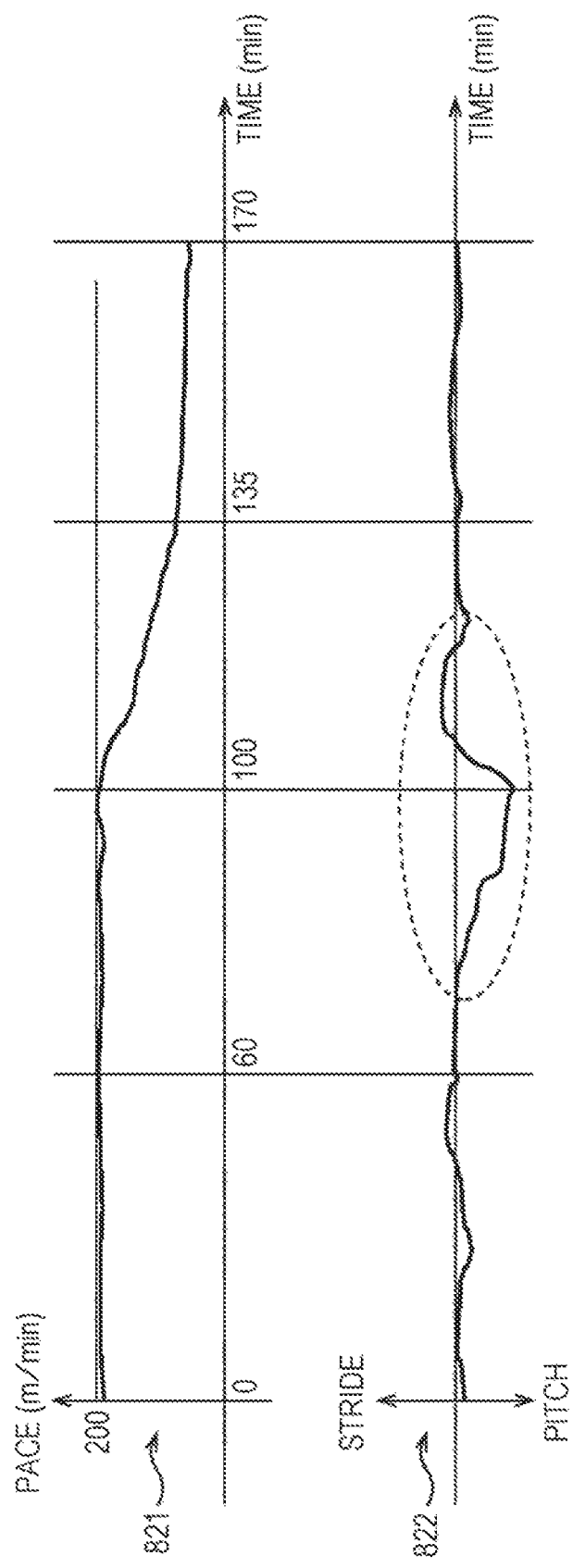
FIG. 35 is a diagram acquired by enlarging a graph illustrated in FIG. 34.

FIG. 35 is a diagram acquired by horizontally enlarging the graphs 821 and 822 illustrated in FIG. 34. For example, from these graphs, it can be understood that the balance of the pitch and the stride is kept until the elapse of about 70 minutes from the start, and running in the best condition is performed until then.

On the other hand, during a period of about 70 minutes from the start to about 100 minutes, running inclining toward the pitch is formed, and the inclining toward the pitch gradually increases. In this period, for example, it is assumed that the target user suffers and tries to maintain the pace by forcibly increasing the pitch in correspondence with a decrease in the stride.

Then, during a period of the elapse of about 100 minutes to about 135 minutes, the state transits from the state inclining toward the pitch to the neutral state, and the pace is greatly lowered. During this period, for example, it is assumed that the stamina of the target user runs out, and the pitch is not maintained, and the pace is greatly lowered.

Then, after an elapse of about 135 minutes, the neutral state and a low pace are maintained. During this period, for example, it is assumed that, although the stamina of the target user runs out, anyhow, the target user eagerly runs at a slow pace.

To sum up, during a period, which is enclosed by a dotted line, of the graph 822 in which the balance of the pitch and the stride is lost, it can be understood that the target user forcibly runs.

On the screen illustrated in FIG. 34, periods 823a and 823b in which forcible running is performed, or capacity insufficiency appears are displayed to be discriminated from the other periods. The period 823a is a period in which the state inclining toward the pitch is continued, and the period 823b is a period in which the pace is greatly lowered.

Figure 36:
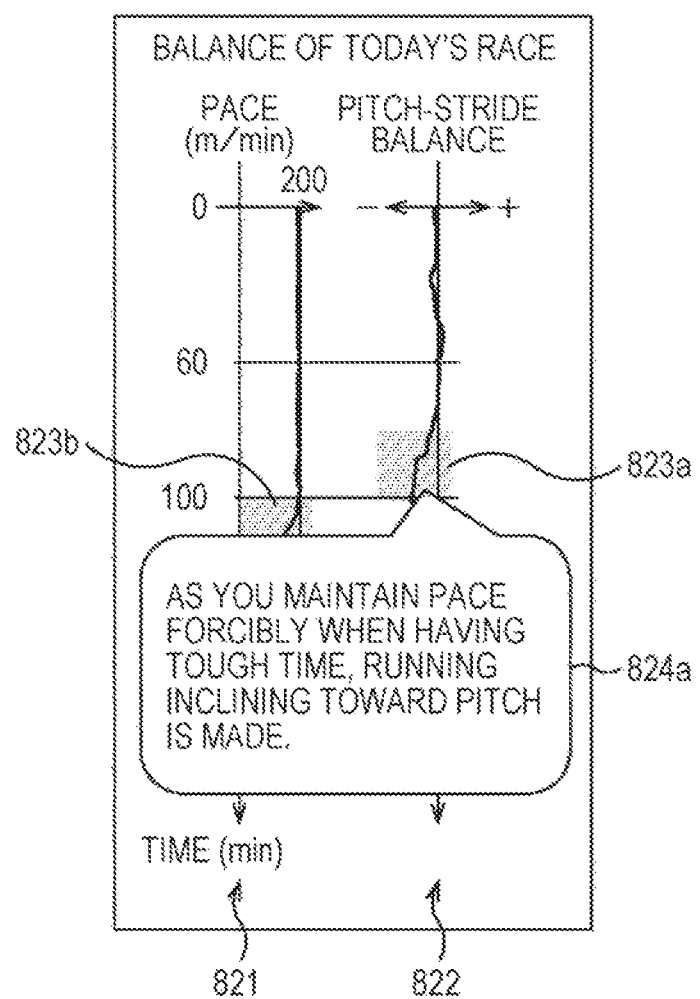
FIG. 36 is a diagram that illustrates a fourth example of the screen presenting an analysis result of a running state.

For example, in a case where the target user designates the period 823a, as illustrated in FIG. 36, a balloon 824a is displayed near the period 823a. Inside the balloon 824a, in the period 823a, a message notifying the target user that the type of forcible running of the target user is running inclining toward the pitch so as to maintain the pace is displayed.

Figure 37:
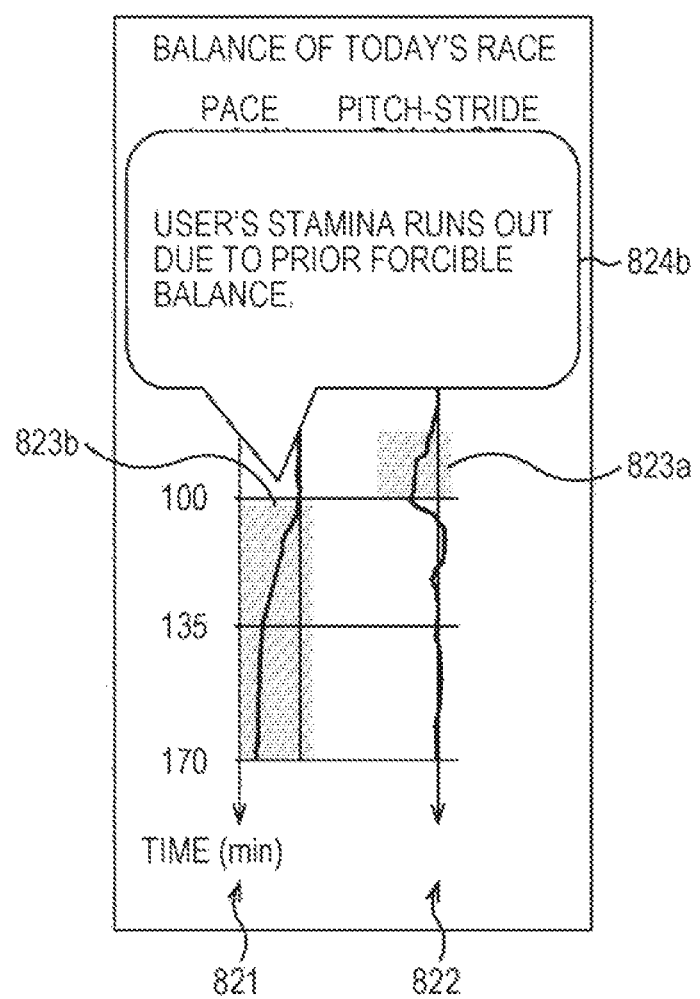
FIG. 37 is a diagram that illustrates a fifth example of the screen presenting an analysis result of a running state.
Figure 38:
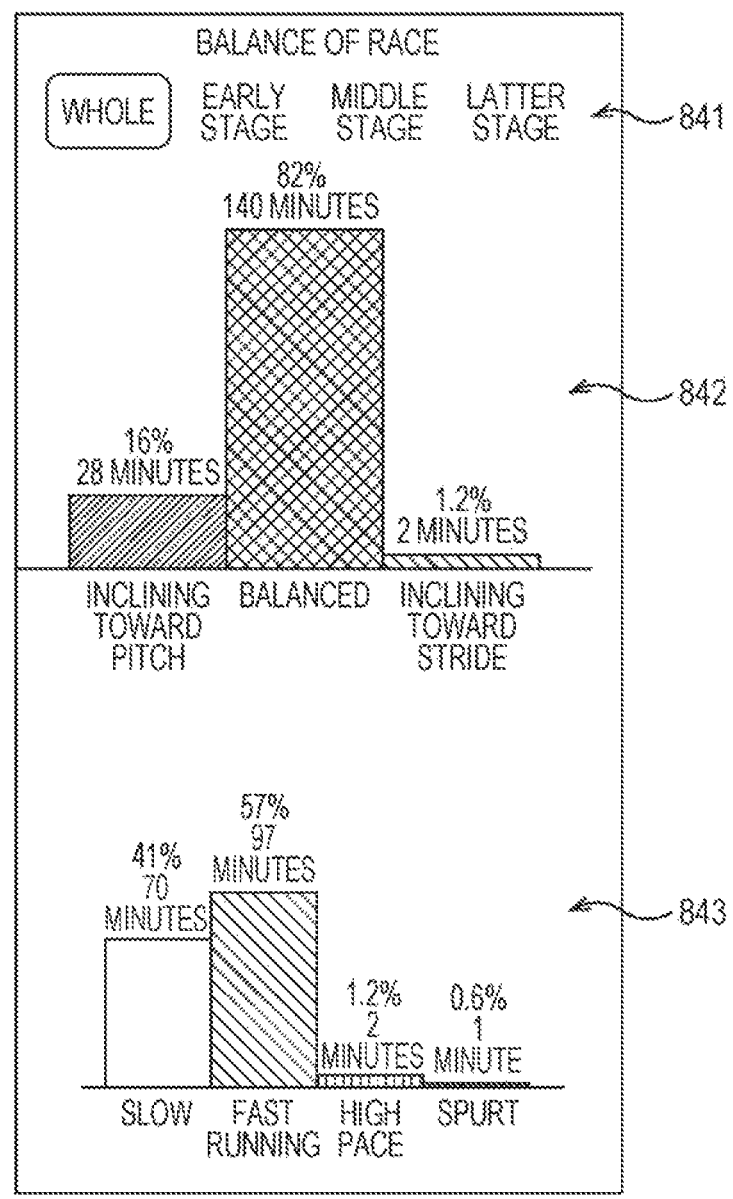
FIG. 38 is a diagram that illustrates a sixth example of the screen presenting an analysis result of a running state.
Figure 39:
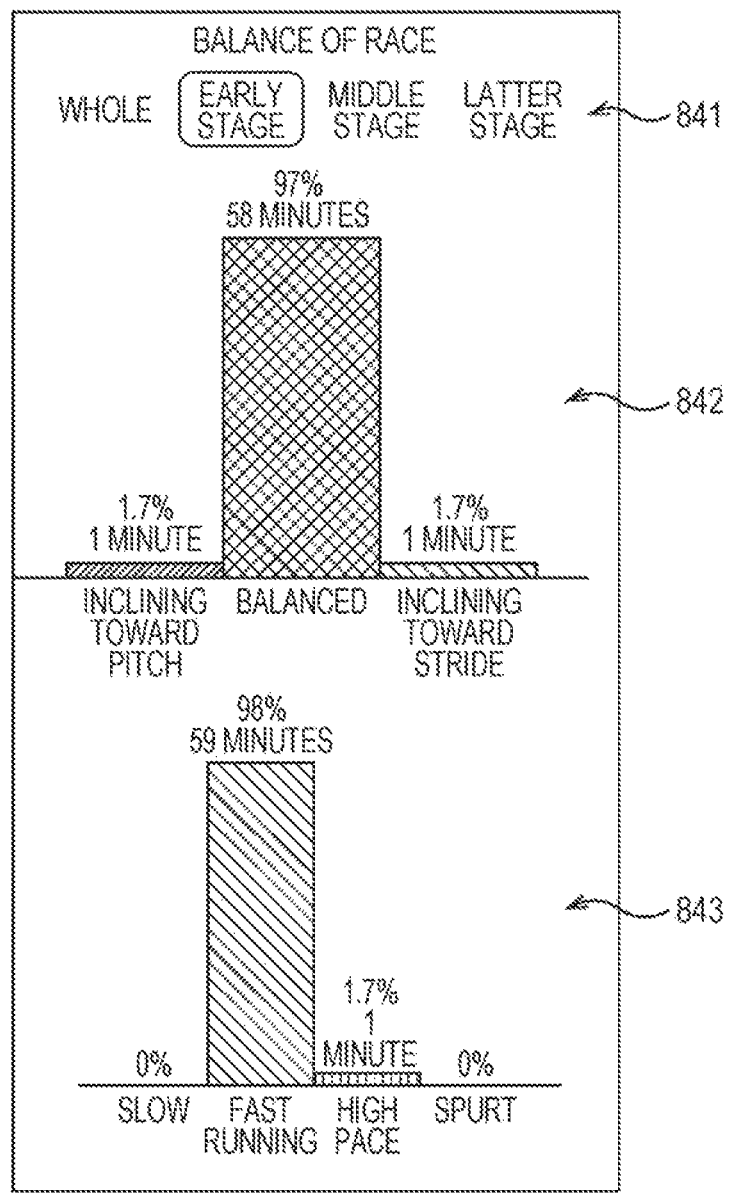
FIG. 39 is a diagram that illustrates a seventh example of the screen presenting an analysis result of a running state.
Figure 40:
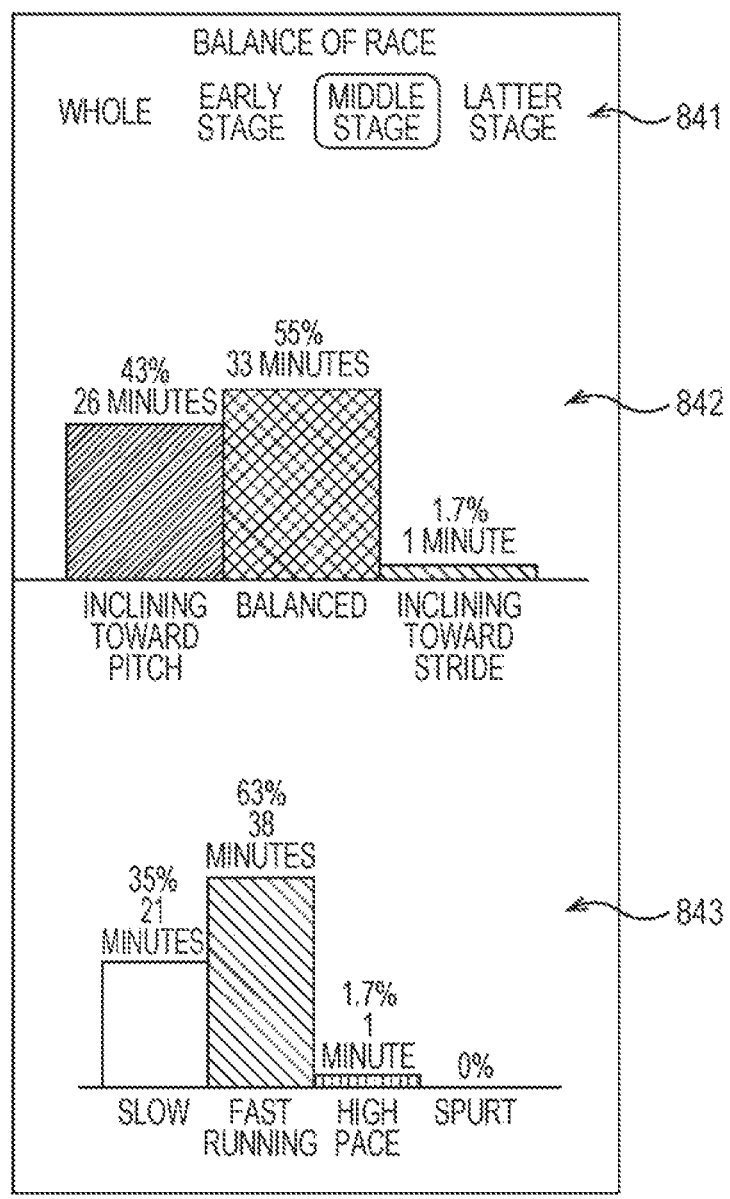
FIG. 40 is a diagram that illustrates an eighth example of the screen presenting an analysis result of a running state.
Figure 41:
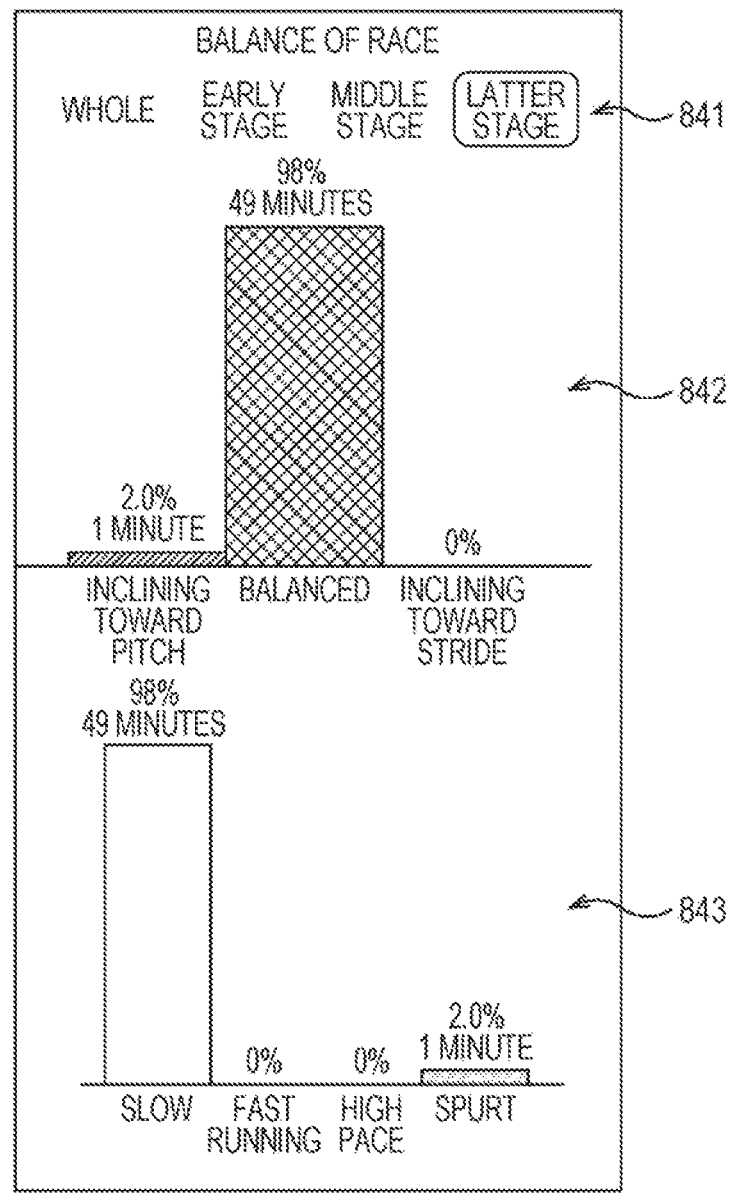
FIG. 41 is a diagram that illustrates a ninth example of the screen presenting an analysis result of a running state.

On the other hand, for example, in a case where the target user designates the period 823b, as illustrated in FIG. 37, a balloon 824b is displayed near the period 823b. Inside the balloon 824b, a message notifying the target user of an occurrence of running-out of the stamina in the period 823b due to forcible running inclining toward the pitch during a prior period (period 823a) is displayed.

The output unit 306, for example, may be configured to present recommended training according to a cause of the forcible running or a cause of the capacity insufficiency. For example, in a case where the target user has an increased heart rate in spite of a low speed, and it is difficult to maintain the pace, the output unit 306 may recommend cardiorespiratory training. In addition, for example, in a case where it is difficult for the target user to increase the distance while a high heart rate of some degree can be maintained, the output unit 306 may recommend training for increasing the distance first with the pace lowered. Furthermore, in a case where a stride that is expected based on the physical constitution is not achieved by the target user, the output unit 306 may recommend training for increasing the stride.

Screens illustrated in FIGS. 38 to 41 are screens that illustrate the balance of the pitch and the stride and the balance of the pace during a running period of a target user. On each of the screens illustrated in FIGS. 38 to 41, a menu 841, a graph 842, and a graph 843 are displayed with being vertically aligned.

In the menu 841, items of "Whole", "Early Stage", "Middle Stage", and "Latter Stage" are included. For example, the running period is classified into three periods of the early stage, the middle stage, and the latter stage at a predetermined ratio. Then, in a case where "Whole" is selected on the menu 841, the balance of the pitch and the stride and the balance of the pace during the whole running period are displayed. In a case where "Early Stage" is selected on the menu 841, the balance of the pitch and the stride and the balance of the pace during the early stage of the running period are displayed. In a case where "Middle Stage" is selected on the menu 841, the balance of the pitch and the stride and the balance of the pace during the middle stage of the running period are displayed. In a case where "Latter Stage" is selected on the menu 841, the balance of the pitch and the stride and the balance of the pace during the latter stage of the running period are displayed.

The graph 842 represents the distribution of the balance of the pitch and the stride during a period designated on the menu 841. For example, the period designated on the menu 841 is divided into units of minutes, and an average value of the pitch-stride balances br of the unit periods is calculated. Then, each unit period is classified into a balanced period, a stride approach period, and a pitch approach period based on the average value of the pitch-stride balances br.

For example, a unit period in which $-th1 \leq$ the average value of pitch-stride balances br$\leq$th1 is classified into the balanced period. In addition, a unit period in which the average value of the pitch-stride balances br>th1 is classified into a stride approach period. A unit period in which the average value of the pitch-stride balances br<-th1 is classified into a pitch approach period. Here, th1 is a predetermined threshold. Then, by forming a ratio among the total times of the periods including the balanced period, the stride approach period, and the pitch approach period within the designated period as a graph, the graph 842 is formed.

By using the graph 842, the target user can easily perceive the balance of the pitch and the stride in each period of the whole running period, the early stage, the middle stage, and the latter stage. In other words, the target user can easily perceive the ratio of neutral running, running inclining toward the stride and running inclining toward the pitch in each period.

The graph 843 illustrates the distribution of paces during a period designated on the menu 841. For example, according to the pace (m/min) within the unit period for each minute inside the period designated on the menu 841, each unit period is classified into a slow period, a fast-running period, a high pace period, or a spurt period.

For example, a unit period in which the pace<the standard speed of the target user×(1−c1) is classified into the slow period. A unit period in which the standard speed of the target user×(1−c1) S the pace≥the standard speed of the target user×(1+c1) is classified into the fast-running period. In addition, a unit period in which the standard speed of the target user×(1+c1)≤the pace≤the standard speed of the target user×(1+c1+c2) is classified into the high-pace period. A unit period of the pace>the standard speed of the target user×(1+c1+c2) is classified into a spurt period. Here, c1 and c2 are predetermined constants. Then, by forming the ratio of the total time among the slow period, the fast-running period, the high-pace period, and the spurt period inside the designated period as a graph, the graph 843 is formed.

By using the graph 843, the target user can easily perceive the distribution of the paces in each period of the whole running period, the early stage, the middle stage, and the latter stage. In other words, the target user, in each period, can easily perceive the ratio among slow running, fast running, high-pace running, and spurt.

Figure 42:
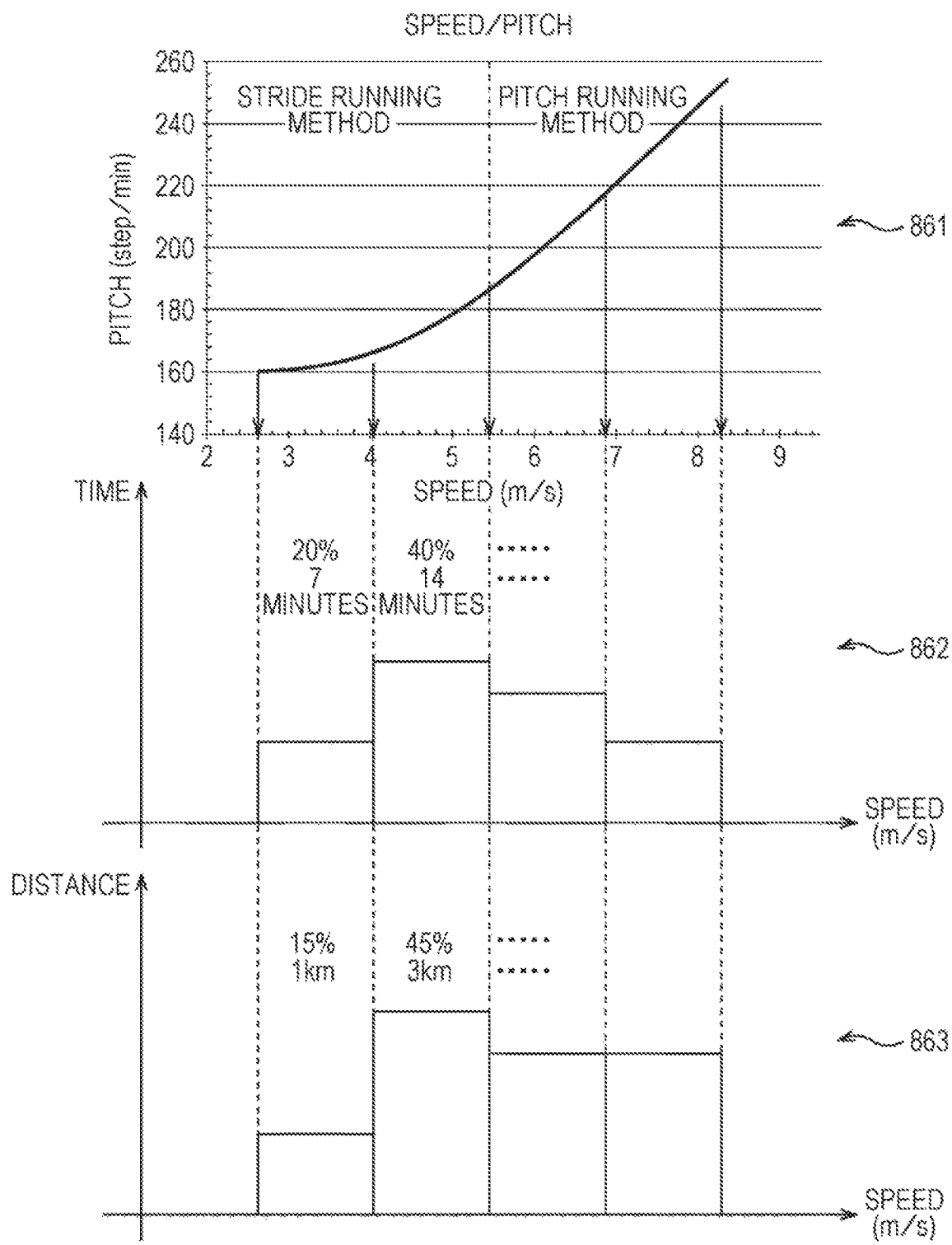
FIG. 42 is a diagram that illustrates a tenth example of the screen presenting an analysis result of a running state.

A screen illustrated in FIG. 42 represents the distribution of speeds during a running period of a target user. On this screen, graphs 861 to 863 are displayed with being vertically arranged.

The graph 861 represents a speed-pitch characteristic curve of the target user. The horizontal axis represents the speed, and the vertical axis represents the pitch. In addition, a stride-pitch switching speed is denoted by a dotted line. It is illustrated that a range lower than the stride-pitch switching speed is a range for the stride running method, and a range faster than the stride-pitch switching speed is a range for the pitch running method.

In this example, the speeds are divided into four ranges by using the stride-pitch switching speed as the reference. More specifically, the range slower than the stride-pitch switching speed is divided into two parts, and the range faster than the stride-pitch switching speed is divided into two parts.

In the graph 862, a time (or the ratio of the time) running at a speed of each range during the running period is represented using a bar graph. In the graph 863, a distance (or the ratio of the distance) running at a speed of each range during the running period is represented using a bar graph.

Accordingly, the target user can easily perceive the distribution of the speeds and the distribution of the stride running method and the pitch running method during the running period.

The number of divisions of the speed range is not limited to this example, but an arbitrary number may be set.

Figure 43:
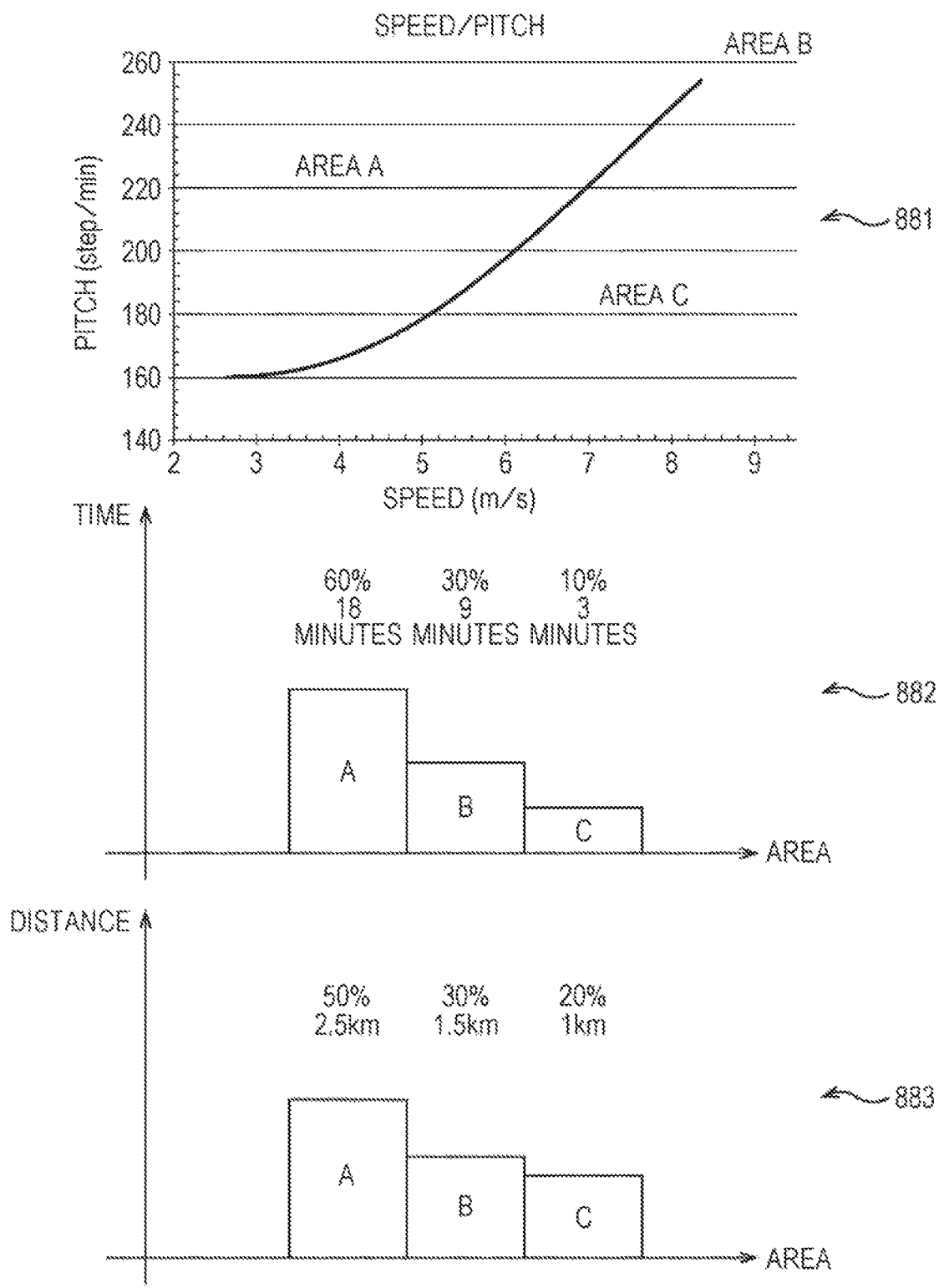
FIG. 43 is a diagram that illustrates an eleventh example of the screen presenting an analysis result of a running state.

A screen illustrated in FIG. 43 represents the distribution of the balance of the pitch and the stride during a running period of a target user. On this screen, graphs 881 to 883 are displayed with being vertically arranged.

The graph 881, similarly to the graph 861 illustrated in FIG. 42, represents the speed-pitch characteristic curve of the target user. On the graph 881, three areas of areas A to C are represented. The area A is an area disposed on a further upper side than the speed-pitch characteristic curve and is an area in which running inclining toward the pitch is performed. The area B is an area disposed on the speed-pitch characteristic curve and is an area in which neutral running is performed.

The area C is an area disposed on a further lower side than the speed-pitch characteristic curve and is an area in which running inclining toward the stride is performed.

In the graph 862, a time (or the ratio of the time) running in each area of the areas A to C during the running period is represented using a bar graph. In the graph 863, a distance (or the ratio of the distance) running in each area of the areas A to C during the running period is represented using a bar graph.

Accordingly, the target user can easily perceive the distribution of the balance of the pitch and the stride during the running period.

The area B may be configured to include not only the area disposed precisely on the speed-pitch characteristic curve but also an area near the speed-pitch characteristic curve.

In this way described above, the target user can acquire the balance of the pitch and the stride of his running.

For example, the target user can acquire the average balance, a balance at the time of a good condition and a balance at the time of a bad condition.

In addition, the target user can intuitively understand the degree of growth of his stride from that at a normal time, the degree of an increase in his pitch from that at a normal time, and the like.

(Data Comparing Process)

Figure 44:
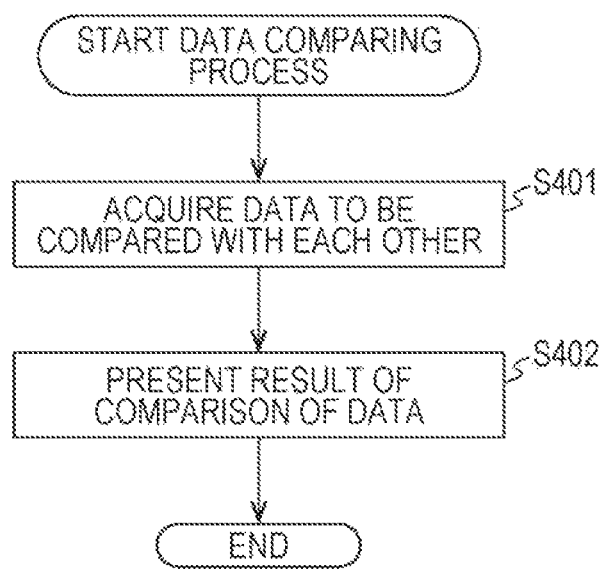
FIG. 44 is a flowchart that illustrates a data comparing process executed by a client.

Next, a data comparing process executed by the client 112 will be described with reference to a flowchart illustrated in FIG. 44. For example, this process is started when a user (hereinafter, referred to as a target user in this process) who is a target for the comparison of data inputs an instruction for executing the data comparing process to the mobile terminal 121 or the wearable terminal 122.

In step S401, the mobile terminal 121 acquires data to be compared with each other. More specifically, the UI control unit 353 of the mobile terminal 121 requests the server 111 to transmit the data to be compared with each other. Then, the UI control unit 353 receives the data transmitted from the server 111 in response to the request.

Here, as a combination of the data to be compared with each other, for example, the running characteristics, the cardiorespiratory capacities, the stamina characteristics, or the running states of the target user for a plurality of time points (for example, a current time point and a past time point or the like) and the running characteristics, the cardiorespiratory capacities, the stamina characteristics, or the running states of a plurality of users (for example, the target user, and other users or the like) may be considered.

In step S402, the mobile terminal 121 presents a result of the comparison of the data, and the data comparing process ends. More specifically, the UI control unit 353 of the mobile terminal 121 generates display data comparing the acquired data and displays a screen for comparing the acquired data on the output unit 306 based on the generated display data. Here, an example of the screen displayed on the output unit 306 will be described with reference to FIGS. 45 to 48.

Figure 45:
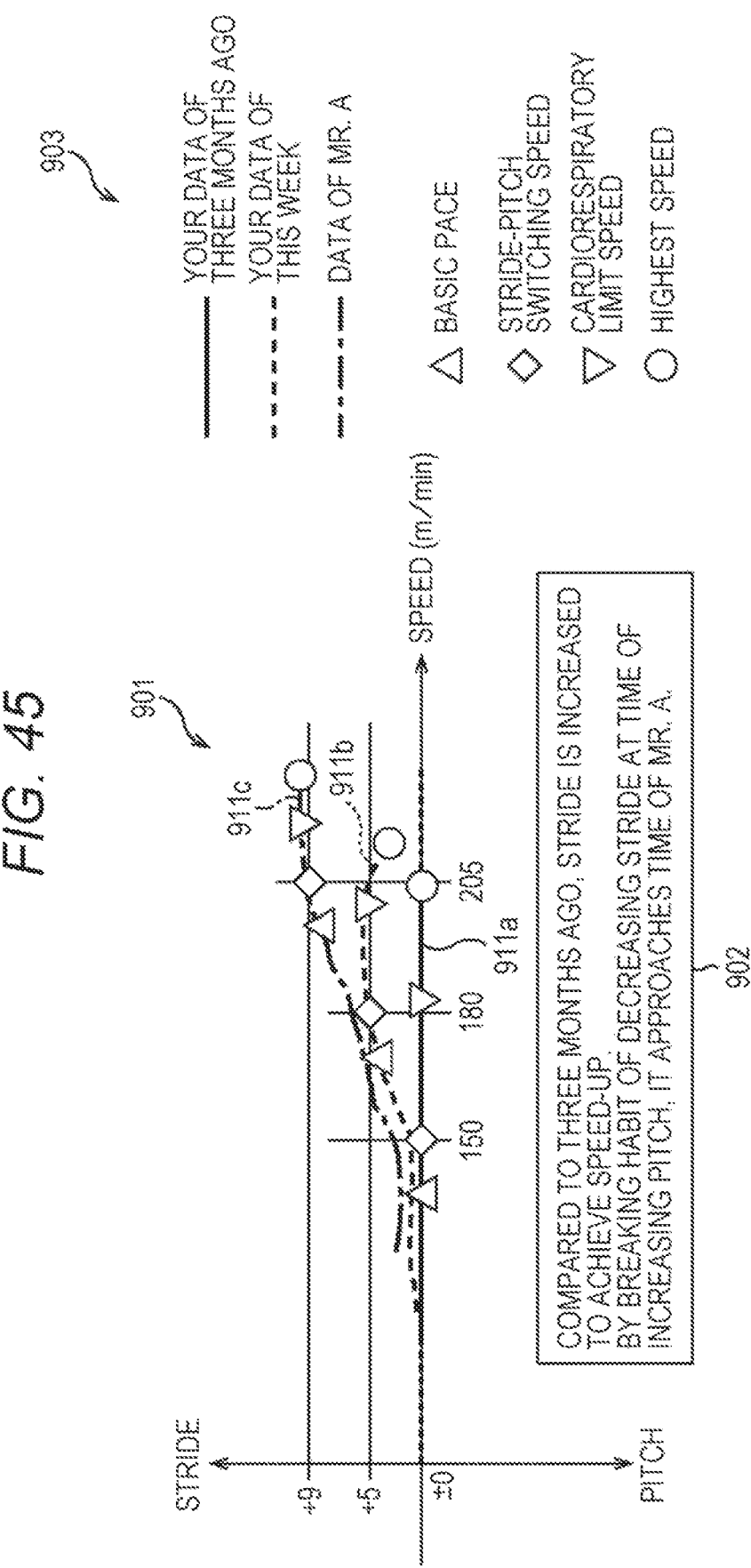
FIG. 45 is a diagram that illustrates a first example of a screen presenting a comparison result of data.

FIG. 45 illustrates an example of the screen that presents a result of the comparison among the speeds and the balances of the pitch and the stride of a target user of this week, the target user of three months ago, and another user A of this week. The data of the target user and the user A of this week, for example, is calculated based on measurement data of one week in the past. The data of the target user of three months ago, for example, is calculated based on measurement data of one week in the past from a date three months before today.

On this screen, a graph 901, a window 902, and explanatory notes 903 are displayed.

The graph 901 is a graph that illustrates the speeds and the balances of the pitch and the stride of the target user of this week and the user A by using the target user of three months ago as the reference. The horizontal axis represents the speed. The vertical axis represents the balance of the stride and the pitch using the target user of three months ago as the reference, does not have a particular unit, and is calculated by using a predetermined equation. More specifically, at each speed, in a case where the stride is longer than that of the target user of three months ago as the reference, and the pitch is smaller than that of the target user of three months ago, the value of the vertical axis is positive. On the other hand, in a case the stride is shorter than that of target user of three months ago, and the pitch is larger than that of target user of three months ago, the value of the vertical axis is negative. In other words, in a case where the target user of this week or the user A performs stride approach running relative to the target user of three months ago, the value of the vertical axis is positive. On the other hand, in a case where the target user of this week or the user A performs pitch approach running relative to the target user of three months ago, the value of the vertical axis is negative.

A line 911a represents data of the target user of three months ago, a line 911b represents data of the target user of this week, and a line 911c represents data of the user A of this week. As illustrated in the exemplary notes 903, on the lines 911a to 911c, each upward triangle represents a basic pace, each rhombus represents a stride-pitch switching speed, a downward triangle represents a cardiorespiratory limit speed, and a circle represents a highest speed.

Here, the basic speed, for example, is a speed having a highest frequency in a histogram representing the distribution of the speeds measured during a target period. For example, instead of the basic pace, the standard speed may be displayed.

When a mark of any one of upward triangles, rhombuses, downward triangles, and circles on the lines 911a to 911c is designated, a numerical value representing the balance of the pitch and the stride at a speed corresponding to the designated mark is displayed on the vertical axis of the graph 901. For example, when a mark of a rhombus is designated, a numerical value representing the balance of the pitch and the stride of the target user of this week at the stride-pitch switching speed and a numerical value representing the balance of the pitch and the stride of the user A of this week at the stride-pitch switching speed are displayed.

By using the graphs 901, the target user can easily perceive a change of his running. In other words, the target user can easily perceive changes of the current basic pace, the current stride-pitch switching speed, the current cardiorespiratory limit speed, and the current highest speed relative to those of the past. In other words, at each speed, the target user can easily perceive whether stride approach running or pitch approach running relative to that of the past is performed.

In addition, the target user can easily compare his running with the other user's running. In other words, the target user can easily compare the basic speed, the stride-pitch switching speed, the cardiorespiratory limit speed, and the highest speed of his with those of the other users. Furthermore, at each speed, the target user can easily perceive whether stride approach running or pitch approach running relative to that of the other user is performed.

Inside the window 902, a message for the target user is displayed. For example, as illustrated in this example, description of a change in the running state of the target user from that of three months ago, a specific advice for shortening the running time or allowing his running time to approach the running time of the other user, and the like are displayed. Accordingly, the target user can specifically understand desirable training or desirable target running in the future or the like.

Figure 46:
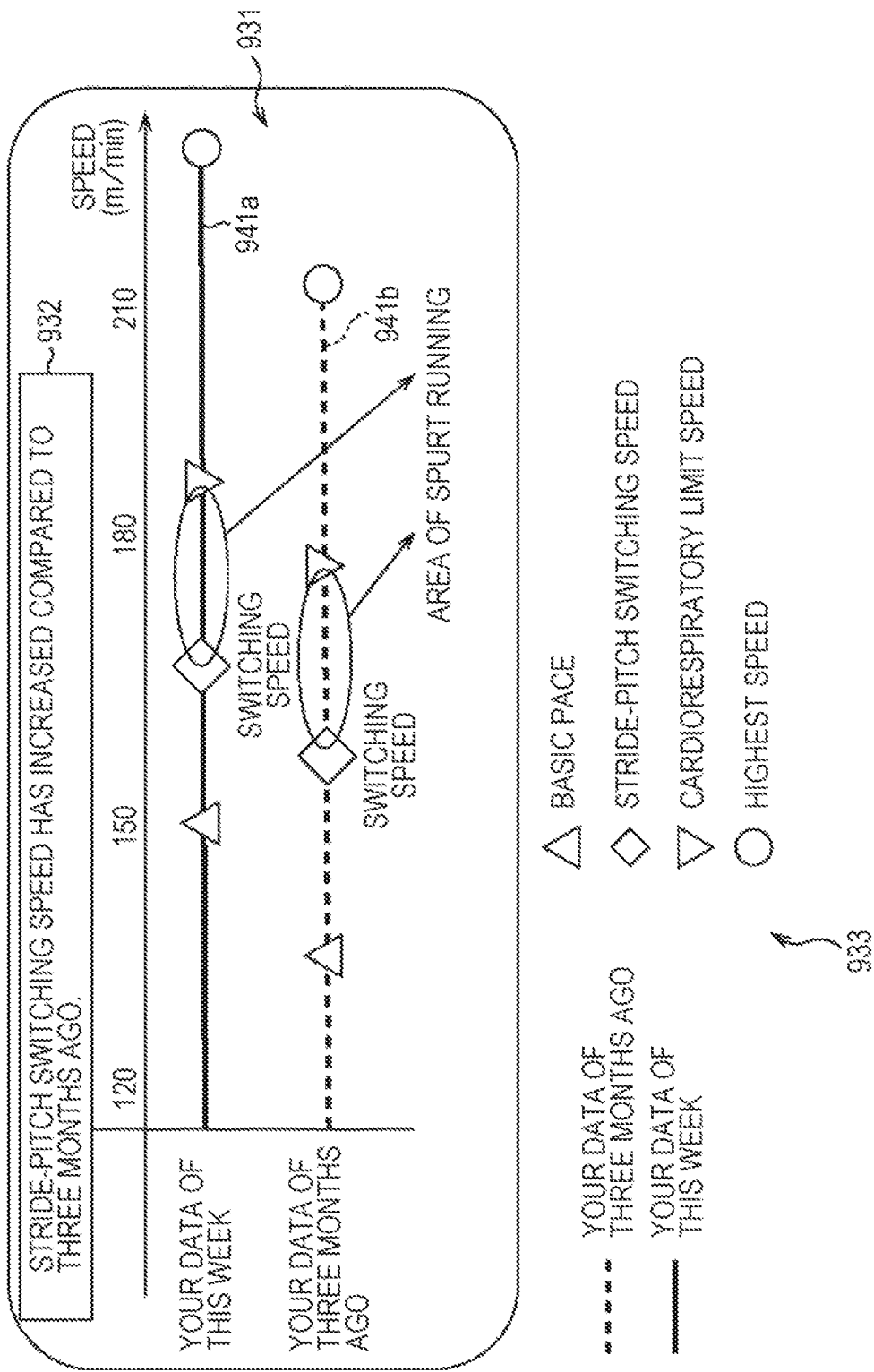
FIG. 46 is a diagram that illustrates a second example of the screen presenting a comparison result of data.

FIG. 46 illustrates an example of a screen that presents a result of a comparison between speeds of the target user of this week and the target user of three months ago. On this screen, a graph 931, a window 932, and explanatory notes 933 are displayed.

The graph 931 is a graph comparing the speeds of the target user of this week and the target user of three months ago with each other. The horizontal axis represents the speed.

A line 941a represents the speed of the target user of this week, and a line 941b represents the speed of the target user of three months ago. As illustrated in the exemplary notes 933, on the lines 941a and 941b, each upward triangle represents a basic pace, each rhombus represents a stride-pitch switching speed, a downward triangle represents a cardiorespiratory limit speed, and a circle represents a highest speed.

Areas of the lines 941a and 941b enclosed by circles are areas between the stride-pitch switching speed and the cardiorespiratory limit speed and represent speeds of a case where the target user performs a spurt.

By using the graphs 931, the target user can easily perceive a change of his speed. In other words, the target user can easily perceive changes of the current basic pace, the current stride-pitch switching speed, the current cardiorespiratory limit speed, and the current highest speed relative to those of the past.

In addition, the target user can recognize a relation between his basic pace and the stride-pitch switching speed. Accordingly, for example, in a case where the basic pace and the stride-pitch switching speed are separated from each other, the target user can acquire information of insufficiency of the cardiorespiratory capacity maintaining the basic pace and the like.

Inside the window 932, a message for the target user is displayed. In this example, description of a change in the running state of the target user from that of three months ago is displayed. More specifically, it is illustrated that the stride-pitch switching speed of the target user is higher than that of three months ago.

The display contents of the window 902 illustrated in FIG. 45 and the window 932 illustrated in FIG. 46 are examples, and the display contents may be freely changed based on a change in the running of the target user and the like. For example, a message describing a change in the running such as "More stride approach running is performed at the same pace.", "The basic speed has been raised.", "The speed of the spurt has been raised.", or "The cardiorespiratory capacity has been increased" may be displayed.

In addition, for example, an advice such as "Let's increase the stride at the basic pace!", "Since the balance of the pitch and the stride is good, let's increase the distance!", or "Since the balance of the pitch and the stride is good, let's increase the pace!" may be displayed.

FIG. 47 illustrates an example of a screen that presents a result of a comparison between the running of a target user of this week with the running characteristic of the target user of three months ago. On this screen, a graph 961 and a window 962 are displayed.

In the graph 961, the horizontal axis represents the speed, and the vertical axis represents the stride. In the graph 961, the speed-stride characteristic curve of the target user of three months ago is represented. In addition, actually-measured values of the speed and the pitch of the target user of this week are denoted by black circles.

Inside the window 962, an index representing the balance of the pitch and the stride of the target user is displayed. This index, for example, at each speed, represents whether the target user performs more stride dominance running or pitch dominance running than three months ago. For example, in a case where the target user designates one of the actually-measured values denoted by the black circles in the graph 961, the value of an index at the speed is displayed inside the window 962.

The value of the index is a positive value in a case where, at the speed designated by the target user, the stride is larger than that of three months ago, and the pitch is smaller than that of three months ago, in other words, in a case where the running of this week is more stride-dominant than that of three months ago. As an increase in the stride becomes large, the value of the index increases. On the other hand, the value of the index is a negative value in a case where, at the speed designated by the target user, the stride is smaller than that of three months ago, and the pitch is larger than that of three months ago, in other words, in a case where the running of this week is more pitch-dominant than that of three months ago. In addition, as a decrease in the stride becomes large, the value of the index decreases.

By using this screen, the target user can easily perceive a change in his running characteristic. In other words, the target user can easily perceive whether his stride is larger or smaller than that of the past and the like.

Figure 48:
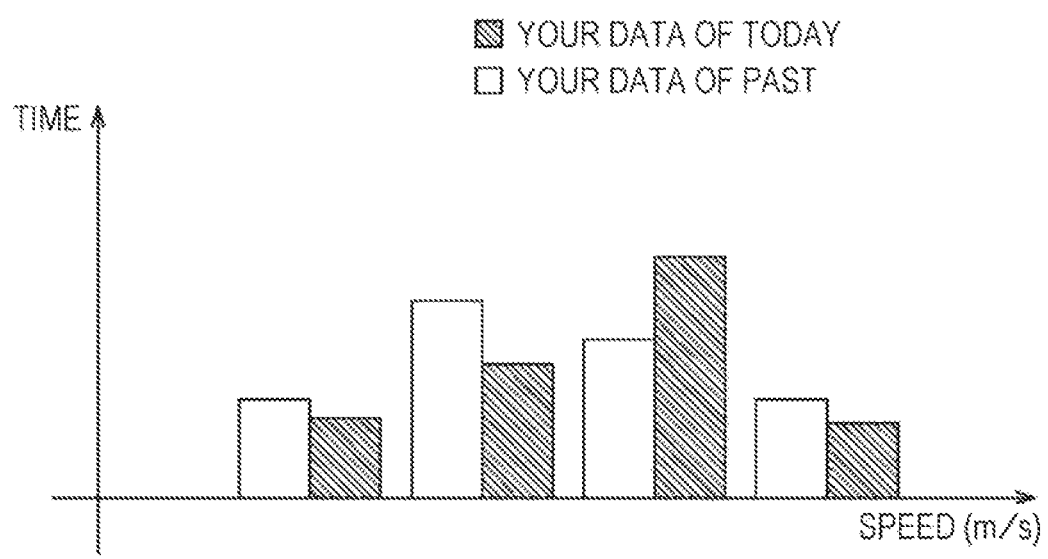
FIG. 48 is a diagram that illustrates a fourth example of the screen presenting a comparison result of data.

FIG. 48 illustrates an example of a screen presenting a result of a comparison of the distributions of the speeds of the target user of the past and the present. For example, on this screen, graphs of the past and the present similar to the graph 862 illustrated in FIG. 42 are displayed in parallel with each other. Here, white bars represent the distribution of speeds of the target user in the past, and bars of a diagonal-line pattern represent the distribution of the speeds of the target user at present.

By using this screen, the target user can easily perceive a change in the distribution of speeds and a change in the distribution of the stride running method and the pitch running method.

For example, graphs of the past and the present similar to the graph 863 illustrated in FIG. 42 may be displayed in parallel with each other.

In addition, for example, graphs of the past and the present similar to the graph 882 illustrated in FIG. 43 may be displayed in parallel with each other, or graphs of the past and the present similar to the graph 883 illustrated in FIG. 43 may be displayed in parallel with each other. Accordingly, the target user can easily perceive a change in the balance of the pitch and the stride.

In this way described above, the target user, by comparing his data of the present and the past with each other, can easily acquire the achievement of the training and changes in the stability, the habit, and the like of his running.

In addition, by comparing his data with data of the other user, the target user may refer to the running of other person or specifically perceive a difference in the habit of the running between the other person and the target user.

Furthermore, the target user can easily perceive a part of his running to be increased and a desirable direction in which the part is to be is increased. For example, the target user can perceive one of training for increasing the stride, training for increasing the pitch, and training for improving the cardiorespiratory capacity to be focused on.

In the examples illustrated in FIGS. 45 to 48, the combination of data to be compared with other and the number of units of the data are examples, and any other combination or the number of units may be set. For example, the data of the target user and data of other two or more users may be compared with each other, and the present data of the target user and two or more units of past data of the target user may be compared with each other. In addition, for example, present or past data of the target user and past data of the other user may be compared with each other.

The user who is a comparison target may be designated by the target user or may be automatically selected by the server 111. In the latter case, for example, the server 111 selects a user who is similar to the target user and is superior to the target user in running as a comparison target. More specifically, for example, the server 111 selects a user, at the same speed, having a stride longer than that of the target user and having a basic pace and a cardiorespiratory limit speed higher than those of the target user as a comparison target from among users belonging to a cluster having the same speed-pitch-stride characteristic as the target user.

In this way, by selecting a user who is similar to the target user and is superior to the target user in running as the comparison target, the target user can be urged to compete with the user, and the target user can easily set a clear goal.

In addition, not a specific user but an average value of a plurality of users may be set as a comparison target. For example, an average of users belonging to the same cluster as that of the target user, an average value of users belonging to a cluster that is slightly superior to the target user in running, or the like may be set as the comparison target.

(Running Parameter Control Training Support Process)

Next, a running parameter control training support process executed by the client 112 will be described with reference to a flowchart illustrated in FIG. 49. Here, the running parameter control training, for example, is training in which one parameter among the pitch, the stride, and the speed is fixed, and the other parameters are changed.

This process is started, for example, when a user (hereinafter, referred to as a target user in this process) performing running parameter control training inputs an instruction for starting training to the mobile terminal 121 or the wearable terminal 122. This process ends, for example, when the target user inputs an instruction for ending the training to the mobile terminal 121 or the wearable terminal 122 or when it is timing for ending the training.

Figure 31:
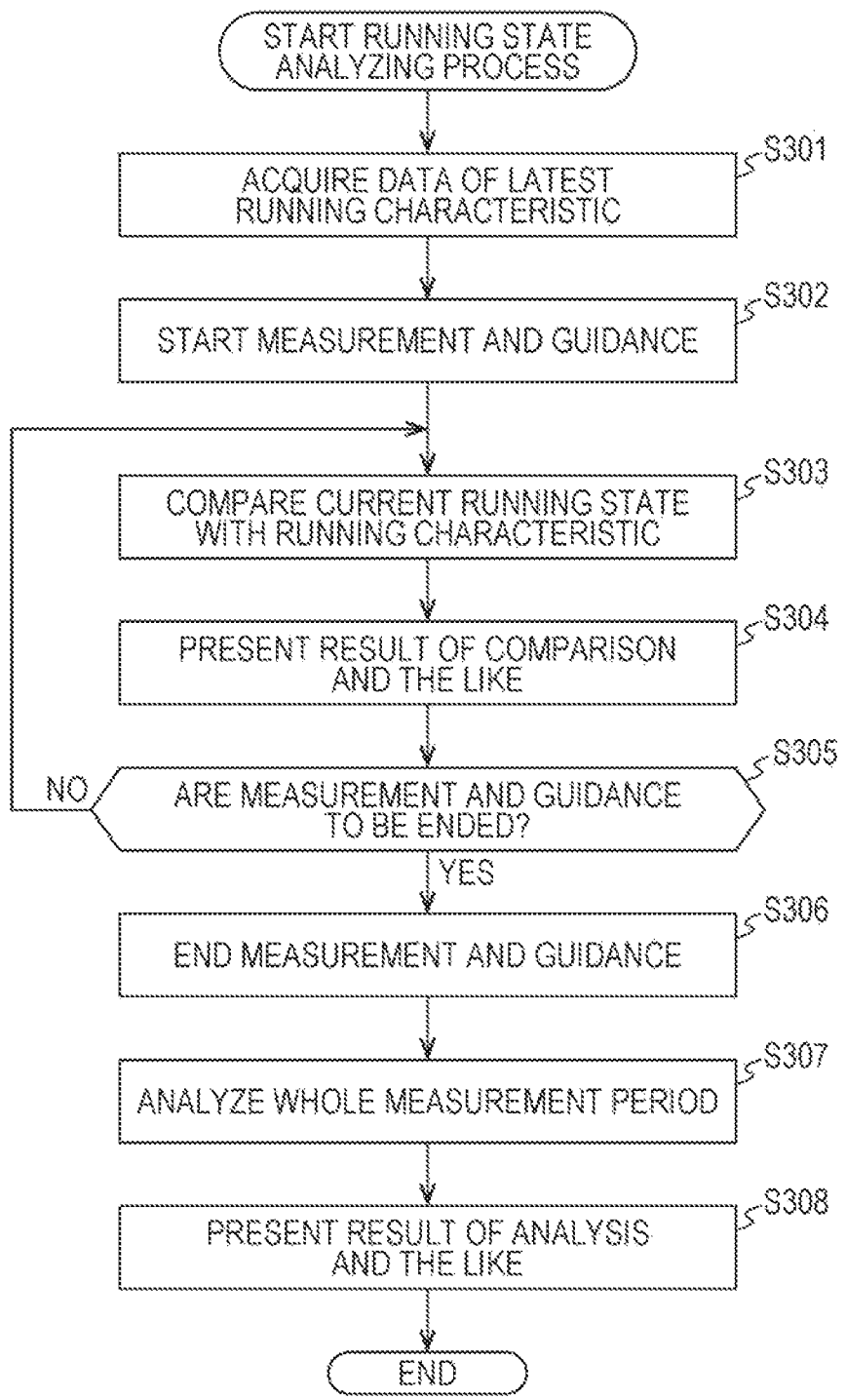
FIG. 31 is a flowchart that illustrates a running state analyzing process executed by a client.

In step S501, similarly to the process of step S301 illustrated in FIG. 31 described above, data of the latest running characteristic is acquired.

In step S502, the client 112 starts measurement. More specifically, the running state analyzing unit 361 of the mobile terminal 121 instructs the wearable terminal 122 to start measurement. The data collecting unit 471 of the wearable terminal 122 starts collecting measurement data acquired by each device of the measurement unit 406 and transmitting the collected measurement data to the mobile terminal 121.

The running state analyzing unit 361 starts calculating a speed, a pitch, and a stride based on the received measurement data. In addition, the running state analyzing unit 361 starts storing the measurement data of the speed, the pitch, the stride, the heart rate, and the like of the target user in the storage unit 302.

In addition, the running state analyzing unit 361 starts transmitting the measurement results of the speed, the pitch, the stride, the heart rate, and the pitch-stride balance br of the target user, environment information at the time of the measurement, user information, and the like to the server 111. At this time, the transmitted measurement results and the like are stored in the server 111 and, for example, are used for analyzing the running characteristic, the cardiorespiratory capacity, and the stamina characteristic of the target user.

The running state analyzing unit 361 may be configured to transmit the measurement results and the like to the server 111 altogether later.

In step S503, the client 112 guides the target user to run at the standard speed. More specifically, the guide unit 352 of the mobile terminal 121 notifies the wearable terminal 122 of the start of the running parameter control training. The output unit 405 of the wearable terminal 122, for example, outputs a voice message of "From now on, training will be performed in which the pitch is changed with the stride maintained.", thereby notifying the target user of the start of the running parameter control training.

Next, the guide unit 352 of the mobile terminal 121 instructs the wearable terminal 122 to guide the target user to standard-speed running. The output unit 405 of the wearable terminal 122, for example, outputs a voice message of "First, please run at a pace for running in the best condition for the time being!", thereby urging the target user to perform standard-speed running.

In step S504, the guide unit 352 of the mobile terminal 121 determines whether or not the speed of the target user arrives near the standard speed. The determination process of step S504 is repeatedly executed until it is determined that the speed of the target user arrives near the standard speed, and in a case where the speed of the target user is determined to have arrived near the standard speed, the process proceeds to step S505.

In step S505, the client 112 performs guiding such that a predetermined parameter is maintained to be constant, and another parameter is changed. For example, the guide unit 352 of the mobile terminal 121 performs guiding through the wearable terminal 122 such that the stride is increased or decreased by a predetermined value with the current pitch maintained. Alternatively, the guide unit 352 of the mobile terminal 121 performs guiding through the wearable terminal 122 such that the pitch is increased or decreased by a predetermined value with the current stride maintained. Alternatively, the guide unit 352 of the mobile terminal 121 performs guiding through the wearable terminal 122 such that a combination of the stride and the pitch is changed with the current speed maintained. The method of guiding the pitch and the stride is similar to the method described above.

For example, in a case where the pitch and the speed are changed while the stride is maintained to be constant, the output unit 405 of the wearable terminal 122 outputs a voice message of "From now on, the pitch will be changed. Please run according to a sound while paying attention to no change in the stride!". Then, in a case where the stride is shortened, the output unit 405, for example, outputs a voice message of "The stride is slightly shortened. Please increase the stride more!", thereby guiding the stride to be returned to the original value. On the other hand, in a case where the stride is lengthened, the output unit 405, for example, outputs a voice message of "The stride is lengthened. Please decrease the stride with the pitch maintained", thereby guiding the stride to be returned to the original value.

In step S506, the guide unit 352 of the mobile terminal 121 determines whether or not the kind of the parameter maintained to be constant is changed. In a case where the kind of the parameter maintained to be constant is determined not to be changed, the process is returned to step S505.

Thereafter, in step S506, until the kind of parameter maintained to be constant is determined to be changed, the process of steps S505 and S506 is repeatedly executed.

On the other hand, in step S506, in a case where the kind of parameter maintained to be constant is determined to be changed, the process is returned to step S503, and the process of step S503 and subsequent steps are executed. For example, when it is timing when the kind of parameter maintained to be constant is changed in a training program set in advance or when the target user inputs an instruction for changing the kind of parameter maintained to be constant to the mobile terminal 121 or the wearable terminal 122, the parameter maintained to be constant is determined to be changed.

Here, a specific example of the running parameter control training will be described with reference to FIGS. 50 to 53.

Figure 50:
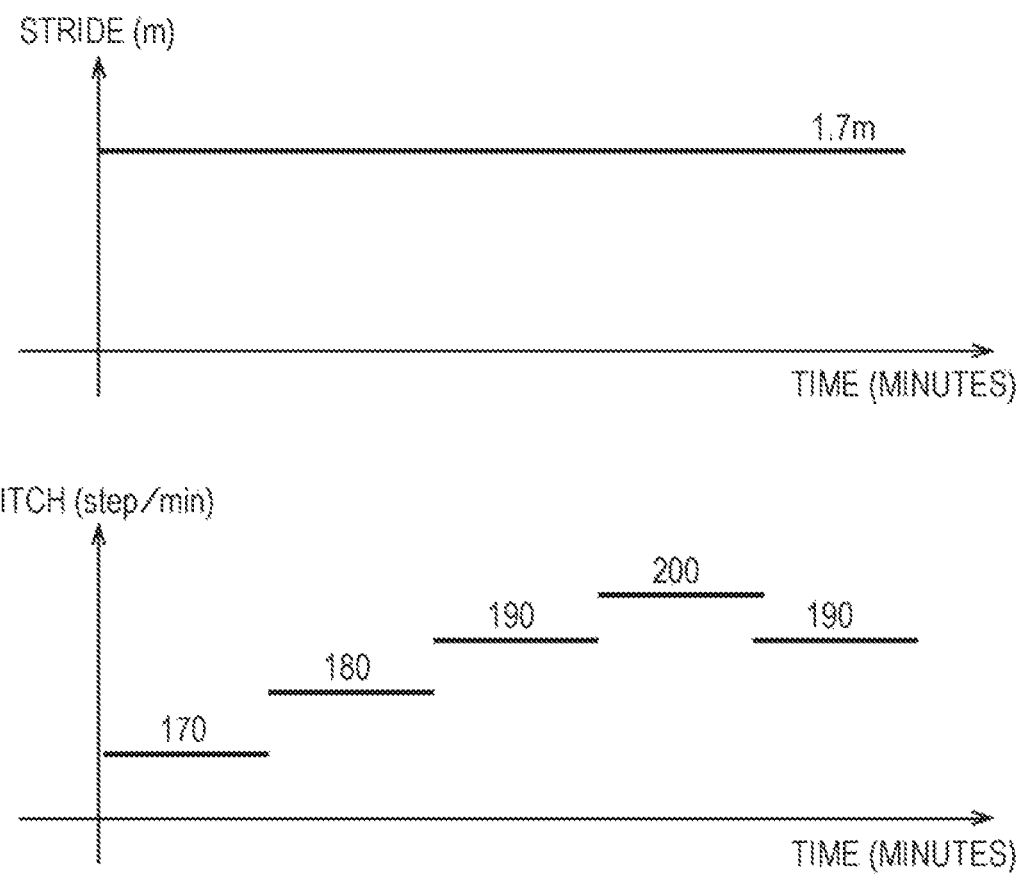
FIG. 50 is a diagram that illustrates an example of the running parameter control training support process.

FIG. 50 illustrates a specific example of a training method changing the pitch with the stride maintained to be constant. In an upper graph, the horizontal axis represents the time, the vertical axis represents the stride, and a transition of the stride during the training is illustrated. In a lower graph, the horizontal axis represents the time, the vertical axis represents the pitch, and a transition of the pitch during the training is illustrated.

In this example, an example is illustrated in which the pitch is changed to 170 step/min, 180 step/min, 190 step/min, 200 step/min, and 190 step/min with the stride of the target user maintained to be 1.7 m.

FIG. 51 illustrates a specific example of a training method changing the stride with the pitch maintained to be constant. In an upper graph, the horizontal axis represents the time, the vertical axis represents the stride, and a transition of the stride during the training is illustrated. In a lower graph, the horizontal axis represents the time, the vertical axis represents the pitch, and a transition of the pitch during the training is illustrated.

In this example, an example is illustrated in which the stride is changed to 1.4 m, 1.9 m, 1.5 m, 1.6 m, and 1.4 m with the pitch of the target user maintained to be 170 step/min.

Figure 52:
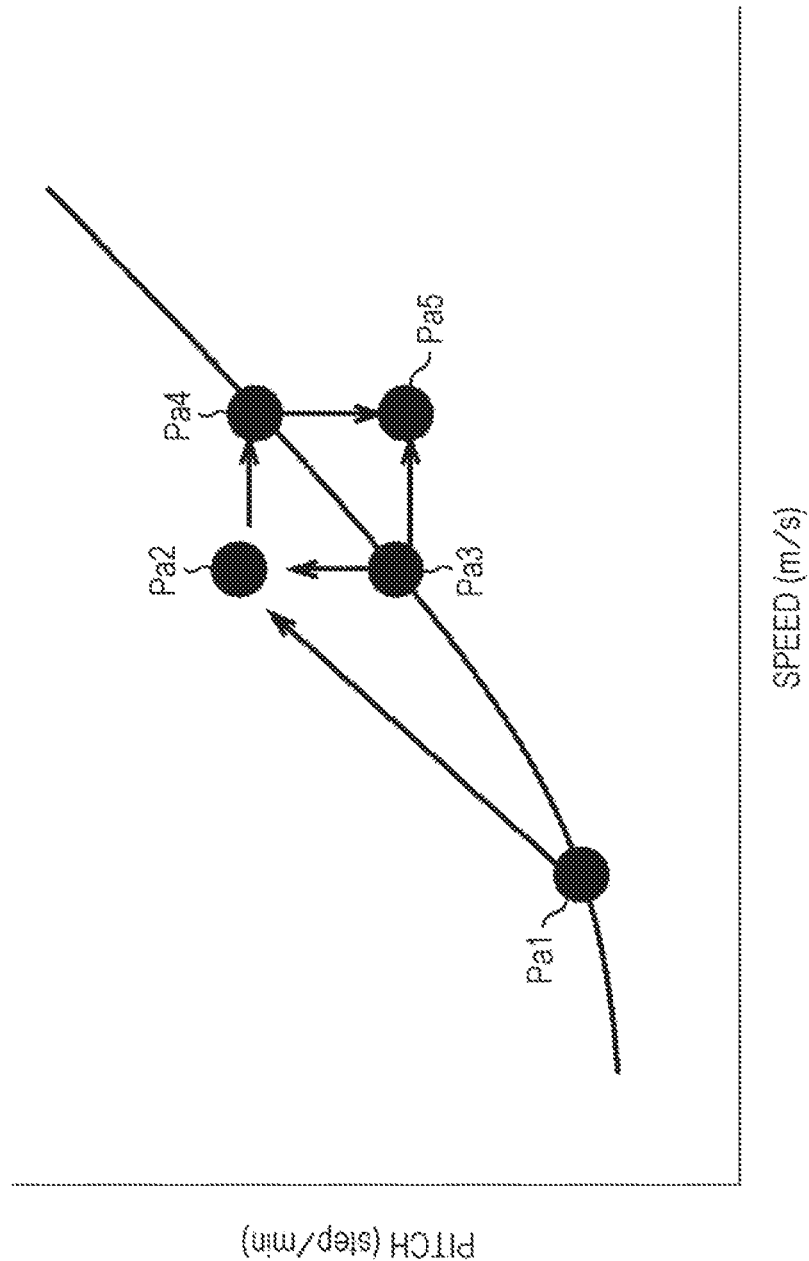
FIG. 52 is a diagram that illustrates an example of the running parameter control training support process.
Figure 53:
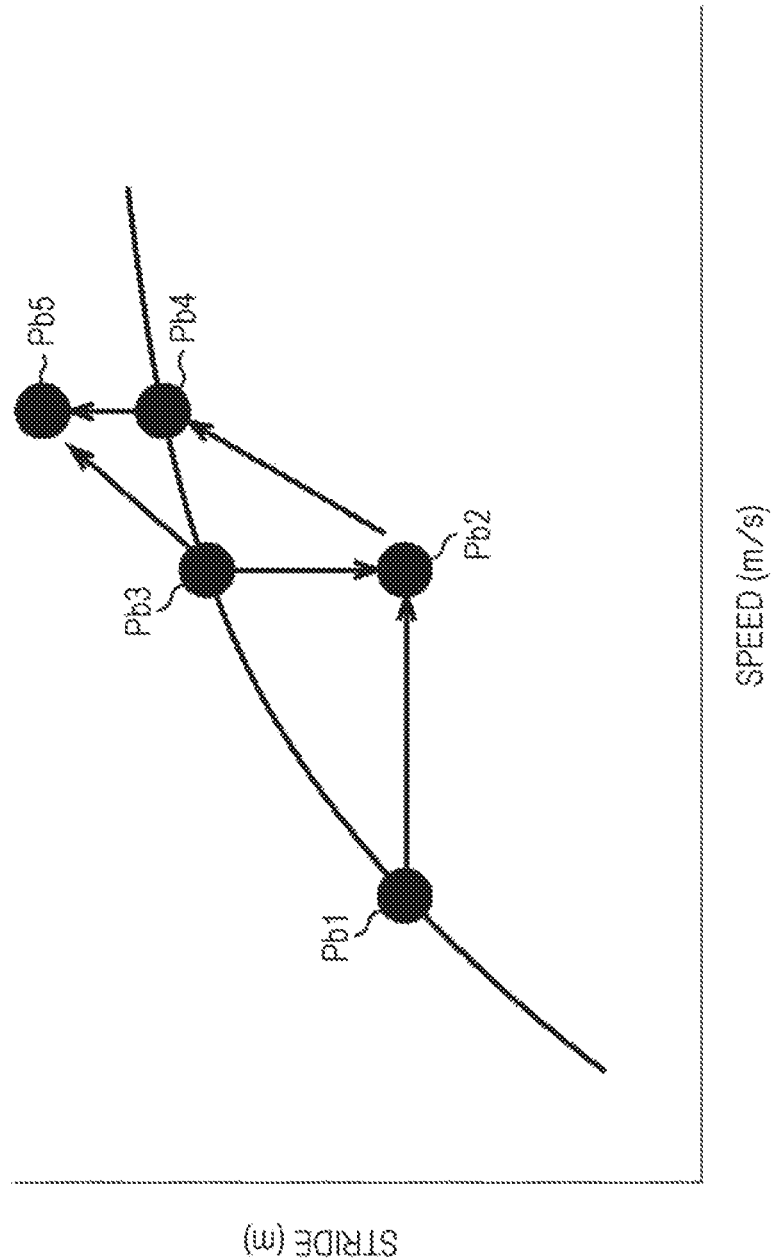
FIG. 53 is a diagram that illustrates an example of the running parameter control training support process.

FIGS. 52 and 53 illustrate variations of the running parameter control training. FIG. 52 illustrates an example of a speed-pitch characteristic curve of a target user. In FIG. 52, the vertical axis represents the speed, and the horizontal axis represents the pitch. FIG. 53 illustrates an example of a speed-stride characteristic curve of a target user. In FIG. 53, the vertical axis represents the speed, and the horizontal axis represents the pitch.

For example, the guide unit 352 guides movement from a point Pa1 disposed on the speed-pitch characteristic curve to a point Pa2 and movement from a point Pb1 disposed on the speed-stride characteristic curve to a point Pb2. Accordingly, the target user can perform training for increasing the pitch and the speed with the stride being maintained.

In addition, for example, the guide unit 352 guides movement from a point Pa3 disposed on the speed-pitch characteristic curve to a point Pa2 and movement from a point Pb3 disposed on the speed-stride characteristic curve to a point Pb2. Accordingly, the target user can perform training for increasing the pitch and shortening the stride with the speed being maintained.

In addition, for example, the guide unit 352 guides movement from a point Pa2 to a point Pa4 disposed on the speed-pitch characteristic curve and movement from a point Pb2 to a point Pb4 disposed on the speed-stride characteristic curve. Alternatively, for example, the guide unit 352 guides movement from a point Pa3 disposed on the speed-pitch characteristic curve to a point Pa5 and movement from a point Pb3 disposed on the speed-stride characteristic curve to a point Pb5. Accordingly, the target user can perform training for increasing the stride and raising the speed with the pitch being maintained.

In addition, for example, the guide unit 352 guides movement from a point Pa4 disposed on the speed-pitch characteristic curve to a point Pa5 and movement from a point Pb4 disposed on the speed-stride characteristic curve to a point Pb5. Accordingly, the target user can perform training for increasing the stride and decreasing the pitch with the speed being maintained.

In this way described above, the target user can perform training with various combinations of the pitch and the stride. Accordingly, for example, the target user can perform effective training for pushing up the limit value of a predetermined parameter. For example, until now, when the target user increases the pitch up to the spurt area, the stride is decreased. However, the target user can perform training for increasing the pitch with the stride maintained. As a result, the target user can increase the efficiency of the spurt.

In addition, for example, until now, in a case where the speed is raised, the running method is switched to the pitch running method, and the stamina is not continued. The target user can perform training for increasing the stride with the pitch being maintained. As a result, the target user can apply the stride running method for increasing the time to his body.

Furthermore, the target user, for example, can find a combination having efficiency higher than a combination of a pitch and a stride that is inadvertently selected. Then, the target user performs training for running with a combination of a pitch and a stride having high efficiency, thereby allowing a new running characteristic to be memorized in his body.

While an example is illustrated in which standard-speed running is guided in step S503, the guide unit 352 may guide the running to a speed other than the standard speed. For example, the guide unit 352 may guide running to a speed that was attainable for the target user on a training menu of the past or a speed that is slightly higher than the speed based on the result data of the training of the target user that was acquired in the past. In such a case, the standard speed of the target user can be raised little by little.

For example, training for allowing a user to run at an arbitrary speed without guiding the user to a specific speed in step S503 and changing the stride or the pitch with the speed at that time maintained may be performed. In such a case, training matching the condition of the target user can be performed.

In addition, during the training or after the training, a graph representing the transitions of the speed, the pitch, and the stride during the training may be presented to the target user for visualizing the result of the training. In addition, for example, a graph representing the transitions of the speed, the pitch, and the stride in training performed in the past may be presented together for a comparison.

(Heart Rate Maintaining Training Support Process)

Figure 54:
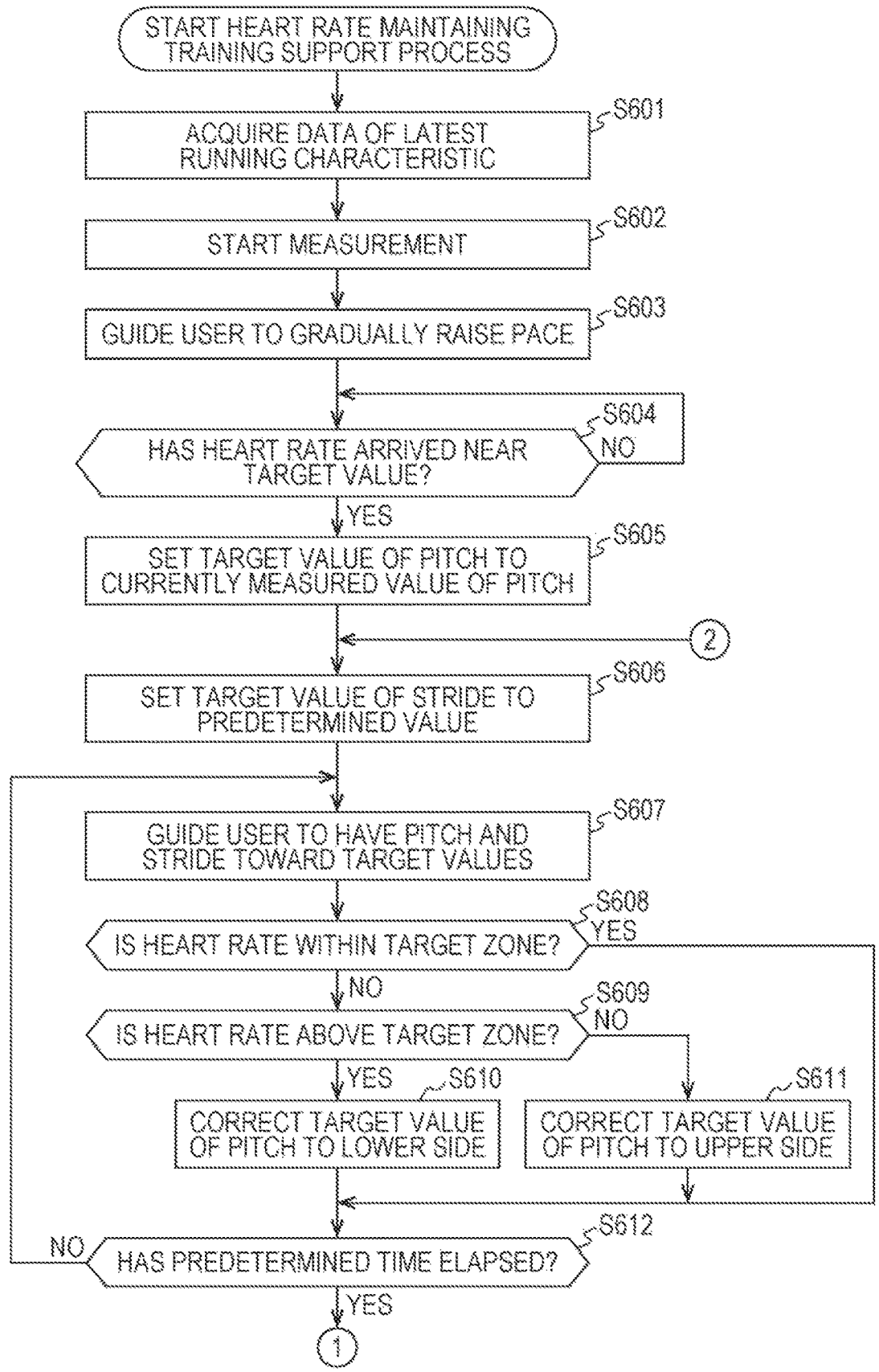
FIG. 54 is a flowchart that illustrates a heart rate maintaining training support process executed by a client.
Figure 55:
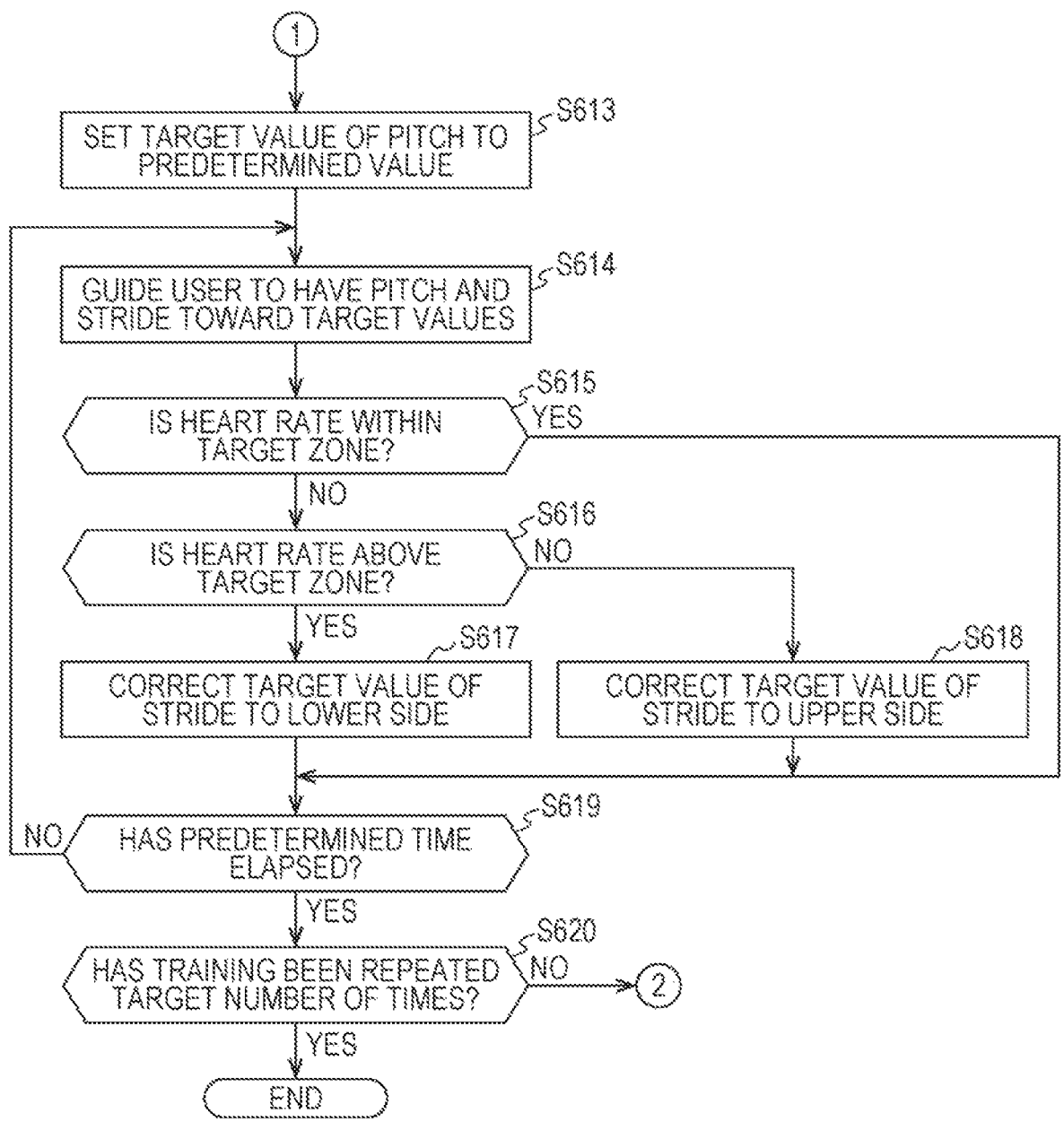
FIG. 55 is a flowchart that illustrates the heart rate maintaining training support process executed by the client.
Figure 56:
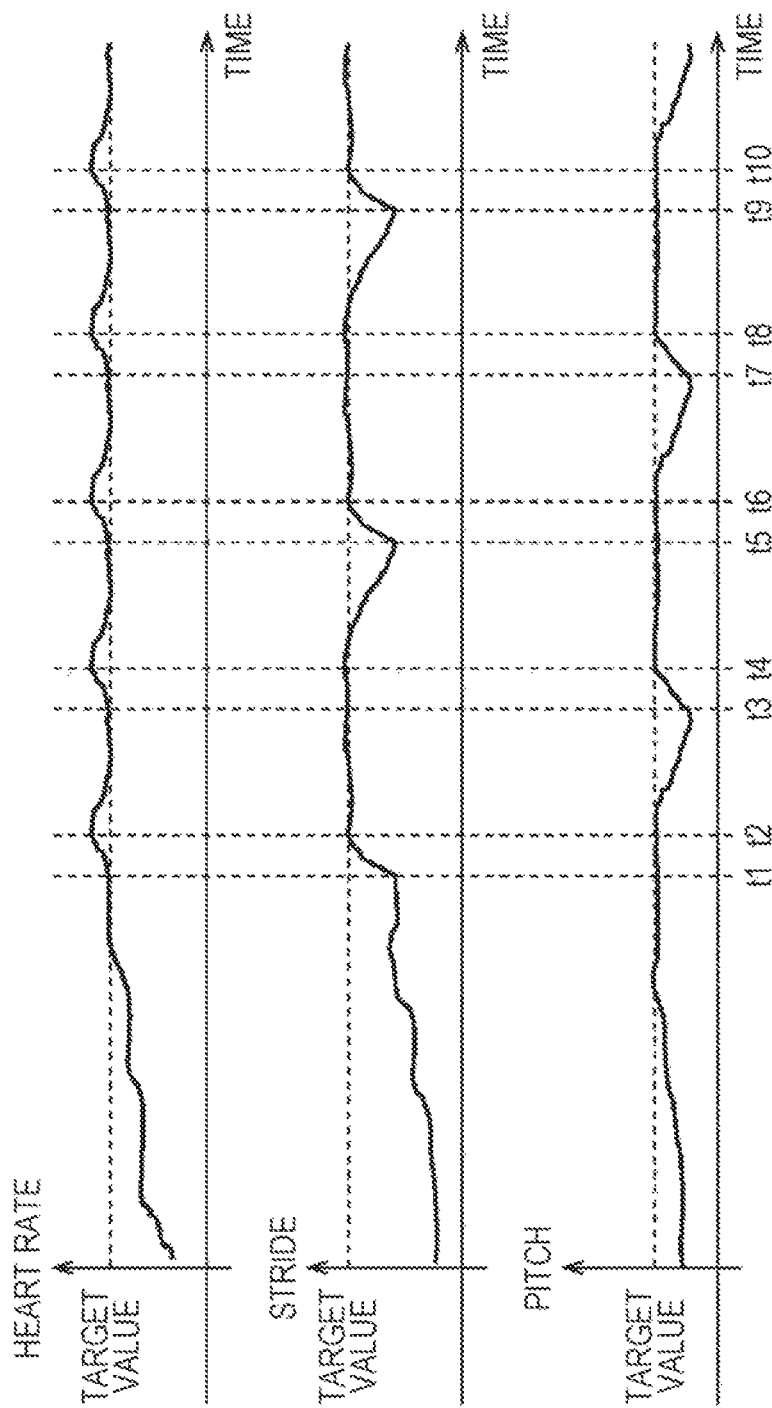
FIG. 56 is a diagram that illustrates an example of the heart rate maintaining training support process.

Next, a heart rate maintaining training support process executed by the client 112 will be described with reference to flowcharts illustrated in FIGS. 54 and 55 and a timing diagram illustrated in FIG. 56. Here, the heart rate maintaining training is training for changing the pitch and the stride with the heart rate maintained to be constant. The timing diagram illustrated in FIG. 56 illustrates the transitions of the time series of the heart rate, the stride, and the pitch during heart rate maintaining training.

This process is started, for example, when a user (hereinafter, referred to as a target user in this process) performing the heart rate maintaining training inputs an instruction for starting training to the mobile terminal 121 or the wearable terminal 122.

In step S601, similarly to the process of step S301 illustrated in FIG. 31, data of the latest running characteristic is acquired.

Figure 49:
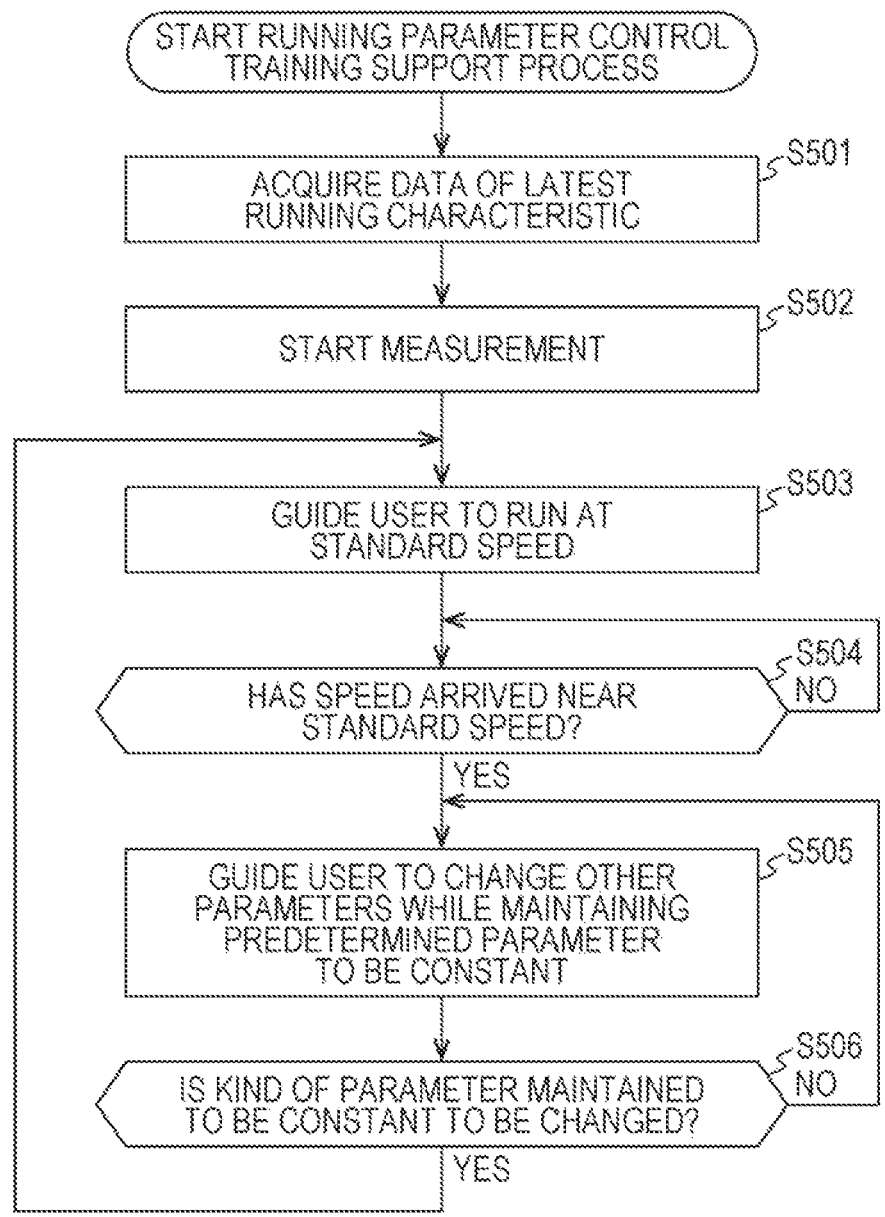
FIG. 49 is a flowchart that illustrates a running parameter control training support process executed by a client.

In step S602, similarly to the process of step S502 illustrated in FIG. 49, measurement is started.

In step S603, the client 112 guides the target user to gradually raise the pace. More specifically, the guide unit 352 of the mobile terminal 121 notifies the wearable terminal 122 of the start of the heart rate maintaining training. The output unit 405 of the wearable terminal 122, for example, outputs a voice message of "From now on, training will be performed in which the pitch and the stride are increased with the heart rate maintained to be constant.", thereby notifying the target user of the start of the heart rate maintaining training.

Next, the guide unit 352 of the mobile terminal 121 performs guiding such that the pace of the target user is gradually raised by using the guiding method described above through the wearable terminal 122. At this time, for example, the output unit 405 of the wearable terminal 122 outputs a voice message of "First, please gradually raise the pace according to a sound.". In addition, at this time, in a case where the speed of the target user is lower than the stride-pitch switching speed, the stride of the target user is guided to be gradually increased. On the other hand, in a case where the speed of the target user is the stride-pitch switching speed or higher, the pitch of the target user is guided to be gradually increased.

In step S604, the guide unit 352 of the mobile terminal 121 determines whether or not the heart rate of the target user arrives near a target value set in advance. The determination process of step S604 is repeatedly executed until it is determined that the heart rate of the target user arrives near the target value.

On the other hand, in step S604, in a case where it is determined that the heart rate of the target user arrives near the target value, the process proceeds to step S605. For example, at time t1 illustrated in FIG. 56, the heart rate of the target user is determined to have arrived near the target value, and the process proceeds to step S605.

In step S605, the guide unit 352 of the mobile terminal 121 sets the target value of the pitch to a measured value of the current pitch.

In step S606, the guide unit 352 of the mobile terminal 121 sets the target value of the stride to a predetermined value.

In step S607, the guide unit 352 of the mobile terminal 121 guides the pitch and the stride toward the target values through the wearable terminal 122 by using the guiding method described above.

For example, the output unit 405 of the wearable terminal 122 outputs a voice message of "The heart rate arrives at the target heart rate. The program will be started" and, next, outputs a voice message of "Please intentionally increase the stride".

In step S608, the guide unit 352 of the mobile terminal 121 determines whether or not the heart rate is within a target zone. The target zone, for example, is set within a predetermined range having the target value of the heart rate as its center. In a case where the heart rate is determined to be out of the target zone, the process proceeds to step S609.

In step S609, the guide unit 352 of the mobile terminal 121 determines whether or not the heart rate is above the target zone. In a case where the heart rate is determined to be above the target zone, the process proceeds to step S610.

In step S610, the guide unit 352 of the mobile terminal 121 corrects the target value of the pitch to the lower side so as to lower the heart rate of the target user. For example, like at time t2 illustrated in FIG. 56, in a case where the heart rate is far above the target value, the target value of the pitch is corrected to the lower side. Thereafter, the process proceeds to step S612.

On the other hand, in step S609, in a case where the heart rate is determined to be below the target zone, the process proceeds to step S611.

In step S611, the guide unit 352 of the mobile terminal 121 correct the target value of the pitch to the upper side such that the heart rate of the target user is raised. Thereafter, the process proceeds to step S612.

On the other hand, in step S608, in a case where the heart rate is determined to be within the target zone, the process of steps S609 to S611 is skipped, and the process proceeds to step S612.

In step S612, the guide unit 352 of the mobile terminal 121 determines whether or not a predetermined time has elapsed. In a case where the predetermined time is determined not to have elapsed, the process is returned to step S607.

Thereafter, in step S612, until the predetermined time is determined to have elapsed, the process of step S607 to S612 is repeatedly executed. Accordingly, for example, like a period of time t2 to time t3 illustrated in FIG. 56, training for maintaining the stride to be approximately constant and causing the heart rate to be stabilized near the target value while adjusting the pitch is performed.

On the other hand, in step S612, in a case where the predetermined time is determined to have elapsed, the process proceeds to step S613. For example, at time t3 illustrated in FIG. 56, the predetermined time is determined to have elapsed, and the process proceeds to step S613.

In step S613, the guide unit 352 of the mobile terminal 121 sets the target value of the pitch to a predetermined value.

In step S614, similarly to the process of step S607, the pitch and the stride are guided toward the target values.

In step S615, similarly to the process of step S608, it is determined whether or not the heart rate is within the target zone. In a case where the heart rate is determined to be out of the target zone, the process proceeds to step S616.

In step S616, similarly to the process of step S609, it is determined whether or not the heart rate is above the target zone. In a case where the heart rate is determined to be above the target zone, the process proceeds to step S617.

In step S617, the guide unit 352 of the mobile terminal 121 corrects the target value of the stride to the lower side such that the heart rate of the target user is lowered. For example, like at time t4 illustrated in FIG. 56, in a case where the heart rate is far above the target value, the target value of the stride is corrected to the lower side. Thereafter, the process proceeds to step S619.

On the other hand, in step S616, in a case where the heart rate is determined to be below the target zone, the process proceeds to step S618.

In step S618, the guide unit 352 of the mobile terminal 121 corrects the target value of the stride to the upper side such that the heart rate of the target user is raised. Thereafter, the process proceeds to step S619.

On the other hand, in step S615, in a case where the heart rate is determined to be within the target zone, the process of steps S616 to S618 is skipped, and the process proceeds to step S619.

In step S619, the guide unit 352 of the mobile terminal 121 determines whether or not a predetermined time has elapsed. In a case where the predetermined time is determined not to have elapsed, the process is returned to step S614.

Thereafter, in step S619, until the predetermined time is determined to have elapsed, the process of steps S614 to S619 is repeatedly executed. In this way, for example, like in a period of time t4 to time t5 illustrated in FIG. 56, training for maintaining the pitch to be approximately constant and stabilizing the heart rate near the target value while the stride is adjusted is performed.

On the other hand, in step S619, in a case where the predetermined time is determined to have elapsed, the process proceeds to step S620.

Meanwhile, in step S620, the guide unit 352 of the mobile terminal 121 determines whether or not the training has been repeated for a target number of times. In a case where it is determined that the training has not been repeated for the target number of times, the process is returned to step S606.

Thereafter, in step S620, until it is determined that the training has been repeated for the target number of times, the process of steps S606 to S620 is repeatedly executed.

On the other hand, in step S620, in a case where it is determined that the training has been repeated for the target number of times, the heart rate maintaining training support process ends.

In this way described above, the target user can perform training for maintaining the heart rate to be constant while alternately raising or lowering the pitch and the stride. Accordingly, the target user can experience various combinations of the pitch and the stride at the same heart rate. Then, the target user, for example, at a certain heart rate, can acquire a combination of the pitch and the stride having highest stamina efficiency.

In addition, during the training or after the training, the timing diagram illustrated in FIG. 56 may be presented to the target user. Furthermore, for example, the transitions of the heart rate, the stride, and the pitch in training performed in the past may be presented together for a comparison.

(Running Support Process)

Next, a running support process executed by the client 112 will be described with reference to a flowchart illustrated in FIG. 57. This process, for example, is started when a user (hereinafter, referred to as a target user in this process) who is a target for the running support inputs an instruction for starting the running support to the mobile terminal 121 or the wearable terminal 122.

In step S701, the guide unit 352 of the mobile terminal 121 requests the server 111 to generate a running plan. At this time, the guide unit 352 transmits information representing a course to run and the like to the server 111. In addition, the guide unit 352, for example, may be configured to transmit information relating to the condition of the target user to the server 111. As the information relating to the condition of the target user, for example, actually-measured values of the heart rate, the body temperature, and the like may be considered.

In addition, the guide unit 352, for example, may be configured to transmit the information relating to the condition set by the target user to the server 111. In such a case, for example, the target user selects his condition class from among "very good", "good", "O.K.", "bad", "very bad" or inputs his condition index using a numerical value of "1" to "100".

In addition, the guide unit 352, for example, may be configured to transmit information relating to a generation mode of a running plan set by the target user. In such a case, for example, the target user selects a desired mode from among three modes of "aggressive", "comfortable", and "safe". The "aggressive" mode is a mode in which the running plan is generated such that the target user runs at a pace faster than that of a normal time and completes running for a time shorter than an average time of the target user. The "comfortable" mode is a mode in which a running plan is generated such that the target user runs at a pace of the normal time and completes running in an average time of the target user.

The "safe" mode is a mode in which a running plan is generated such that the target user runs at a pace slower than that of the normal time and completes running in a time longer than the average time of the target user.

Figure 59:
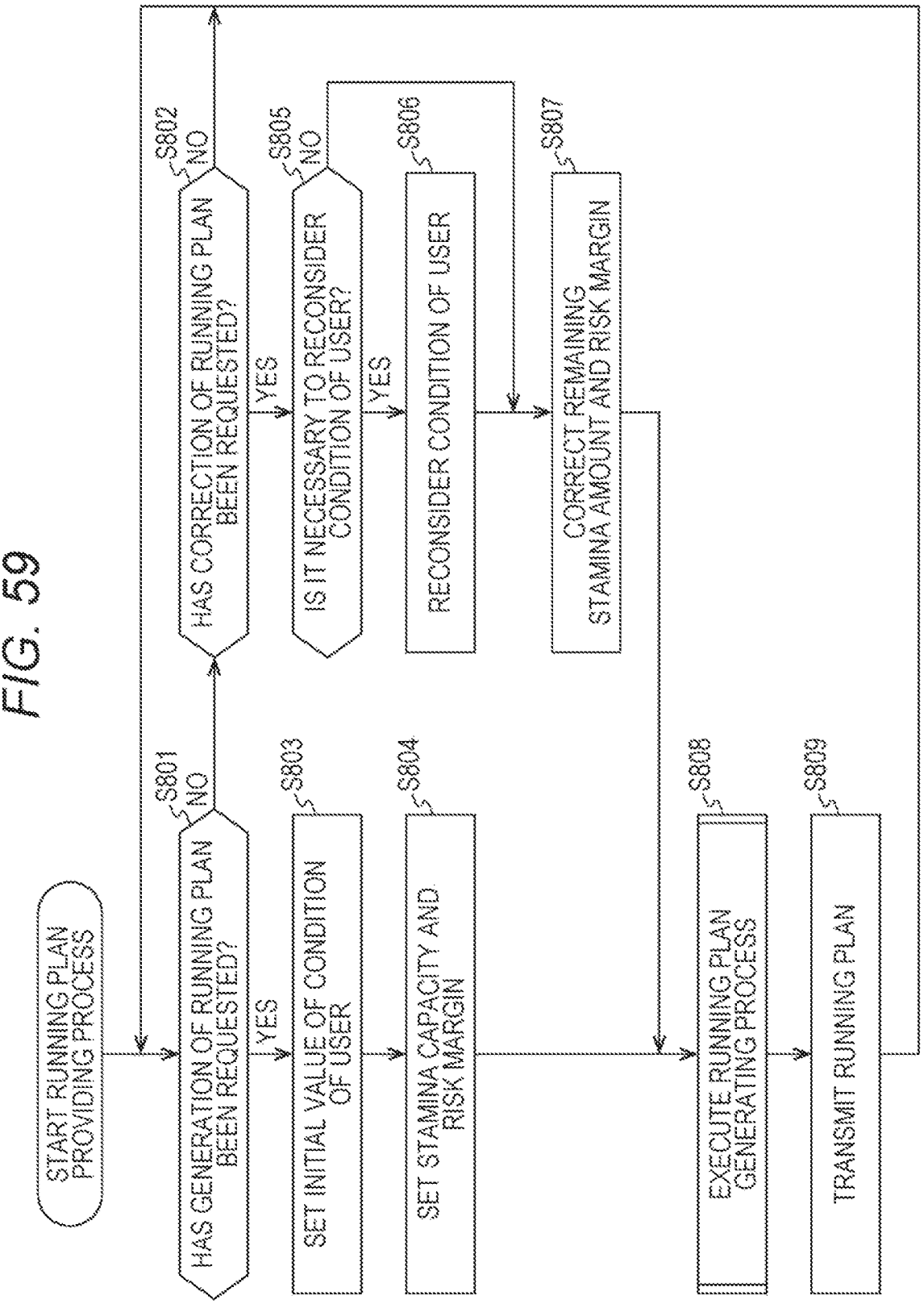
FIG. 59 is a flowchart that illustrates a running plan providing process executed by a server in correspondence with the running support process of the client.

The server 111, in step S808 illustrated in FIG. 59 to be described later, generates a running plan and transmits the running plan in step S809.

The running plan includes at least one of the distribution of the pitch and the stride and the distribution of speeds in a course run by the target user.

Figure 58:
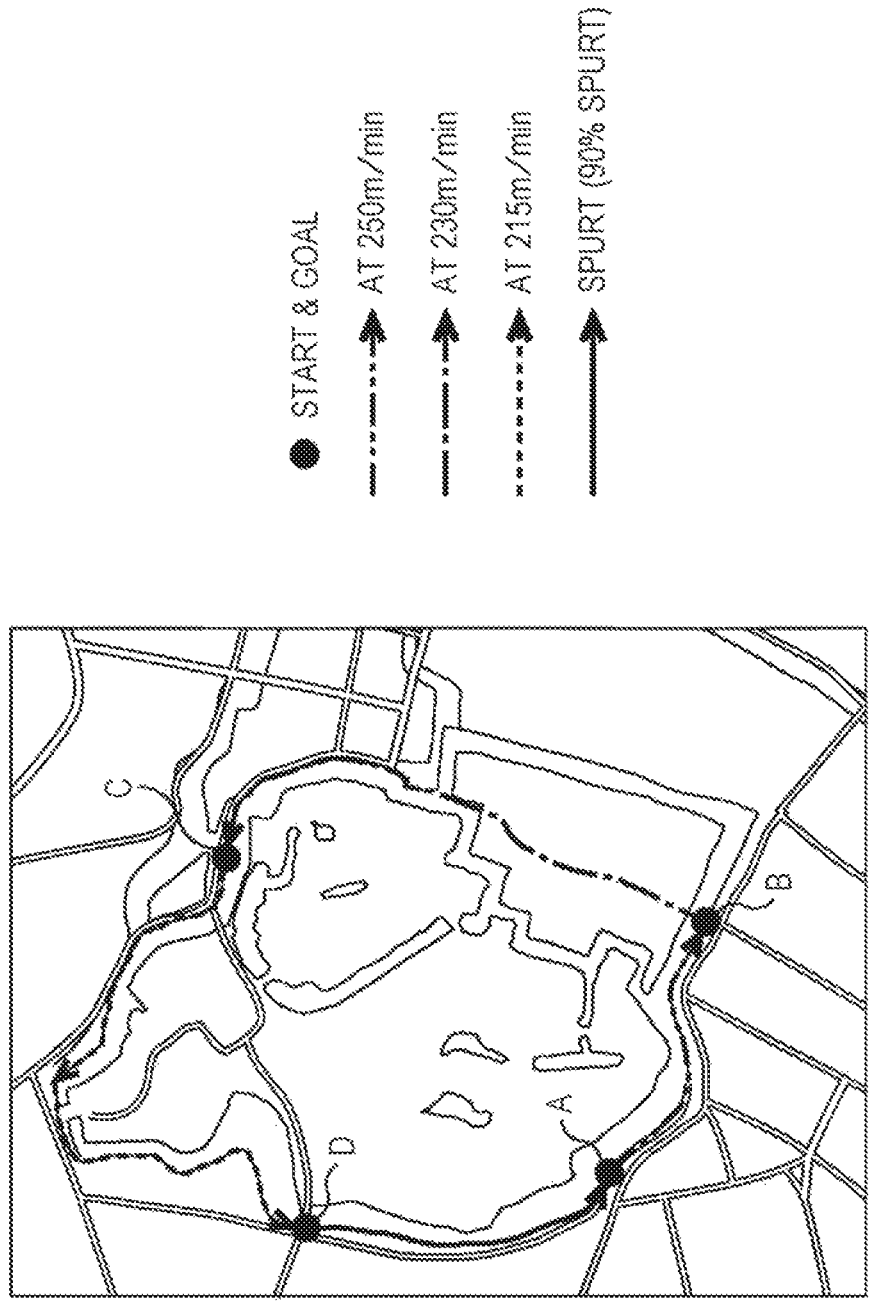
FIG. 58 is a diagram that illustrates an example of a running plan.

FIG. 58 illustrates an example of the running plan. As will be described later, the running plan divides a course into unit sections each having a predetermined length (for example, 1 km), and a running pattern is set to each unit period. The running pattern, for example, includes a combination of a target pitch and a target stride, and a value acquired by multiplying the target pitch by the target stride is a target speed.

For example, in the example illustrated in FIG. 58, the target speed of a section from a position A that is a start position to a position B that is a goal position is set to 250 m/min. The target speed of a section from the position B to a position C is set to 230 m/min. The target speed of a section from the position C to a position D is set to 215 m/min. In a section from the point D to the point A, a spurt with 90% of the power is set.

The running plan, instead of the combination of the target pitch and the target stride of each unit section, may include only a target speed. In addition, the running plan, for example, may be configured to include a target value of the heart rate in each section of the course.

In step S702, the guide unit 352 of the mobile terminal 121 receives the running plan transmitted from the server 111. In addition, at this time, the guide unit 352 may be configured to acquire data of a latest running characteristic, a latest cardiorespiratory capacity, and a latest stamina characteristic of the target user from the server 111.

In step S703, similarly to the process of step S502 illustrated in FIG. 49 described above, measurement is started.

In step S704, the guide unit 352 of the mobile terminal 121 sets parameters of the running plan corresponding to the situation of the current time point as guide parameters. For example, the guide unit 352 sets a target pitch and a target stride at the time of starting the running plan as guide parameters.

In step S705, the client 112 starts guiding. More specifically, the guide unit 352 of the mobile terminal 121 guides the target user to run with the target pitch and the target stride represented in the running plan through the wearable terminal 122 by using the guiding method described above. At this time, the output unit 405 of the wearable terminal 122, for example, outputs a voice message of "A pace corresponding to the stamina will be directed. Please run according to the sound!".

In step S706, the guide unit 352 of the mobile terminal 121 determines whether or not a correction of the running plan is necessary. In a case where the correction of the running plan is determined to be necessary, the process proceeds to step S707.

For example, in a case where a state in which the target user does not run according to the running plan is continued for a predetermined time or more or for a predetermined distance or more, the guide unit 352 determines that the correction of the running plan is necessary. As the state in which the target user does not run according to the running plan, for example, a state may be considered in which at least one of differences between an actual speed, an actual pitch, an actual stride, and an actual heart rate and target values thereof represented in the running plan is a predetermined threshold or more.

In a case where the target user does not run according to the running plan, for example, the output unit 405 of the wearable terminal 122 may warn the target user using a warning sound or the like.

For example, in a case where at least one of the pitch and the stride of the target user is not stable and greatly changes, the guide unit 352 determines that the correction of the running plan is necessary.

In addition, for example, in a case where the condition of the target user is determined to be good, the guide unit 352 determines that a correction of the running plan is necessary. For example, although the target user runs nearly according to the running plan, in a case where the heart rate is lower than an expected value by a predetermined threshold or more or in a case where a state in which the heart rate is lower than an expected value is continued for a predetermined time or more, the guide unit 352 determines that the condition of the target user is good.

Furthermore, for example, in a case where the condition of the target user is determined to be bad, the guide unit 352 determines that a correction of the running plan is necessary. For example, although the target user runs nearly according to the running plan, in a case where the heart rate is higher than an expected value by a predetermined threshold or more or in a case where a state in which the heart rate is higher than an expected value is continued for a predetermined time or more, the guide unit 352 determines that the condition of the target user is bad.

In addition, for example, in a case where the risk of an estimated error is determined to decrease, the guide unit 352 determines that a correction of the running plan is necessary. For example, in a case where the remaining course is a predetermined first distance or less, the guide unit 352 determines that the risk of an estimated error decreases. Alternatively, at a time point at which the remaining course is a second distance, which is longer than the first distance, or less, in a case where the ratio of a distance or a time for which it is difficult to run according to the running plan up to the time point is a predetermined threshold or more, the guide unit 352 determines that the risk of an estimated error decreases.

In step S707, the guide unit 352 of the mobile terminal 121 requests the server 111 to correct the running plan. At this time, the guide unit 352 transmits information representing the reason for requesting the correction of the running plan altogether to the server 111. In addition, the guide unit 352, for example, may be configured to transmit information relating to the condition of the target user to the server 111.

In addition, in a case where a correction of the running plan is determined to be necessary, the guide unit 352 may be configured to suggest the target user to correct the running plan by using a voice message or the like and request the server 111 to correct the running plan when the target user agrees with the correction.

In step S808 illustrated in FIG. 59 to be described later, the server 111 corrects the running plan and transmits the running plan after the correction in step S809.

In step S708, the guide unit 352 of the mobile terminal 121 receives the running plan after the correction transmitted from the server 111. Thereafter, the process proceeds to step S709.

At this time, for example, in a case where the condition of the target user is good, and the running plan is corrected to raise a target time, the output unit 405 of the wearable terminal 122, for example, outputs a voice message of "Today, the condition seems good. Let's aim for a bit more advanced time!".

On the other hand, for example, in a case where the condition of the target user is bad, and the running plan is corrected to lower the target time, the output unit 405, for example, outputs a voice message of "Today, the condition seems bad. Let's slightly lower the pace for running the whole distance!".

In addition, for example, in a case where the remaining course is a predetermined distance or less, and the running plan is corrected due to a decrease in the risk of an estimated error, the output unit 405, for example, outputs a voice message of "Please spurt!. Let's raise the pace and eagerly run!".

For example, in a case where the remaining stamina amount is small, the output unit 405 warns that the remaining stamina amount is small.

On the other hand, in step S706, in a case where a correction of the running plan is determined not to be necessary, the process of steps S707 and S708 is skipped, and the process proceeds to step S709.

In step S709, the guide unit 352 of the mobile terminal 121 updates the guide parameters with parameters of the running plan corresponding to the situation of the current time point. For example, the guide unit 352 updates the guide parameters with the target pitch and the target stride in a currently-running section of the running plan.

In step S710, the guide unit 352 of the mobile terminal 121 determines whether or not the measurement and the guidance are to be ended. In a case where the measurement and the guidance are determined not to be ended, the process is returned to step S706.

Thereafter, in step S710, until the measurement and the guidance are determined to be ended, the process of steps S706 to S710 is repeatedly executed.

In addition, when the target user runs according to the running plan, for example, by using the method described above with reference to FIGS. 32 and 33, the running state and the like of the target user may be presented.

On the other hand, in step S710, in a case where the measurement and the guidance are determined to be ended, the process proceeds to step S711. For example, in a case where the target user runs the whole course or in a case where the target user inputs an instruction for ending the running support to the mobile terminal 121 or the wearable terminal 122, the measurement and the guidance are determined to be ended.

Thereafter, in steps S711 to S713, a process similar to that of steps S306 to S308 illustrated in FIG. 31 is executed, and the running support process ends. In this way, a result of the analysis of the running of this course is presented to the target user by using the method described above with reference to FIGS. 34 to 43.

(Running Plan Providing Process)

Next, a running plan providing process executed by the server 111 in response to the running support process executed by the client 112 illustrated in FIG. 57 will be described with reference to a flowchart illustrated in FIG. 59.

In step S801, the running plan generating unit 252 determines whether or not the generation of a running plan has been requested. In a case where a running plan is determined not to have been requested, the process proceeds to step S802.

In step S802, the running plan generating unit 252 determines whether or not a correction of the running plan has been requested. In a case where a correction of the running plan is determined not to have been requested, the process is returned to step S801.

Thereafter, until the generation of a running plan is determined to have been requested in step S801 or a correction of the running plan is determined to have been requested in step S802, the process of steps S801 and S802 is repeatedly executed.

Figure 57:
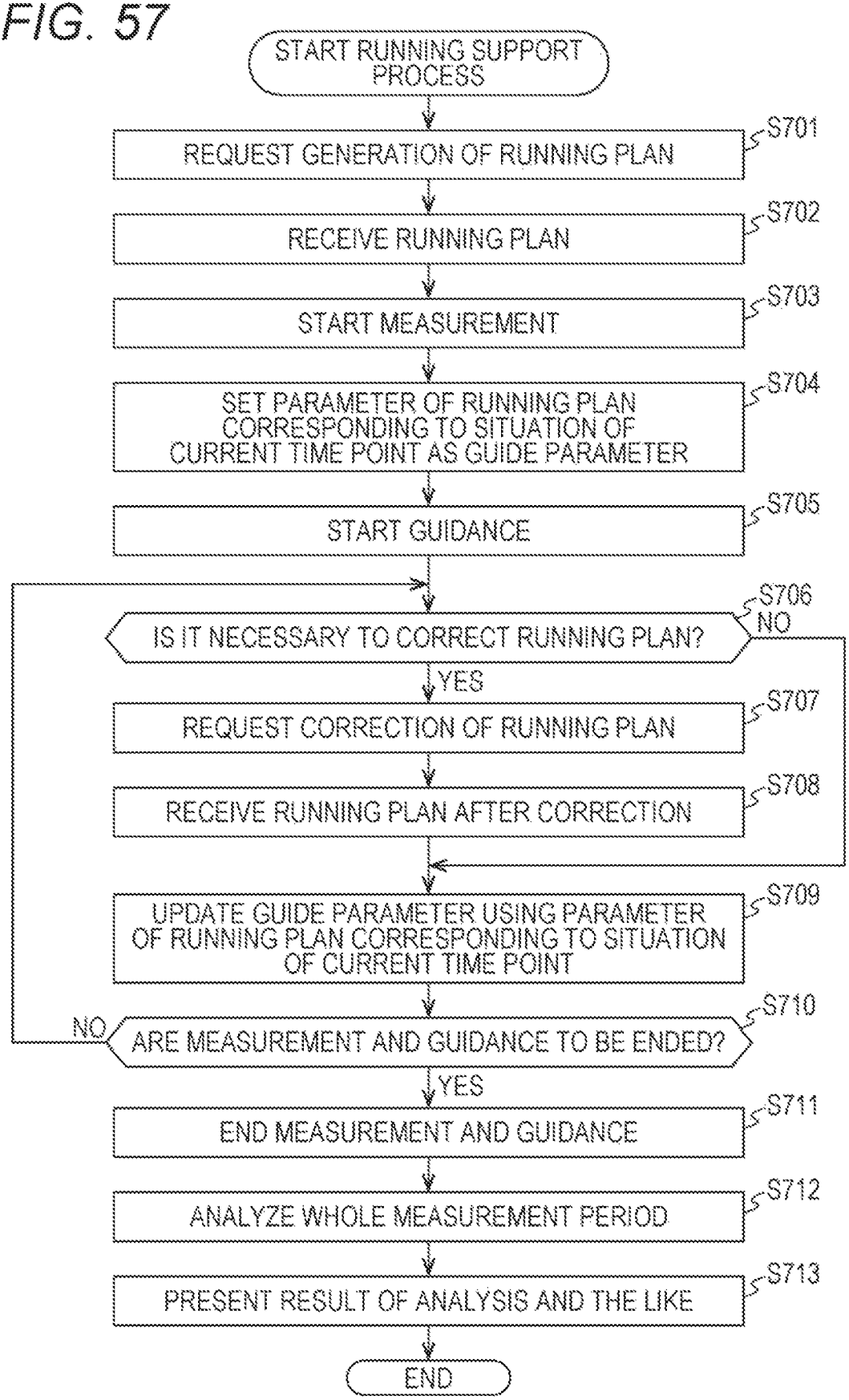
FIG. 57 is a flowchart that illustrates a running support process executed by a client.

On the other hand, in step S801, in a case where a request for the generation of a running plan transmitted from the mobile terminal 121 in step S701 illustrated in FIG. 57 described above has been received, the running plan generating unit 252 determines that the generation of a running plan has been requested, and the process proceeds to step S803.

In step S803, the running plan generating unit 252 sets an initial value of the condition of the user (target user). More specifically, in a case where the information relating to the condition of the target user is acquired from the client 112, the running plan generating unit 252 estimates a condition index or a condition class of the target user based on the information and sets the condition index or the condition class of the target user to the estimated value.

In addition, in a case where the information relating to the condition set by the target user is acquired from the client 112, the running plan generating unit 252 sets the condition index or the condition class of the target user to a set value represented in the acquired information.

Furthermore, in a case where the information relating to the generation mode of the running plan set by the target user is acquired from the client 112, the running plan generating unit 252 sets the condition index or the condition class of the target user based on the information. For example, the running plan generating unit 252 sets the condition index or the condition class to a value better than a standard value in a case where the "aggressive" mode is set, sets the condition index or the condition class to the standard value in a case where the "comfortable" mode is set, and sets the condition index or the condition class to a value worse than the standard value in a case where the "safe" mode is set.

On the other hand, in a case where the information particularly described above is not acquired from the client 112, the running plan generating unit 252 sets the condition index or the condition class of the target user to the standard value.

In step S804, the running plan generating unit 252 sets a stamina capacity and a risk margin. For example, the running plan generating unit 252 calculates a stamina capacity of the target user according to the condition class or the condition index set in the process of step S803 based on the latest stamina characteristic of the target user. In addition, at this time point, since the stamina of the target user has not been consumed, the remaining stamina amount of the target user is equal to the stamina capacity.

In addition, the running plan generating unit 252 sets the risk margin based on the condition index or the condition class set in the process of step S803.

For example, in a case where the running plan is generated such that target user consumes all the stamina capacity, a risk of depleting the stamina of the target user in the middle of the course due to the estimated error or an event on the race development that is not considered is assumed. Thus, in order to avoid the risk, the running plan generating unit 252 generates a running plan with a margin being added thereto so as to allow the stamina to remain at the time of running the whole course. The margin of the stamina, in other words, the remaining of the stamina amount at the time of target user's arriving at the goal is the risk margin.

In a case where the risk margin is set to be large, while the possibility that the stamina of the target user is depleted so as to cause the target user not to run the whole course decreases, the necessary time is increased. On the other hand, in a case where the risk margin is set to be small, while the possibility that the stamina of the target user is depleted so as to cause the target user not to run the whole course increases, the necessary time is decreased.

Thus, for example, in a case where the condition class or the condition index is set to a value better than the standard value, the running plan generating unit 252 sets the risk margin to be smaller than a standard value. In a case where the condition class or the condition index is set to the standard value, the running plan generating unit 252 sets the risk margin to the standard value. In a case where the condition class or the condition index is set to a value worse than the standard value, the running plan generating unit 252 sets the risk margin to be larger than the standard value.

Thereafter, the process proceeds to step S808.

On the other hand, in step S802, in a case where a request for a correction of the running plan transmitted from the mobile terminal 121 in step S707 illustrated in FIG. 57 described above has been received, the running plan generating unit 252 determines that a correction of the running plan is determined to have been requested, and the process proceeds to step S805.

In step S805, the running plan generating unit 252 determines whether or not a review of the condition of the user (target user) is necessary. In a case where the reason for the correction of the running plan is no running of the target user according to the running plan, in a case where the condition of the target user is good, or in a case where the condition of the target user is bad, the running plan generating unit 252 determines that a review of the condition is necessary, and the process proceeds to step S806.

In step S806, the running plan generating unit 252 reviews the condition of the user (target user). For example, the running plan generating unit 252 resets the condition index or the condition class of the target user based on the transitions of the pitch, the stride, and the heart rate of the target user until now.

Thereafter, the process proceeds to step S807.

On the other hand, in step S805, in a case where the reason for the correction of the running plan is a decrease in the risk of the estimated error, the running plan generating unit 252 determines that a review of the condition is not necessary, the process of step S806 is skipped, and the process proceeds to step S807.

For example, in a case where the target user intentionally performs running different from the running plan for chasing another runner or applying tactics, a review of the condition may be determined not to be necessary.

In step S807, the running plan generating unit 252 corrects the remaining stamina amount and the risk margin. More specifically, in the process of step S805, in a case where the condition index or the condition class is reset, the running plan generating unit 252 resets the stamina capacity and the risk margin based on the condition index or the condition class that has been reset.

In a case where the reason for correcting the running plan is a decrease in the risk of the estimated error, the running plan generating unit 252 adjusts the risk margin to a value less than the current value. In other words, according to a decrease in the risk of the estimated error, the risk of depleting the stamina of the target user decreases. Thus, the running plan generating unit 252 decreases the risk margin such that the target user can consume the stamina up to a value close to the limit.

In addition, the running plan generating unit 252 corrects the remaining stamina amount regardless of presence/absence of the resetting of the condition index or the condition class. More specifically, the running plan generating unit 252 estimates the transitions of the stamina efficiency and the remaining stamina amount until now based on the transitions of the pitch and the stride until now, the condition index or the condition class, the stamina capacity of the target user, and the stamina efficiency characteristic. Accordingly, the remaining stamina amount at the current time point is corrected.

Thereafter, the process proceeds to step S808.

Figure 60:
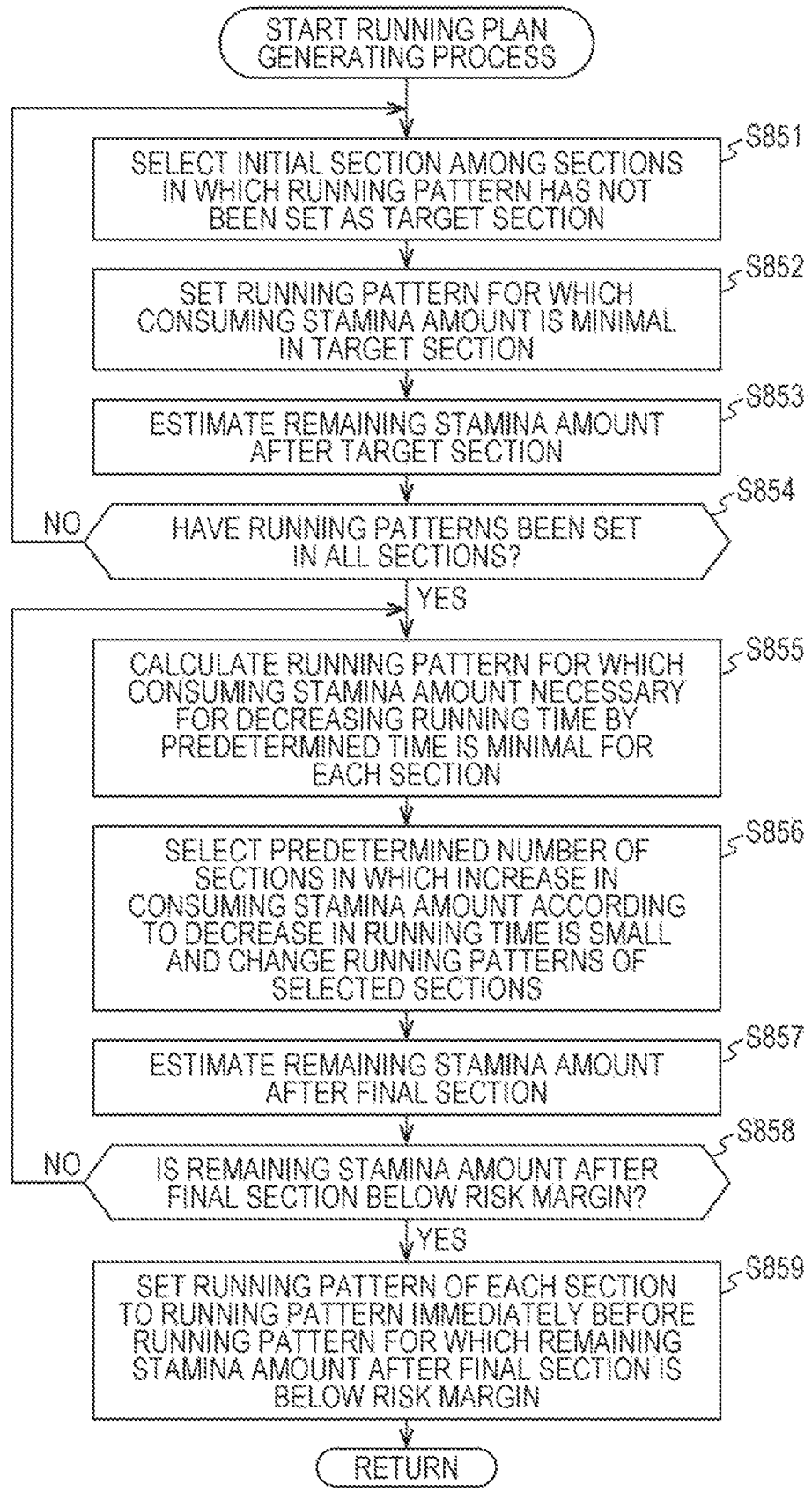
FIG. 60 is a flowchart that illustrates a running plan generating process in detail.

In step S808, the running plan generating unit 252 executes a running plan generating process. Here, the running plan generating process will be described in detail with reference to a flowchart illustrated in FIG. 60.

In step S851, the running plan generating unit 252 selects a first section from among sections in which the running pattern has not been set as a target section.

Here, when a running plan is generated, the whole section of the course is a target for setting a running pattern. Thus, unit sections from the first unit section of the course to the final unit section are sequentially selected as the target section.

On the other hand, when the running plan is corrected, a section (the remaining course) after a position run by the target user until now is a target for setting a running pattern. Thus, unit sections from the first unit section of the remaining course to the final unit section are sequentially selected as the target section.

In step S852, the running plan generating unit 252 sets a running pattern for which the consumed stamina amount is minimal in the target section. More specifically, the running plan generating unit 252 acquires a pitch and a stride for which the stamina efficiency is highest in the estimated value of the current remaining stamina amount based on the stamina efficiency characteristic of the target user. Then, the running plan generating unit 252 sets the pitch and the stride that have been acquired as the running pattern of the target section.

In step S853, the running plan generating unit 252 estimates the remaining stamina amount after the target section. More specifically, the running plan generating unit 252 calculates a consumed stamina amount in the target section by using the following Equation (3).

$$\text{Consumed Stamina Amount} = \text{Distance of Target Section} / \text{Stamina Efficiency} \quad (3)$$

Then, the running plan generating unit 252 estimates the remaining stamina amount after running the target section by subtracting the consumed stamina amount from the estimated value of the current remaining stamina amount.

In step S854, the running plan generating unit 252 determines whether or not the running patterns of all the sections have been set. In a case where it is determined that the running patterns of all the sections have not been set, the process is returned to step S851.

Thereafter, in step S854, until it is determined that the running patterns of all the sections have been set, the process of steps S851 to S854 is repeatedly executed. In this way, when a running plan is generated, the running patterns of all the sections of the course are set. On the other hand, when the running plan is corrected, the running patterns of the remaining sections of the course are set.

On the other hand, in step S854, in a case where it is determined that the running patterns of all the sections have been set, the process proceeds to step S855.

In step S855, the running plan generating unit 252 calculates a running pattern for which a consumed stamina amount that is necessary for shortening the running time by a predetermined time is minimal for each section. More specifically, the running plan generating unit 252, for each unit section, extracts candidates of the running pattern (a combination of a pitch and a stride) that can shorten the running time of the running pattern that is currently set by a unit time (for example, one second). Then, the running plan generating unit 252, for each unit section, calculates a consumed stamina amount for each of the extracted candidates for the running pattern. Then, the running plan generating unit 252, for each unit section, selects a running pattern for which the consumed stamina amount is minimal among the candidates for the running pattern. In addition, the running plan generating unit 252, for each unit section, calculates a difference between the consumed stamina amount of the selected running pattern and the consumed stamina amount of the running pattern that is currently set as a consumed stamina increase amount.

In step S856, the running plan generating unit 252 selects a predetermined number of sections, in which an increase in the consumed stamina amount according to the shortening of the running time is small, and changes the running patterns of the selected sections. More specifically, the running plan generating unit 252 aligns the unit sections in descending order of the consumed stamina increase amount calculated in step S855 and selects the predetermined number of unit sections from a higher rank. Then, the running plan generating unit 252 changes the running patterns of the selected unit sections to the running patterns acquired in the process of step S855.

The number of unit sections of which the running patterns are changed may be set to an arbitrary number that is one or more.

In step S857, the running plan generating unit 252 estimates a remaining stamina amount after the final section. In other words, the running plan generating unit 252, based on the running patterns after the change, similarly to the process of step S853, recalculates a remaining stamina amount after running each unit section in order from the first unit section. In this way, finally, the remaining stamina amount after running the final section is estimated.

In step S858, the running plan generating unit 252 determines whether or not the remaining stamina amount after the final section is below the risk margin. In a case where the remaining stamina amount after the final section is determined not to be below the risk margin, the process is returned to step S855.

Thereafter, in step S858, until the remaining stamina amount after the final section is determined to be below the risk margin, the process of steps S855 to S858 is repeatedly executed. In this way, the running pattern of each unit section is updated such that the running time is shortened while an increase in the consumed stamina amount is suppressed to be small.

On the other hand, in step S858, in a case where the remaining stamina amount after the final section is determined to be below the risk margin, the process proceeds to step S859.

In step S859, the running plan generating unit 252 sets the running pattern of each section to a running pattern that is right before the running pattern for which the remaining stamina amount after the final section is below the risk margin, and the running plan generating process ends.

In this way, a running plan capable of running the course for a shortest running time in the current condition of the target user or a time close thereto is generated while the depletion of the stamina during the course is avoided.

In addition, for example, in a case where the target user performs rehearsal running of the course in advance, by referring to the measurement data at that time, a running plan is generated, whereby a more appropriate running plan can be provided.

Referring back to FIG. 59, in step S809, the running plan generating unit 252 transmits the running plan to the mobile terminal 121 of the target user.

Thereafter, the process is returned to step S801, and the process of step S801 and subsequent steps are executed.

In this way, the target user runs according to the running plan, whereby efficient running that is appropriate for his ability and condition can be performed. Accordingly, a necessary time can be shortened, and running the whole course can be performed also in a case where the condition is bad. In addition, by reviewing the risk margin, the pace can be raised or a spurt can be applied in the latter half.

In addition, the target user can perform training for repeatedly running the same course in the same running pattern.

Furthermore, even in a case where the target user is not accustomed to long-distance running and does not know a pace distribution, he can run with an appropriate pace distribution.

In addition, since the running plan is corrected in real time, for example, also in a case where the target user does not follow the running plan but applies tactics for another runner, a running plan in consideration of the stamina amount consumed according to the tactics can be newly presented.

4. Modified Example

Hereinafter, modified examples of an embodiment of the present technology described above will be described.
{Modified Example Relating to System Configuration and Sharing Process}

The configuration of the system and the sharing of the process among apparatuses described above can be freely changed as is necessary.

For example, a part or all of the process executed by the server 111 described above can be executed by the client 112. For example, the client 112 can be configured to independently analyze the running characteristic, the cardiorespiratory capacity, and the stamina characteristic based on user's measurement data or generate a running plan.

In addition, for example, a part of the process executed by the client 112 described above may be configured to be executed by the server 111. For example, it may be configured such that the measurement data is transmitted from the client 112 to the server 111, and the server 111 analyzes the user's running state (for example, balance of the pitch and the stride and the like). In addition, it may be configured such that the server 111 controls presentation of data executed by the client 112 by generating data (for example, image data, audio data, or the like) to be presented to the user by the client 112 and transmitting the data to the client 112.

Furthermore, for example, the sharing of the process between the mobile terminal 121 and the wearable terminal 122 can be arbitrarily changed. For example, by integrating the function of the mobile terminal 121 into the wearable terminal 122, the wearable terminal 122 may be configured to execute all the processes of the mobile terminal 121. In addition, as is necessary, the process may be shared by arranging two or more mobile terminals 121 or two or more wearable terminals 122 in one client 112.

In addition, for example, the wearable terminal 122 may be configured to display the screens described above. Furthermore, for example, it may be configured such that image data is supplied from the client 112 to an external apparatus, and the external apparatus displays the screens described above. In addition, for example, it may be configured such that a voice message is output from the mobile terminal 121, and the user hears the voice message output from the mobile terminal 121 by using an earphone or the like.

Here, the kinds of the sensors of the measurement unit 406 of the wearable terminal 122 illustrated in FIG. 12 are examples, and, as is necessary, the kinds and the number of the sensors can be changed. In addition, some of the sensors may be arranged in the mobile terminal 121.

In addition, the mobile terminal 121 and the wearable terminal 122 may be configured to communicate with each other in a wired manner.

Furthermore, for example, in a case where a communication area between the mobile terminal 121 and the wearable terminal 122 is large, and the user runs inside the communication area, it is not necessary for the user to carry the mobile terminal 121 during the running. In such a case, for example, instead of the mobile terminal 121, a personal computer or the like can be used.

{Modified Example Relating to Running Plan}

For example, the user may set a target time. Then, for example, in the running plan generating process illustrated in FIG. 60, the running plan generating unit 252 may be configured to repeat the process of steps S855 to S858 until it is the target time.

Many users are considered to have a tendency of running according to the guide as possibly as can regardless of the good condition/bad condition. As a result, there is concern that it may take time to perceive the user's actual condition. Thus, for example, the running plan generating unit 252 may be configured not to perform guiding at first and allow the user to freely run, estimate the user's condition based on the running state, the heart rate, and the like during that period, and generate a running plan. Accordingly, a running plan according to the user's condition can be generated more appropriately.

In addition, the running plan may be generated by dividing the course not into unit sections having the same distance but sections having mutually-different distances.

Furthermore, the running plan generating unit 252 may generate a running plan in consideration of the characteristics of the course.

For example, the running plan generating unit 252, for a course run by the target user, analyses running data of other users accumulated in the past, thereby detecting singular sections of the course. Here, a singular section, for example, is a section in which the user's running state is quite different from those in the other sections such as an upward slope or a downward slope. Then, the stamina characteristic analyzing unit 263 analyzes the transition of the consumed stamina amount based on the running data of the course of a user similar to the target user. Then, the stamina characteristic analyzing unit 263 corrects the stamina efficiency characteristic of the target user based on a result of the analysis, and the running plan generating unit 252 generates a running plan based on the corrected stamina efficiency characteristic.

For example, the stamina characteristic analyzing unit 263 acquires information relating to the characteristics of an upward slope and a downward slope of the course based on map information of the course. Then, the stamina characteristic analyzing unit 263 corrects the running load based on the characteristics of the upward slop and the downward slope of the course and corrects the user's stamina efficiency characteristic in the section of the upward slope and the section of the downward slope. Then, the running plan generating unit 252 generates a running plan based on the corrected stamina efficiency characteristic.

In addition, for example, the running plan generating unit 252 may generate a running plan in consideration of the weather, the temperature, the humidity, the altitude, and the like. For example, together with the running data (the speed, the pitch, the stride, the heart rate, and the like) of many users, measurement data of parameters of the weather, the temperature, the humidity, the altitude, and the like are accumulated, and the stamina characteristic analyzing unit 263 learns relations between such parameters and the stamina efficiency characteristic through machine learning. A technique of the machine learning is not particularly limited but, for example, a neural network, Support Vector Machine (SVM), or the like can be used. Then, the stamina characteristic analyzing unit 263 corrects the stamina efficiency characteristic of each user based on each parameter by using a result of the machine learning, and the running plan generating unit 252 generates a running plan based on the corrected stamina efficiency characteristic.

In addition, for example, the running plan generating unit 252 may generate a running plan in consideration of a wind speed and a wind direction. For example, wind speeds and wind directions may be detected by using sensors disposed in the wearable terminal 122 or sensors installed to several locations of a course, and the running plan generating unit 252 may appropriately update the running plan in consideration of the influences of the wind speed and the wind direction.

When the wind becomes strong, the user's running state is expected to be separated from the running characteristic due to the influence thereof. Particularly, such as phenomenon is expected to be prominent for a user whose running is stable. Thus, for example, the running plan generating unit 252 may be configured to correct the running plan based on the running characteristic and the degree of separation from the running state. At that time, by correcting the running plan with the remaining stamina amount after the final section set to be large, the risk of not running the whole course can be decreased.

[Modified Example of Guiding Method]

In the description presented above, while an example in which the pitch is guided by using a phase difference between the guiding sound and the landing timing has been illustrated, a specific process of this example will be described with reference to FIGS. 61 to 63.

First, a case will be described with reference to FIG. 61 in which the pitch is guided by using only the tempo of the guiding sound without using a phase difference between the guiding sound and the landing timing. An upper side of FIG. 61 illustrates a relation among a natural rhythm, a rhythm after guiding, and a guide stimulus of a case where a user is drawn by a guide stimulus (guiding sound) in a short time, in other words, in a case where the user follows the guiding sound in a short time and changes the pitch. A lower side of FIG. 61 illustrates a relation among a natural rhythm, a rhythm after guiding, and a guide stimulus of a case where a user is not drawn in a short time by a guide stimulus (guiding sound), in other words, in a case where the user does not immediately follow the guiding sound and does not change the pitch.

Here, the natural rhythm, for example, is the rhythm of user's steps before guiding, and each circle of a dotted line in the drawing represents the landing timing of user's legs. The rhythm after guiding, for example, is the rhythm of user's steps after guiding, and each circle of a solid line in the drawing represents the landing timing of user's legs. Each black circle disposed in the row of the guide stimulus in the drawing, for example, represents the output timing of the guiding sound.

Figure 61:
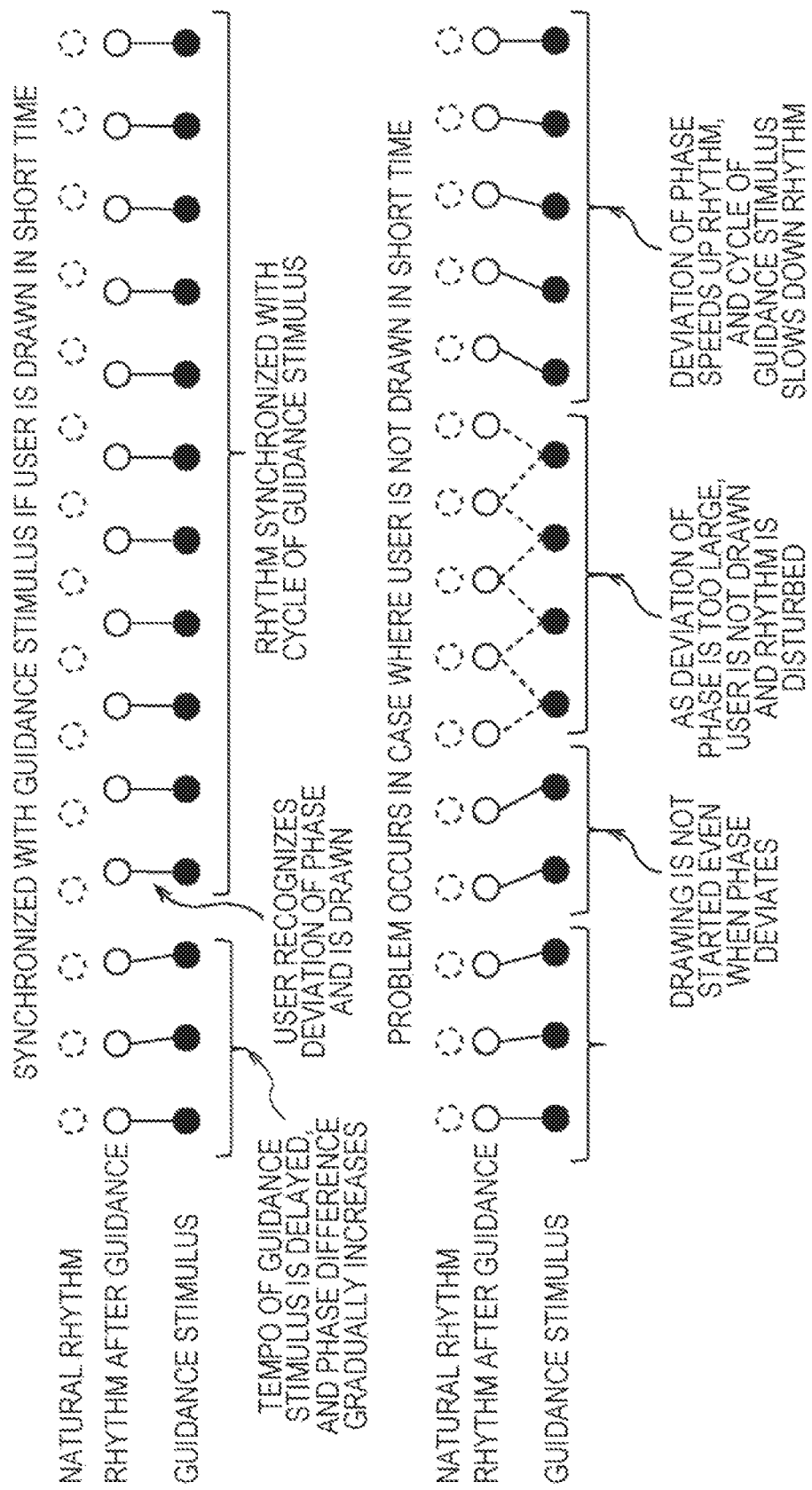
FIG. 61 is a diagram that illustrates a case where a pitch is guided by using only a tempo of a guidance sound.

For example, as illustrated in the upper drawing of FIG. 61, in a case where the user's pitch is guided to be delayed, the cycle of the guiding sound is fixed to a cycle longer than that of the natural rhythm, and the tempo of the guiding sound is delayed. In this way, a phase difference between the user's landing timing and the output timing of the guiding sound gradually increases. Then, after recognizing a phase deviation between the guiding sound and the landing timing, the user synchronizes the cycle (the rhythm of steps) of steps with the cycle of guiding sounds, thereby arriving at a target pitch.

On the other hand, as illustrated in the lower drawing of FIG. 61, in a case where the user does not immediately follow the guiding sound and does not change the pitch, a phase difference between the guiding sound and the landing timing gradually increases. Then, when a phase deviation between the guiding sound and the landing timing becomes too large, there is concern that the rhythm of steps of the user is rather disturbed by the guiding sound.

For example, when the phase deviation between the guiding sound and the landing timing becomes too large, there is a case where the guiding sound is output immediately before the landing timing. In such a case, although the rhythm of steps is guided to be delayed (the pitch is delayed) by using the guiding sound, there is concern that the user misapprehends that the rhythm of steps is guided to be quickened (the pitch is quickened). According to a deviation between the guiding direction according to the guiding sound and user's recognition, there is concern that the user disturbs the rhythm.

In contrast to this, by guiding the pitch by using a phase difference between the guiding sound and the landing tim-ing, also in a case where the user does not immediately follow the guiding sound, the user can be appropriately guided.

Here, a guide stimulus setting process executed in a case where the pitch is guided by using a phase difference between the guiding sound and the landing timing will be described with reference to a flowchart illustrated in FIG. 62.

In step S901, the guide unit 352 of the mobile terminal 121 sets a target tempo interval to a variable Tt. In this example, the target tempo interval is a target value of the cycle (a time that is necessary for one step) of user's steps. Hereinafter, the variable Tt may be also referred to as a target step cycle Tt.

In step S902, the guide unit 352 sets a rhythm time measurement result to a variable Tr. In this example, the rhythm time is user's latest landing time. Hereinafter, the variable Tr will be also referred to as latest landing time Tr.

In step S903, the guide unit 352 sets the latest landing time Tr to a variable T0. The variable T0 is a variable that represents rhythm time of the previous time and, in this example, represents the landing time of the previous time. Hereinafter, the variable T0 will be also referred to as previous landing time T0.

In step S904, similarly to the process of step S902, a result of the measurement of the rhythm time is set to the variable Tr. Accordingly, the next landing time after the landing time measured in step S902 is set to the latest landing time Tr.

In step S905, the guide unit 352 sets the latest landing time Tr to a variable TlastStim. Here, the variable TlastStim is a variable that represents time when the previous guide stimulus is issued and, in this example, represents time when the previous guiding sound is output. Hereinafter, the variable TlastStim is also referred to as previous guiding sound output time TlastStim. However, at a time point when the process of step S905 is executed, since it is before the output of the guiding sound, the latest landing time Tr is set to the previous guiding sound output time TlastStim.

In step S906, the guide unit 352 sets a value acquired by subtracting the previous landing time T0 from the latest landing time Tr to a variable Ti. The variable Ti is a variable that represents the previous rhythm cycle that has been measured and, in this example, represents a measured value of the previous cycle of steps. Hereinafter, the variable Ti will be also referred to as a measured step cycle Ti.

In step S907, the guide unit 352 sets a sum of the previous guiding sound output time TlastStim and the target step cycle Tt to the guiding sound output time Tstim. Here, the variable Tstim is a variable representing time when a guide stimulus is issued and, in this example, represents time when the guiding sound is output. Hereinafter, the variable Tstim will be also referred to as guiding sound output time Tstim. According to this process, the guiding sound output time Tstim is set to a time when the target step cycle Tt elapses from time (the previous guiding sound output time TlastStim) when the previous guiding sound is output.

In step S908, the guide unit 352 compares $Tr+Ti \times (1-c0)$ and Tstim with each other, and a larger value thereof is set to the guiding sound output time Tstim. Here, c0 is a constant representing a predetermined ratio and is set to a positive value that is sufficiently smaller than "1". Thus, $Tr+Ti \times (1-c0)$ is time that is the measurement step cycle $Ti \times c0$ before time when the measurement step cycle Ti elapses from the latest landing time Tr.

In step S909, the guide unit 352 compares $Tr+Ti \times (1+c1)$ and Tstim with each other and sets a larger value thereof to the guiding sound output time Tstim. Here, c1 is a constant representing a predetermined ratio and is set to a positive value that is sufficiently smaller than "1". Thus, $Tr+Ti\times(1+c1)$ is time that is the measurement step cycle $Ti\times c1$ after the time when the measurement step cycle Ti elapses from the latest landing time Tr.

In this process of steps S908 and S909, in a case where the guiding sound output time Tstim satisfies the following Equation (4), the guiding sound output time Tstim is not corrected.

$$Tr+Ti\times(1-c0) \leq Tstim \leq Tr+Ti\times(1+c1) \quad (4)$$

On the other hand, in a case where the guiding sound output time Tstim is before $Tr+Ti\times(1-c0)$, it is corrected to $Tr+Ti\times(1-c0)$. In addition, in a case where the guiding sound output time Tstim is after $Tr+Ti\times(1+c1)$, it is corrected to $Tr+Ti\times(1+c1)$. In this way, a phase difference between the next landing timing that is estimated based on the previous two landing timings and the output timing of the guiding sound is limited to be within a predetermined range.

In step S910, the guide unit 352 sets guide stimulus issuance time. In other words, the guide unit 352 sets the output time of the next guiding sound to the guiding sound output time Tstim. Then, when it is the guiding sound output time Tstim, the guiding sound is output.

In step S911, the guide unit 352 sets the guiding sound output time Tstim to the previous guiding sound output time TlastStim.

In step S912, the guide unit 352 sets the latest landing time Tr to the previous landing time TO.

In step S913, similarly to the process of steps S902 and S904, a result of the measurement of the rhythm time is set to the variable Tr.

In step S914, the guide unit 352 determines whether or not the guiding is to be ended. In a case where the guiding is determined not to be ended, the process is returned to step S906. Thereafter, in step S914, until the guiding is determined to be ended, the process of steps S906 to S914 is repeatedly executed.

On the other hand, in step S914, in a case where the guiding is determined to be ended, the guide stimulus setting process ends.

Figure 63:
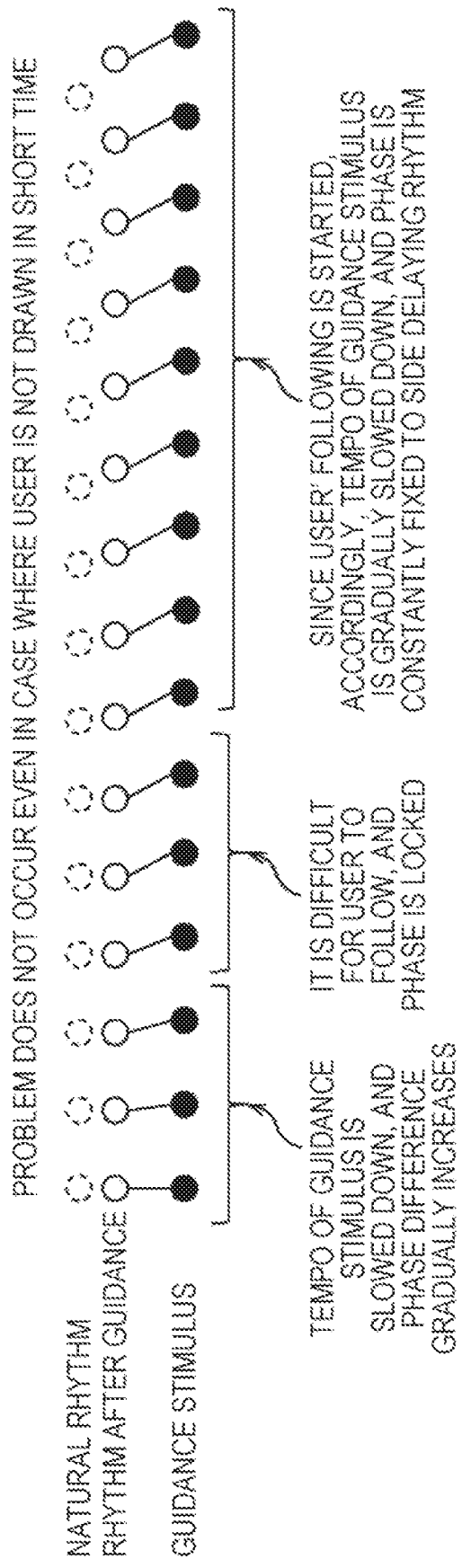
FIG. 63 is a diagram that illustrates a case where a pitch is guided by using a phase difference between a guide sound and landing timing.

Accordingly, as illustrated in FIG. 63, even when the user is not immediately drawn by the guide stimulus (guiding sound), no problem occurs. In other words, even when the user does not immediately follow the guiding sound and does not change the pitch, the phase of the guiding sound with respect to the landing time is locked such that a phase difference between the guiding sound and the landing timing is within a predetermined range. In addition, when the user starts to follow the guiding sound, the tempo of the guiding sound is controlled in accordance therewith. In this way, the occurrence of a deviation between the guiding direction according to the guiding sound and user's recognition is prevented, and the user's pitch is appropriately guided.

{Modified Example of Analyzing Process}

Figure 64:
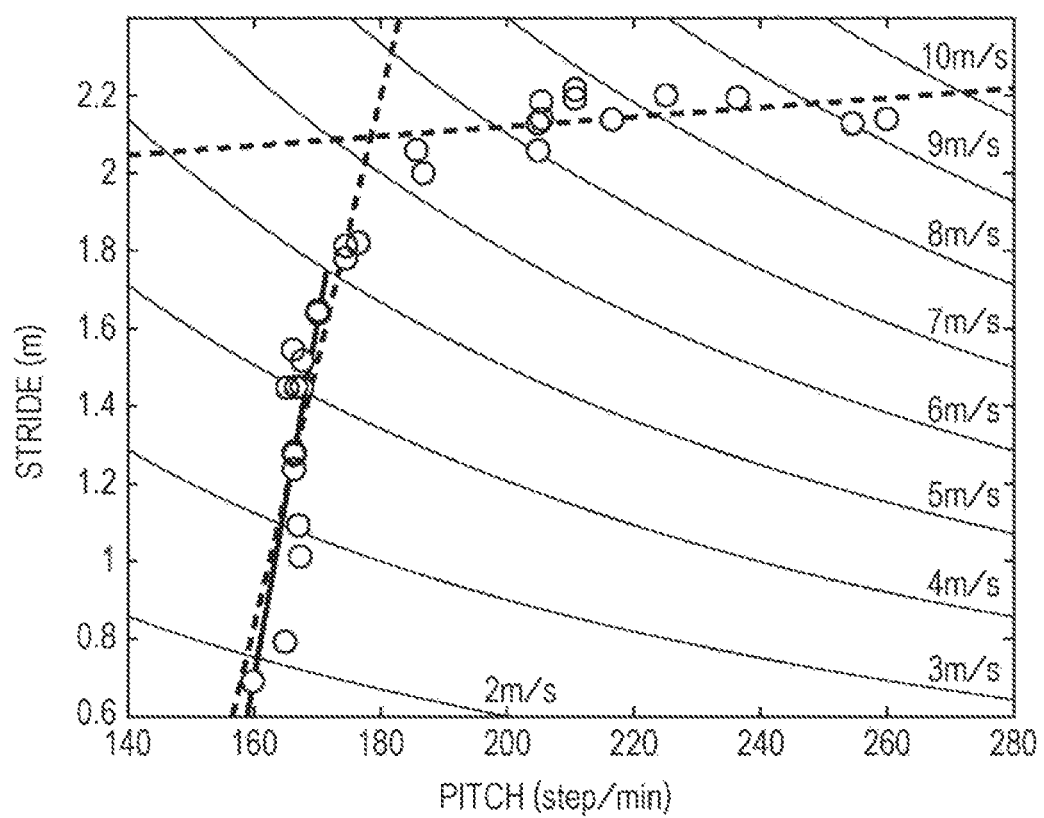
FIG. 64 is a graph that illustrates an example of a pitch-stride characteristic.
Figure 65:
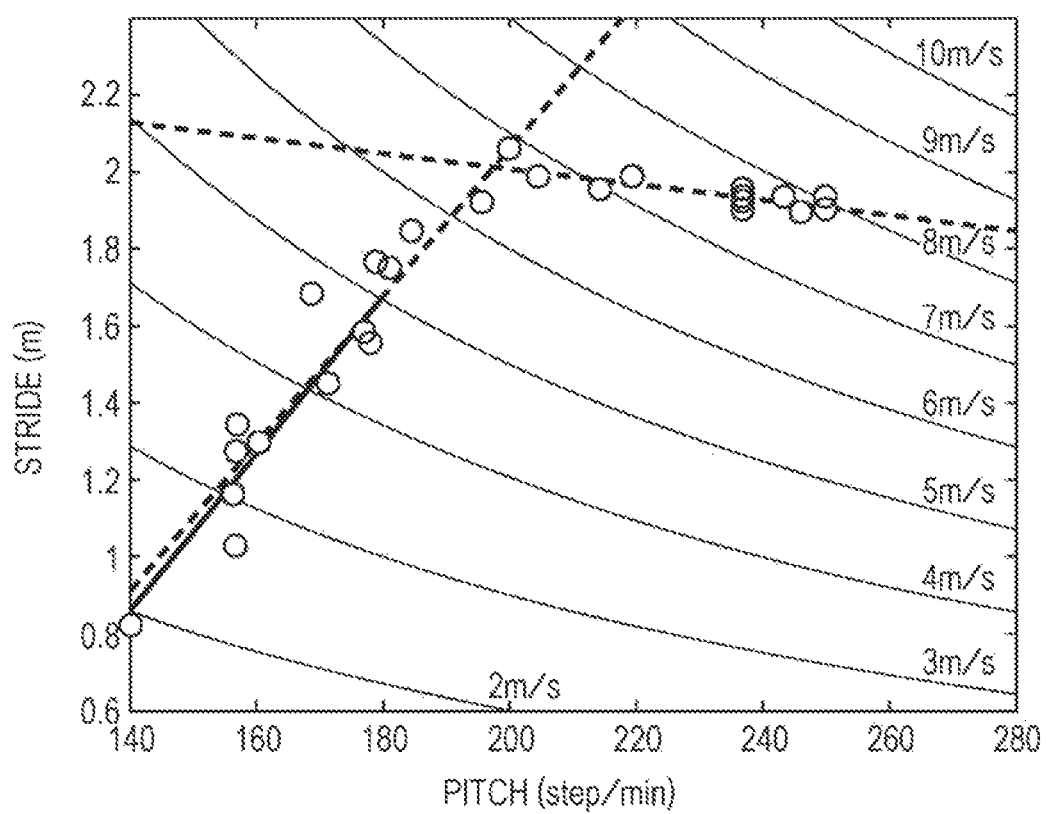
FIG. 65 is a graph that illustrates an example of a pitch-stride characteristic.

FIGS. 64 and 65 are graphs that illustrate examples of the pitch-stride characteristics of two mutually-different users. The horizontal axis represents the pitch, the left vertical axis represents the stride, and the right vertical axis represents the speed. In each drawing, two dotted straight lines represent pitch-stride characteristics acquired by polygonal line approximation using all the measurement results. On the other hand, in each drawing, a solid straight line represents a pitch-stride characteristic of a middle/low speed region acquired by linear approximation using only measurement results for a middle/low speed region of 5 m/s or less.

As illustrated in these examples, for most of users, the pitch-stride characteristic of the middle/low speed region can be analyzed with accuracy that is almost the same as that of a case where measurement results of a high-speed region are used, without using measurement results of the high-speed region.

Meanwhile, for example, there are many users running only in a middle/low speed region (for example, less than 5 m/s) such as a general citizen runner or a novice running a long distance. For such users, a running characteristic of a high-speed region is not necessarily needed, and it is sufficient to analyze the running characteristic of the middle/low speed region.

Thus, for example, it may be configured such that the measurement process at the time of high-speed running of step S3 illustrated in FIG. 16 described above is omitted, and the running characteristic of a target user is analyzed based only on measurement results of the speed, the pitch, and the stride at the time of low-speed running and at the time of standard-speed running. In such a case, the process of detecting the pitch switching speed and the stride switching speed and the process of setting the stride/pitch switching speed may also be omitted. In addition, based on the running characteristic of the middle/low speed region, the other services may be provided for the target user.

In addition, for users who are not particularly accustomed to running, there is a high possibility that high-speed running causes damage or an accident. For this reason, by omitting the measurement at the time of high-speed running, an effect of analyzing the running characteristic more safely is acquired.

In a case where the running characteristic is analyzed based only on measurement results at the time of low-speed running and at the time of standard-speed running, in order to maintain the analysis accuracy to be high, it is necessary to suppress the speed at the time of standard-speed running to be less than the stride/pitch switching speed. For this reason, for example, a target user may be guided such that the speed at the time of standard-speed running is a predetermined limit speed or less. This limit speed, for example, may be considered to be set in the same way to a speed (for example, 4 m/s) that is assumed to be assuredly slower than the stride/pitch switching speed for a general user. Alternatively, for example, it may be configured such that users are classified into clusters using the method described above or the like, and a limit speed is set for each cluster.

Here, the stride is a parameter having a high correlation with the height, and, for example, an ideal range of strides is different for each height. Thus, for example, in the various processes described above, it may be considered to use "stride/height" that is acquired by normalizing the stride using the height as a parameter instead of the stride. In such a case, an adverse effect such as an error according to a height difference between users or the like is suppressed, and various analyzing processes, setting of a target value and a training menu, and the like can be more appropriately performed. For example, by using the stride/height, the accuracy of the analysis of the running characteristic is improved.

In addition, for the same reason, instead of using the stride/height, for example, it may be configured such that users are classified into a plurality of clusters in accordance with the heights, and the analysis of the running characteristic and the like are performed for each cluster.

Furthermore, since motions during a game and a training method are different for each sport, characteristics of the running method may be easily configured to be different according to the type of a sport experienced by a user. For example, it is highly possible that a person who has experienced short-distance running has learned a stride running method by being trained to increase the stride. On the other hand, for example, it is highly possible that a person who has experienced long-distance running has learned a running method having superior stamina efficiency. In addition, for example, it is highly possible that a person who has experienced a ball game has learned a running method (in other words, a pitch running method) having a short duration of a flight so as to quickly change the posture or the direction.

Thus, for example, it may be configured such that users are classified into a plurality of clusters in accordance with the types of sports experienced in the past, and an analysis process of the running characteristic, the cardiorespiratory ability, the stamina characteristic, and the like is performed. In such a case, the analysis accuracy is improved.

In addition, users may be classified into a plurality of clusters by using a parameter representing an experience amount such as the number of experience years in addition to the types of experienced sports.

Other Modified Example

In the description presented above, while an example has been illustrated in which the relation among the remaining stamina amount, the speed, and the stamina efficiency or the relation among the remaining stamina amount, the pitch and the stride, and the stamina efficiency is acquired as the stamina efficiency characteristic, for example, the relation among the remaining stamina amount, the pitch, and the stamina efficiency or the relation among the remaining stamina amount, the stride, and the stamina efficiency may be acquired as the stamina efficiency characteristic.

In the process described as above, instead of the user's heart rate, the pulse rate may be used for the measurement.

Other Application Example

In the description presented above, while an example has been illustrated in which the present technology is applied to a case where running is supported based on the person's running characteristic, also in a case where the movement of a person other than running is supported based on another movement characteristic having a characteristic similar to the person's running characteristic, the present technology can be applied.

Here, the movement characteristic, for example, is represented using a relation among the speed, the number of unit movement operations per unit time, and the movement distance per unit movement operation. In case of the running characteristic, one step corresponds to the unit movement operation, the pitch corresponds to the number of unit movement operations per unit time, and the stride corresponds to the movement distance per the unit movement operation.

For example, in a case where the person's walking characteristic has characteristics similar to the running characteristic, the present technology can be applied to a case where walking support is executed. Here, the walking characteristic, similarly to the running characteristic, for example, is represented by a relation among the speed, the pitch, and the stride at the time of walking.

Thus, for example, by using the present technology, the analysis of the walking characteristic and the walking state of a person, support of training of race walking and the like, generation of a walking plan, and the like are executed by using a method similar to the method described above.

In addition, for example, in a case where a swimming characteristic of a person has characteristics similar to the running characteristic of a person, the present technology can be applied to a case where swimming support is executed.

The swimming characteristic, for example, is represented by a relation among a speed, a pitch, and a stroke length. Here, the pitch is also referred to as a stroke rate and is the number of times of paddling water per unit time, and the stroke length is a distance advanced by one stroke. Accordingly, one stroke corresponds to the unit movement operation, the pitch corresponds to the number of unit movement operations per unit time, and the stroke length corresponds to the movement distance per the unit movement operation.

Thus, for example, by using the present technology, the analysis of the swimming characteristic and the swimming state of a person, support of training of swimming, generation of a swimming plan, and the like are executed by using a method similar to the method described above.

Figure 62:
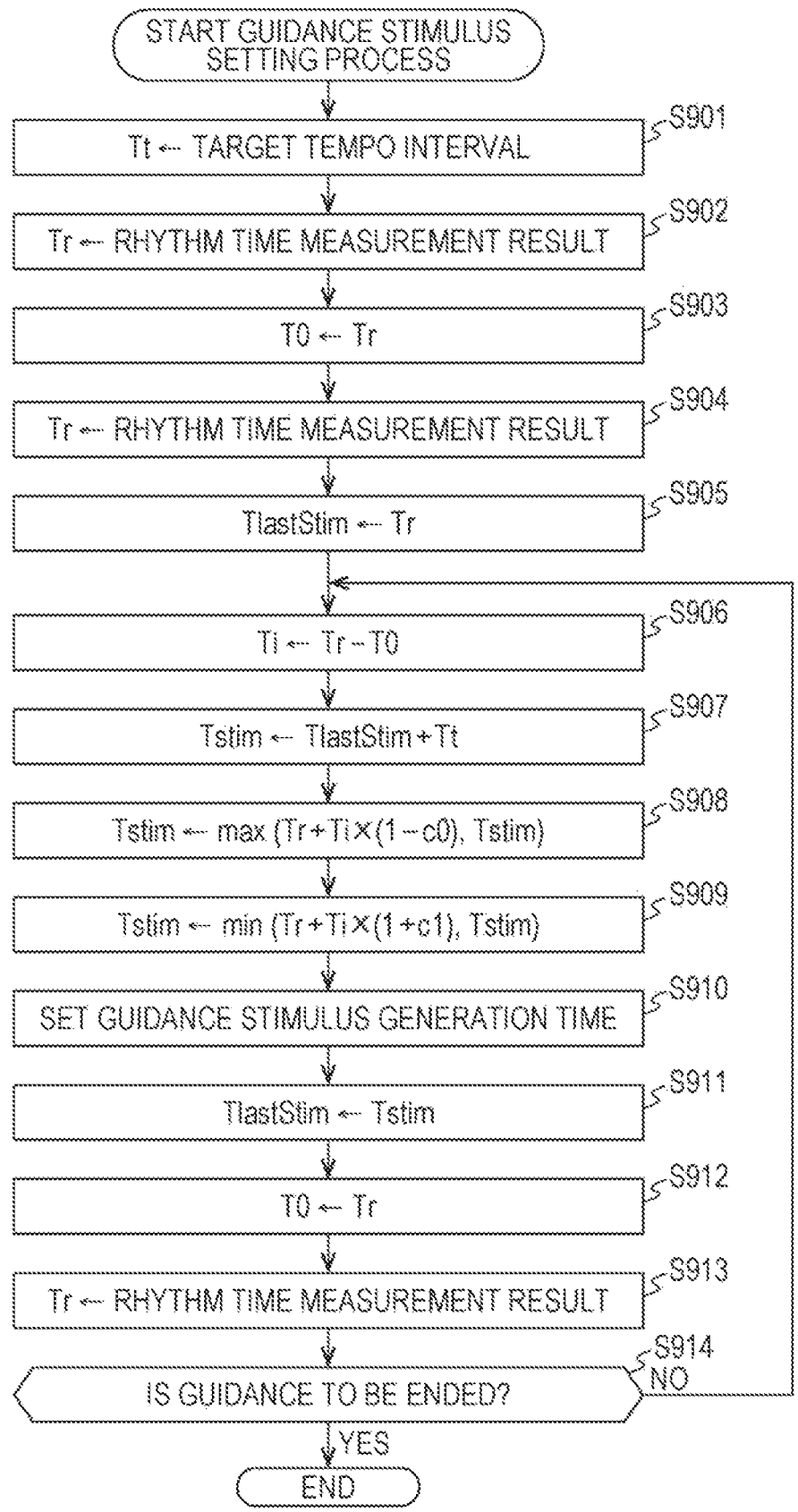
FIG. 62 is a flowchart that illustrates a guide stimulus setting process.

In addition, the guide stimulus setting process illustrated in FIG. 62 can be also applied to a case where the rhythm or tempo of a user's behavior other than the pitch at the time of running is guided. For example, as the user's behavior that is a guiding target, swimming, walking, singing, play of music, and the like may be considered. In addition, as the rhythm time of step S902 illustrated in FIG. 62, for example, time at which hands paddling water in the swimming are landing on the water, time when a sound corresponding to the rhythm of music is generated, and the like are considered.

{Example of Configuration of Computer}

A series of the processes described above can be performed either by hardware or by software. In a case where the series of the processes is performed by software, a program configuring the software is installed to a computer. Here, the computer includes a computer that is built in dedicated hardware, a computer such as a general-purpose personal computer that can execute various functions by installing various programs thereto, and the like.

Figure 66:
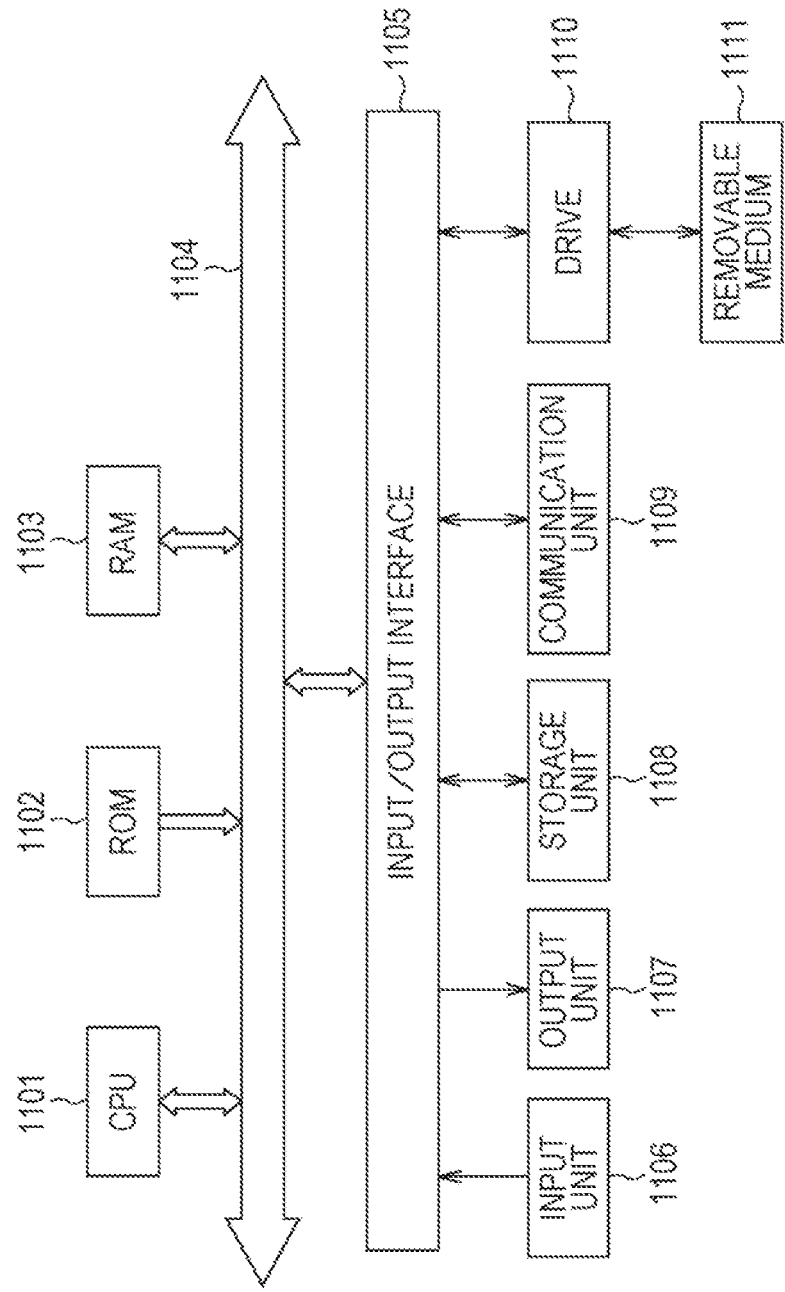
FIG. 66 is a block diagram that illustrates an example of the configuration of a computer.

FIG. 66 is a block diagram that illustrates an example of the hardware configuration of a computer that executes the series of processes described above by using a program.

In the computer, a CPU 1101, a ROM 1102, and a RAM 1103 are interconnected through a bus 1104.

In addition, an input/output interface 1105 is connected to the bus 1104. An input unit 1106, an output unit 1107, a storage unit 1108, a communication unit 1109, and a drive 1110 are connected to the input/output interface 1105.

The input unit 1106 is configured by a keyboard, a mouse, a microphone, and the like. The output unit 1107 is configured by a display, a speaker, and the like. The storage unit 1108 is configured by a hard disk, a non-volatile memory, and the like. The communication unit 1109 is configured by a network interface and the like. The drive 1110 drives a magnetic disk, an optical disc, a magneto-optical disk, or a removable medium 1111 such as a semiconductor memory.

In the computer configured as above, the CPU 1101, for example, loads a program stored in the storage unit 1108 into the RAM 1103 through the input/output interface 1105 and the bus 1104 and executes the loaded program, thereby executing the series of the processes described above.

The program executed by the computer (the CPU 1101), for example, may be provided with being recorded on a removable medium 1111 as a package medium or the like. In addition, the program may be provided through a wired or wireless transmission medium such as a local area network, the Internet, or digital satellite broadcast.

In the computer, by loading the removable medium 1111 into the drive 1110, the program can be installed to the storage unit 1108 through the input/output interface 1105. In addition, the program may be received by the communication unit 1109 through a wired or wireless transmission medium and be installed to the storage unit 1108. Furthermore, the program may be installed to the ROM 1102 or the storage unit 1108 in advance.

In addition, the program executed by the computer may be a program that executes the processes in a time series along the sequence described in this specification or a program that executes the processes in a parallel manner or at necessary timing such as at the timing of being called.

In this specification, a system represents a set of a plurality of constituent elements (an apparatus, a module (component), and the like), and all the constituent elements are not necessarily disposed in a same casing. Thus, a plurality of apparatuses that are housed in separate casings and are connected through a network and one apparatus in which a plurality of modules are housed in one casing are systems.

In addition, the present technology is not limited to the embodiments described above, and various changes can be made therein in a range not departing from the concept of the present technology.

For example, the present technology may employ a configuration of cloud computing in which one function is divided into and processed altogether by a plurality of apparatuses through a network.

In addition, each step described in each flowchart described above may be either executed by one apparatus or executed by a plurality of apparatuses in a shared manner.

Furthermore, in a case where a plurality of processes are included in one step, the plurality of processes included in the one step may be either executed by one apparatus or executed by a plurality of apparatuses in a shared manner.

The effects described here are merely examples but are not for the purposes of limitation, and any other effect may be present.

In addition, the present technology is not limited to the embodiments described above, and various changes can be made therein in a range not departing from the concept of the present technology.

For example, the present technology may take configurations as below.

(1) An information processing apparatus including circuitry configured to initiate a providing of guidance at least one of a speed, a pitch, and a stride of a user's movement, based on a movement characteristic representing a relation among a combination of the speed, the pitch, and the stride during the user's movement, wherein the guidance is provided based on sensing information associated with the user's movement.

(2) The information processing apparatus according to (1), wherein the circuitry is further configured to control presentation of at least one of the movement characteristic of the user's movement and a result of an analysis of a movement state of the user based on the movement characteristic.

(3) The information processing apparatus according to (1) or (2), wherein the circuitry is further configured to execute control such that a result of analyzing balance of the pitch and the stride of the user's movement based on the movement characteristic is presented.

(4) The information processing apparatus according to any of (1) through (3), wherein the circuitry is further configured to execute control such that transitions of time series of the balance of the pitch and the stride along with the speed of the user's movement are presented.

(5) The information processing apparatus according to any of (1) through (4), wherein the circuitry is further configured to control presentation of at least one of a result of comparing balances of the pitches and the strides of the user at a plurality of time points in a time series and a result of comparing balances of the pitches and the strides of a plurality of users' movements.

(6) The information processing apparatus according to any of (1) through (5), wherein the circuitry is further configured to analyze a movement state of the user's movement based on the user's movement characteristic.

(7) The information processing apparatus according to any of (1) through (6), wherein the guidance is provided such that one of the speed, the pitch, and the stride is fixed, and the remaining two thereof are changed.

(8) The information processing apparatus according to any of (1) through (7), wherein the guidance is provided on the pitch and the stride of the user's movement such that a heart rate or a pulse rate of the user is within a threshold amount of a predetermined constant.

(9) The information processing apparatus according to any of (1) through (8), wherein the circuitry is further configured to initiate generation of a plan including at least one selected from a group consisting of distribution of the pitch and the stride in a course in which the user moves and distribution of the speed in the course based on a stamina characteristic of the user, wherein the guidance is provided on the speed, the pitch, and the stride of the user's movement based on the generated plan.

(10) The information processing apparatus according to any of (1) through (9), wherein the circuitry is further configured to update the plan during the user's movement based on the movement state of the user and a condition.

(11) The information processing apparatus according to any of (1) through (10), wherein the circuitry is further configured to update the plan while adjusting a remainder of a stamina amount according to the stamina characteristic of the user at a goal time based on a remaining distance of the course.

(12) The information processing apparatus according to any of (1) through (11), wherein the stamina characteristic of the user includes a stamina efficiency characteristic representing a relation among at least one selected from a group consisting of the speed, the pitch, and the stride of the user's movement, a remaining stamina amount and stamina efficiency, and a stamina capacity of the user.

(13) The information processing apparatus according to any of (1) through (12), wherein the guidance is provided on the stride in a case where the speed of the user is less than a predetermined speed threshold, and guidance is provided on the pitch in a case where the speed of the user is equal to or greater than the predetermined speed threshold.

(14) The information processing apparatus according to any of (1) through (13), wherein the circuitry is further configured to analyze the movement characteristic of the user's movement based on measurement results of the pitch and the stride of the user's movement for at least two different speeds including a first speed and a second speed.

(15) The information processing apparatus according to any of (1) through (14), wherein the first speed and the second speed are lower than a switching speed that is a speed at which the circuitry is configured to control switching between a method of controlling acceleration by increasing the stride and a method of controlling acceleration by increasing the pitch.

(16) The information processing apparatus according to any of (1) through (15), wherein the circuitry is further configured to analyze the movement characteristic of the user's movement based on measurement results of the pitch and the stride of the user's movement for at least three different speeds including a first speed lower than a switching speed that is a speed at which the circuitry is configured to control switching between a method of controlling acceleration by increasing the stride and a method of controlling acceleration by increasing the pitch, a second speed higher than the switching speed, and a third speed that is between the first speed and the second speed.

(17) The information processing apparatus according to any of (1) through (16), wherein the circuitry is further configured to analyze a cardiorespiratory capacity of the user based on a heart rate or a pulse rate measured while guidance is provided on the at least one selected from the group consisting of the speed, the pitch, and the stride of the user's movement.

(18) The information processing apparatus according to any of (1) through (17), wherein the cardiorespiratory capacity includes an average heart rate and a highest heart rate of the user.

(19) The information processing apparatus according to any of (1) through (18), wherein the circuitry is further configured to analyze a stamina characteristic of the user based on a combination of the speed measured while guidance is provided on the at least one selected from the group consisting of the speed, the pitch, and the stride of the user's movement and a measurement result of a heart rate or a pulse rate.

(20) The information processing apparatus according to any of (1) through (19), wherein the movement characteristic of the user's movement represents a combination of the pitch and the stride at each speed during the user's movement, and the movement state is a running state of the user.

(21) The information processing apparatus according to any of (1) through (20), wherein the pitch is determined based on a number of unit movement operations of the user per unit of time.

(22) An information processing method, performed via at least one processor, the method including guiding at least one selected from a group consisting of a speed, a pitch, and a stride of a user's movement, based on a movement characteristic representing a relation among a combination of the speed, the pitch, and the stride during the user's movement, wherein the guidance is provided based on sensing information associated with the user's movement.

(23) A non-transitory computer-readable storage medium having embodied thereon a program, wherein when executed by a computer causes the computer to execute a method, the method including guiding at least one selected from a group consisting of a speed, a pitch, and a stride of a user's movement, based on a movement characteristic representing a relation among a combination of the speed, the pitch, and the stride during the user's movement, wherein the guidance is provided based on sensing information associated with the user's movement.

REFERENCE SIGNS LIST

101 Information Processing System
111 Server
112-1 to 112-n Client
121-1 to 121-n Mobile terminal
122-1 to 122-n Wearable terminal
201 CPU
251 Analysis unit
252 Running plan generating unit
261 Running characteristic analyzing unit
262 Cardiorespiratory capacity analyzing unit
263 Stamina characteristic analyzing unit
301 CPU
305 Input unit
306 Output unit
351 Analysis unit
352 Guide unit
353 UI control unit
361 Running state analyzing unit
401 CPU
404 Input unit
405 Output unit
406 Measurement unit
421 GPS receiver
422 Heart rate sensor
423 Acceleration sensor
424 Gyro sensor
425 Air pressure sensor
426 Temperature sensor
427 Humidity sensor
471 Data collecting unit
472 UI control unit

The invention claimed is:

1. An information processing apparatus comprising:
circuitry configured to
initiate a providing of guidance on at least one selected from a group consisting of a speed, a pitch, and a stride of a user's movement, based on a movement characteristic curve representing a relation among a combination of the speed, the pitch, and the stride during the user's movement,
wherein the guidance is provided based on sensing information associated with the user's movement, and
wherein the circuitry is further configured to analyze the movement characteristic curve of the user's movement based on measurement results of the pitch and the stride of the user for at least two different speeds including a first speed and a second speed.

2. The information processing apparatus according to claim 1, wherein the circuitry is further configured to control presentation of at least one of the movement characteristic curve of the user's movement and a result of an analysis of a movement state of the user based on the movement characteristic curve.

3. The information processing apparatus according to claim 2, wherein the circuitry is further configured to execute control such that a result of analyzing balance of the pitch and the stride of the user's movement based on the movement characteristic curve is presented.

4. The information processing apparatus according to claim 3, wherein the circuitry is further configured to execute control such that transitions of time series of the balance of the pitch and the stride along with the speed of the user's movement are presented.

5. The information processing apparatus according to claim 2, wherein the circuitry is further configured to control presentation of at least one of a result of comparing balances of the pitches and the strides of the user at a plurality of time points in a time series and a result of comparing balances of the pitches and the strides of a plurality of users' movements.

6. The information processing apparatus according to claim 1, wherein the circuitry is further configured to analyze a movement state of the user's movement based on the user's movement characteristic curve.

7. The information processing apparatus according to claim 1, wherein the guidance is provided such that one of the speed, the pitch, and the stride is fixed, and the remaining two thereof are changed.

8. The information processing apparatus according to claim 1, wherein the guidance is provided on the pitch and the stride of the user's movement such that a heart rate or a pulse rate of the user is within a threshold amount of a predetermined constant.

9. The information processing apparatus according to claim 1, wherein the circuitry is further configured to initiate generation of a plan including at least one selected from a group consisting of distribution of the pitch and the stride in a course in which the user moves and distribution of the speed in the course based on a stamina characteristic of the user,
wherein the guidance is provided on the speed, the pitch, and the stride of the user's movement, based on the generated plan.

10. The information processing apparatus according to claim 9, wherein the circuitry is further configured to update the plan during the user's movement based on the movement state of the user and a condition.

11. The information processing apparatus according to claim 9, wherein the circuitry is further configured to update the plan while adjusting a remainder of a stamina amount according to the stamina characteristic of the user at a goal time based on a remaining distance of the course.

12. The information processing apparatus according to claim 9, wherein the stamina characteristic of the user includes a stamina efficiency characteristic representing a relation among at least one selected from a group consisting of the speed, the pitch, and the stride of the user's movement, a remaining stamina amount and stamina efficiency, and a stamina capacity of the user.

13. The information processing apparatus according to claim 1, wherein the guidance is provided on the stride in a case where the speed of the user is less than a predetermined speed threshold, and guidance is provided on the pitch in a case where the speed of the user is equal to or greater than the predetermined speed threshold.

14. The information processing apparatus according to claim 1, wherein the first speed and the second speed are lower than a switching speed that is a speed at which the circuitry is configured to control switching between a method of controlling acceleration by increasing the stride and a method of controlling acceleration by increasing the pitch.

15. The information processing apparatus according to claim 1, wherein the circuitry is further configured to analyze the movement characteristic curve of the user's movement based on measurement results of the pitch and the stride of the user's movement for at least three different speeds including the first speed lower than a switching speed that is a speed at which the circuitry is configured to control switching between a method of controlling acceleration by increasing the stride and a method of controlling acceleration by increasing the pitch, the second speed higher than the switching speed, and a third speed that is between the first speed and the second speed.

16. The information processing apparatus according to claim 1, wherein the circuitry is further configured to analyze a cardiorespiratory capacity of the user based on a heart rate or a pulse rate measured while guidance is provided on the at least one selected from the group consisting of the speed, the pitch, and the stride of the user's movement.

17. The information processing apparatus according to claim 16, wherein the cardiorespiratory capacity includes an average heart rate and a highest heart rate of the user.

18. The information processing apparatus according to claim 1, wherein the circuitry is further configured to analyze a stamina characteristic of the user based on a combination of the speed measured while guidance is provided on the at least one selected from the group consisting of the speed, the pitch, and the stride of the user's movement and a measurement result of a heart rate or a pulse rate.

19. The information processing apparatus according to claim 2, wherein
the movement characteristic curve of the user's movement represents a combination of the pitch and the stride at each speed during the user's movement, and
the movement state is a running state of the user.

20. The information processing apparatus according to claim 1, wherein the pitch is determined based on a number of unit movement operations of the user per unit of time.

21. An information processing method, performed via at least one processor, the method comprising:
guiding at least one selected from a group consisting of a speed, a pitch, and a stride of a user's movement, based on a movement characteristic curve representing a relation among a combination of the speed, the pitch, and the stride during the user's movement,
wherein the guidance is provided based on sensing information associated with the user's movement, and
wherein the movement characteristic curve of the user's movement is analyzed based on measurement results of the pitch and the stride of the user for at least two different speeds including a first speed and a second speed.

22. A non-transitory computer-readable medium having embodied thereon a program, which when executed by a computer causes the computer to execute a method, the method comprising:
guiding at least one selected from a group consisting of a speed, a pitch, and a stride of a user's movement, based on a movement characteristic curve representing a relation among a combination of the speed, the pitch, and the stride during the user's movement,
wherein the guidance is provided based on sensing information associated with the user's movement, and
wherein the movement characteristic curve of the user's movement is analyzed based on measurement results of the pitch and the stride of the user for at least two different speeds including a first speed and a second speed.

* * * * *